United States Patent
Chen et al.

(10) Patent No.: US 7,250,515 B2
(45) Date of Patent: Jul. 31, 2007

(54) THIAZOLINONE 3,4-DISUBSTITUTED QUINOLINES

(75) Inventors: Li Chen, Shanghai (CN); Shaoqing Chen, Bridgewater, NJ (US); Christophe Michoud, New York, NY (US)

(73) Assignee: Hoffman-La Roche Inc., Nutley, NJ (US)

( * ) Notice: Subject to any disclaimer, the term of this patent is extended or adjusted under 35 U.S.C. 154(b) by 211 days.

(21) Appl. No.: 11/170,450

(22) Filed: Jun. 29, 2005

(65) Prior Publication Data

US 2006/0004046 A1    Jan. 5, 2006

Related U.S. Application Data

(60) Provisional application No. 60/658,273, filed on Mar. 3, 2005, provisional application No. 60/584,931, filed on Jul. 1, 2004.

(51) Int. Cl.
  *C07D 417/06* (2006.01)
(52) U.S. Cl. .................................................. 546/135
(58) Field of Classification Search ................ 546/135; 548/190
  See application file for complete search history.

(56) References Cited

FOREIGN PATENT DOCUMENTS

EP           1215208 A2      6/2002
WO    WO 2004047760 A2 *    6/2004

* cited by examiner

*Primary Examiner*—D. Margaret Seaman
*Assistant Examiner*—Nizal S. Chandrakumar
(74) *Attorney, Agent, or Firm*—George W. Johnston; Patricia S. Rocha-Tramaloni; David E. Wildman

(57) ABSTRACT

Thiazolinone disubstituted quinoline derivatives where the quinoline ring is disubstituted at the 3, 4 positions which derivatives demonstrate CDK1 antiproliferative activity and are useful as anti-cancer agents.

60 Claims, No Drawings

THIAZOLINONE 3,4-DISUBSTITUTED QUINOLINES

PRIORITY TO RELATED APPLICATIONS

This application claims the benefit of Provisional Application(s) Ser. No. 60/584,931, filed Jul. 1, 2004 and Ser. No. 60/658,273, filed Mar. 3, 2005.

FIELD OF THE INVENTION

The field of this invention relates to thiazolinone disubstituted quinoline derivatives where the quinoline ring is disubstituted at 3,4-positions, which derivatives demonstrate CDK1 antiproliferative activity and are useful as anti-cancer agents.

BACKGROUND OF THE INVENTION

Cyclin-dependent kinases (CDKs) are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. (See, e.g., the articles compiled in *Science*, 274:1643-1677 (1996); and *Ann. Rev. Cell Dev. Biol.*, 13:261-291 (1997)). CDK complexes are formed through association of a regulatory cyclin subunit (e.g., cyclin A, B1, B2, D1, D2, D3 and E) and a catalytic kinase subunit (e.g., CDK1, CDK2, CDK4, CDK5 and CDK6). As the name implies, the CDKs display an absolute dependence on the cyclin subunit in order to phosphorylate their target substrates, and different kinase/cyclin pairs function to regulate progression through specific phases of the cell-cycle.

As seen above, these protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

In view of the above properties, these kinases play an important part in the propagation of growth factor signal transduction that leads to cellular proliferation, differentiation and migration. Fibroblast growth factor (FGF) and vascular endothelial growth factor (VEGF) have been recognized as important mediators of tumor promoted angiogenesis. VEGF activates endothelial cells by signaling through two high affinity receptors, one of which is the kinase insert domain-containing receptor (KDR). (See, Hennequin L. F. et. al., *J. Med. Chem.* 45(6):1300 (2002). FGF activates endothelial cells by signaling through the FGF receptor (FGFR). Solid tumors depend upon the formation of new blood vessels (angiogenesis) to grow. Accordingly, inhibitors of the receptors FGFR and KDR that interfere with the growth signal transduction, and thus slow down or prevent angiogenesis, are useful agents in the prevention and treatment of solid tumors. (See, Klohs W. E. et. al., *Current Opinion in Biotechnology*, 10:544 (1999)).

Because CDKs such as CDK1 serve as general activators of cell division, inhibitors of CDK1 can be used as antiproliferative agents. These inhibitors can be used for developing therapeutic intervention in suppressing deregulated cell cycle progression.

SUMMARY OF THE INVENTION

In accordance with this invention, it has been discovered that the compound of the formula:

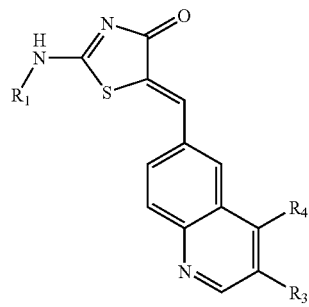

wherein $R_1$ is hydrogen, lower alkyl, cyclolower alkyl, aryloxy-lower alkyl, lower alkoxy, hydroxyl lower alkyl, —NH$_2$, —[CH$_2$CH$_2$O]$_v$R$_8$ or R$_2$—(X)$_n$—

X is lower alkylene, cycloloweralkylene, aryl lower alkylene, carboxyloweralkylene, hydroxy lower alkylene, amido lower alkylene, mono- or di-halo lower alkylene, amino lower alkylene, mono- or di-lower alkyl amino lower alkylene or imido lower alkylene, $R_2$ is

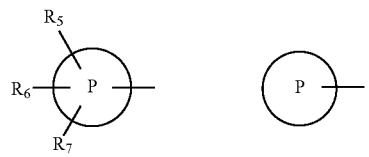

is an aryl ring, cyclo lower alkyl ring containing from 3 to 6 carbon atoms, a 4 to 6 membered heterocycloalkyl ring containing from 3 to 4 carbon atoms and from 1 to 2 hetero atoms selected from the group consisting of oxygen, nitrogen and sulfur, or a 5 or 6 membered heteroaromatic ring containing from 1 to 2 hetero atoms selected from the group consisting of oxygen, sulfur and nitrogen;

$R_5$, $R_6$ and $R_7$ are independently selected from the group consisting of hydroxy, lower alkyl sulfone, hydroxy-lower alkyl, hydrogen, lower alkyl, halogen, perfluro lower alkyl, lower alkoxy, amino, mono- or di-lower alkyl amino, and when two of the substituents $R_5$, $R_6$ and $R_7$ are substituted on adjacent carbon atoms on ring

these two substituents can be taken together with their adjacent, attached carbon atoms to form an aryl ring, a 3 to 6 membered cyclolower alkyl ring, a 4 to 6 membered heterocycloalkyl ring or a 4 to 6 membered heteroaromatic ring, said heterocycloalkyl ring and said heteroaromatic ring containing from 1 to 2 hetero atoms selected from the group consisting of oxygen, nitrogen or sulfur;

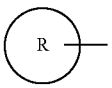

is selected from an aryl ring, a cycloalkyl ring containing from 3 to 6 carbon atoms, a 4 to 6 membered heterocyclic alkyl ring containing from 1 to 2 hetero atoms selected from the group consisting of a oxygen, sulfur and nitrogen or a 5 to 6 numbered heteroaromatic ring containing from 1 to 2 hetero atoms selected from the group consisting of oxygen sulfur and nitrogen;

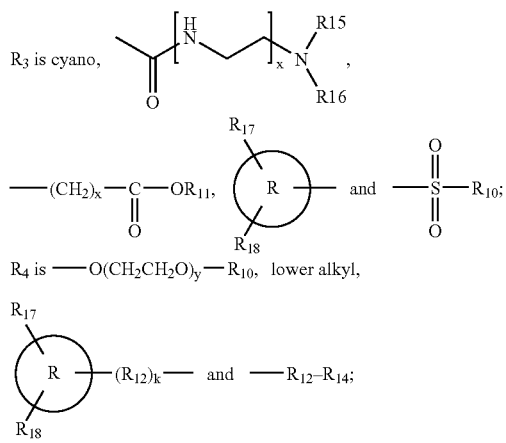

$R_8$, $R_{11}$, $R_{15}$, $R_{16}$, $R_{17}$ and $R_{18}$ are independently hydrogen or lower alkyl;

$R_{10}$ is lower alkyl;

$R_{12}$ is O or S;

$R_{14}$ is selected from hydroxyalkyl, lower alkyl, cycloalkyl, haloalkyl;

perfluoroalkyl and protected hydroxyalkyl;

x, n and k are integers from 0 to 1;

z is an integer from 0 to 3;

y is the integer from 1 to 3;

v is an integer from 1 to 6; or

N-oxides of compounds where $R_2$ contains a nitrogen in the heterocycloalkyl ring or heteroaromatic ring, sulfones where $R_2$ contains a sulfur in the heterocycloalkyl ring or heteroaromatic ring, or pharmaceutically acceptable salts thereof, inhibit the activity of CDKs, particularly, CDK1.

These inventive agents and pharmaceutical compositions containing such agents are useful in treating various diseases or disorder states associated with uncontrolled or unwanted cellular proliferation, such as cancer, autoimmune diseases, viral diseases, fungal diseases, neurodegenerative disorders and cardiovascular diseases.

Inhibiting and/or modulating the activity of CDKs, particularly CDK1, makes these compounds of formula and compositions containing these compounds useful in treating diseases medicated by kinase activity, particularly as anti-tumor agents in treating cancers.

DETAILED DESCRIPTION OF THE INVENTION

As pointed out herein, the compounds of formula I are potential anti-proliferation agents and are useful for mediating and/or inhibiting the activity of CDKs, particularly CDK1, thus providing anti-tumor agents for treatment of cancer or other diseases associated with uncontrolled or abnormal cell proliferation.

Among the preferred compounds of formula I are the compounds of the formula:

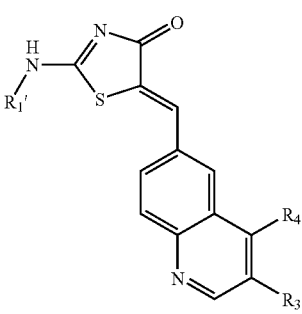

I-A wherein $R_1'$ is selected from hydrogen, lower alkyl, cyclolower alkyl, lower alkoxy, aryloxy-lower alkyl, —$NH_2$, hydroxyl lower alkyl, or $[CH_2CH_2O]_vR_8$;

and v, $R_3$, $R_4$ and $R_8$ are as above, or pharmaceutically acceptable salts thereof and compounds of the formula:

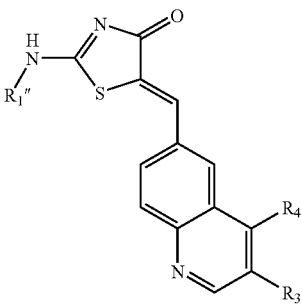

I-B wherein $R_1''$ is $R'_2$—$(X)_n$—;

n, $R_3$ and $R_4$ are as above, and

X is selected from lower alkylene, cyclo lower alkylene, aryl lower alkylene, carboxy lower alkylene, hydroxy lower alkylene, amido lower alkylene, mono- or di-halo lower alkylene, amino lower alkylene, mono- or di-lower alkyl amino lower alkylene and imido lower alkylene;

$R_2$ is

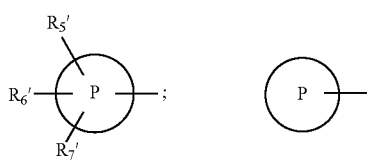

is selected from an aryl ring, cycloalkyl ring containing from 3 to 6 carbon atoms, a 4 to 6 membered heterocycloalkyl ring containing from 3 to 5 carbon atoms and from 1 to 2 hetero atoms selected from the group consisting of oxygen, nitrogen and sulfur, a 5 or 6 membered heteroaromatic ring containing from 1 to 2 hetero atoms selected from the group consisting of oxygen, sulfur and nitrogen;

$R_5'$, $R_6'$ and $R_7'$ are independently selected from the group consisting of hydroxy, lower alkyl sulfone, hydroxy lower alkyl, hydrogen, lower alkyl, halogen, perfluro lower alkyl, lower alkoxy, amino, mono- or di-lower alkyl amino, or or N-oxides of compounds where $R_2'$ contains a nitrogen in the heterocycloalkyl or heteroaromatic ring, sulfones where $R_2'$ contains a sulfur in the hetero ring or heteroaromatic ring, or pharmaceutically acceptable salts thereof.

Among the compounds of formula I are the preferred embodiments of the compounds of formula I-A and formula I-B where the aryl groups in all of the aryl substituents are preferable phenyl.

A class of compounds having the preferred substituents on the compound of formula I, I-A and I-B are these compounds where $R_3$ is cyano,

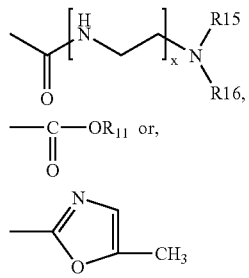

and $R_4$ is $-O(CH_2CH_2O)_y-R_{10}$ or
$-O-R_{14}$, $-S-R_{14}$, lower alkyl or

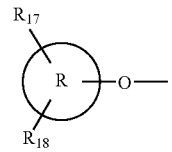

Among the preferred embodiments of the class of compounds of formula I-A are those compounds of formula I-A where $R_1$ is $-[CH_2CH_2O]_vR_8$ where $R_8$ and v are as above.

In the especially preferred embodiment of this class of compounds are those compounds where $R_3$ is cyano.

Another preferred class of compounds of formula I-A are these compounds where $R_1$ is hydrogen. Among this preferred class of compounds are those compounds where $R_3$ is cyano and $R_4$ is $-O(CH_2CH_2O)_y-R_{10}$, $-O-R_{14}$, $-S-R_{14}$, lower alkyl or

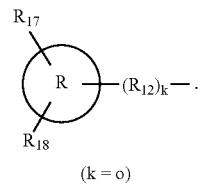

(k = o)

Another preferred embodiment of the compound of formula I-A are those class of compounds where $R_1$ is a lower alkyl group.

Among the preferred embodiment of the compounds of formula I-B are these class of compounds in which n is o and $R_2'$ is a cyclolower alkyl ring especially cyclopropyl.

Among this class of compounds, where $R_2'$ is a cyclo lower alkyl and n is 0, those compounds where $R_3$ cyano and $R_4$ is $-O(CH_2CH_2O)_y-R_{10}$, lower alkyl, or

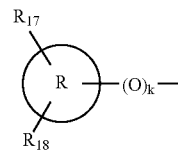

are especially preferred.

Another preferred embodiment of this compound of formula I-B is the class of compounds where n is 1. In this case, the preferred embodiments of this class of compounds are those compounds where X is lower alkylene, hydroxy lower alkylene, cyclolower alkylene or mono- or di-halo lower alkylene. In these cases, $R_3$ is preferably cyano, or $-COOR_{11}$
where $R_{11}$ is as above and $R_4$ is alkyl or cycloalkyl or $-O(CH_2CH_2O)_y-R_{10}$ where y, $R_{10}$, and $R_{11}$, are as above.

In compounds I and I-B, where $R_1$, $R_1''$, $R_2'$ and X are substituents containing an aryl moiety, the preferred aryl moiety is phenyl.

Especially preferred compounds are compounds of the formula:

4-Methoxy-6-[4-oxo-2-((1R,2S)-2-phenyl-cyclopropylamino)-4H-thiazol-(5Z)-ylidenemethyl]-quinoline-3-carboxylic acid methyl ester;

4-Methoxy-6-[4-oxo-2-((1R,2S)-2-phenyl-cyclopropylamino)-4H-thiazol-(5Z)-ylidenemethyl]-quinoline-3-carboxylic acid amide;

6-[2-((R)-1-Hydroxymethyl-2-phenyl-ethylamino)-4-oxo-4H-thiazol-(5Z)-ylidenemethyl]-4-methoxy-quinoline-3-carboxylic acid amide;

6-[2-((R)-2-Hydroxy-1-phenyl-ethylamino)-4-oxo-4H-thiazol-(5Z)-ylidenemethyl]-4-methoxy-quinoline-3-carboxylic acid amide;

6-[2-((R)-2-Hydroxy-1-phenyl-ethylamino)-4-oxo-4H-thiazol-(5Z)-ylidenemethyl]-4-methoxy-quinoline-3-carboxylic acid methyl ester;

4-Methoxy-6-[4-oxo-2-((1R,2S)-2-phenyl-cyclopropylamino)-4H-thiazol-(5Z)-ylidenemethyl]-quinoline-3-carboxylic acid;

6-[2-((R)-2-Hydroxy-1-phenyl-ethylamino)-4-oxo-4H-thiazol-(5Z)-ylidenemethyl]-4-methoxy-quinoline-3-carboxylic acid;

4-Methoxy-6-[4-oxo-2-((1R,2S)-2-phenyl-cyclopropylamino)-4H-thiazol-(5Z)-ylidenemethyl]-quinoline-3-carboxylic acid (2-dimethylamino-ethyl)-amide; hydrochloride;

4-Ethoxy-6-[4-oxo-2-((1R,2S)-2-phenyl-cyclopropylamino)-4H-thiazol-(5Z)-ylidenemethyl]-quinoline-3-carboxylic acid ethyl ester;

4-Methoxy-6-[4-oxo-2-((1R,2S)-2-phenyl-cyclopropylamino)-4H-thiazol-(5Z)-ylidenemethyl]-quinoline-3-carboxylic acid dimethylamide;

4-Methoxy-6-[4-oxo-2-((1R,2S)-2-phenyl-cyclopropylamino)-4H-thiazol-(5Z)-ylidenemethyl]-quinoline-3-carboxylic acid methyl ester;

4-Ethoxy-6-[2-[2-(3-fluoro-phenyl)-ethylamino]-4-oxo-4H-thiazol-(5Z)-ylidenemethyl]-quinoline-3-carbonitrile;

4-Ethoxy-6-[4-oxo-2-((1R,2S)-2-phenyl-cyclopropylamino)-4H-thiazol-(5Z)-ylidenemethyl]-quinoline-3-carbonitrile;

4-Ethoxy-6-[2-((R)-2-hydroxy-1-phenyl-ethylamino)-4-oxo-4H-thiazol-(5Z)-ylidenemethyl]-quinoline-3-carbonitrile;

6-[2-Amino-4-oxo-4H-thiazol-(5Z)-ylidenemethyl]-4-ethoxy-quinoline-3-carbonitrile;

2-[2-(3-Fluoro-phenyl)-ethylamino]-5-[1-[4-methoxy-3-(5-methyl-oxazol-2-yl)-quinolin-6-yl]-meth-(5Z)-ylidene]-thiazol-4-one;

4-Ethoxy-6-[4-oxo-2-[(pyridin-2-ylmethyl)-amino]-4H-thiazol-(5Z)-ylidenemethyl]-quinoline-3-carbonitrile;

4-Ethoxy-6-[2-(2-hydroxy-2-phenyl-ethylamino)-4-oxo-4H-thiazol-(5Z)-ylidenemethyl]-quinoline-3-carbonitrile;

4-Ethoxy-6-[4-oxo-2-[(4-trifluoromethyl-pyridin-2-ylmethyl)-amino]-4H-thiazol-(5Z)-ylidenemethyl]-quinoline-3-carbonitrile;

4-Ethoxy-6-[2-(2-imidazol-1-yl-ethylamino)-4-oxo-4H-thiazol-(5Z)-ylidenemethyl]-quinoline-3-carbonitrile;

4-Ethoxy-6-[4-oxo-2-[(pyrazin-2-ylmethyl)-amino]-4H-thiazol-(5Z)-ylidenemethyl]-quinoline-3-carbonitrile;

4-Ethoxy-6-[-4-oxo-2-[(pyrimidin-2-ylmethyl)-amino]-4H-thiazol-(5Z)-ylidenemethyl]-quinoline-3-carbonitrile;

6-[2-(2,2-Difluoro-2-pyridin-2-yl-ethylamino)-4-oxo-4H-thiazol-(5Z)-ylidenemethyl]-4-ethoxy-quinoline-3-carbonitrile;

6-[2-Cyclopropylamino-4-oxo-4H-thiazol-(5Z)-ylidenemethyl]-4-ethoxy-quinoline-3-carbonitrile;

4-Ethoxy-6-[2-[2-(2-methoxy-ethoxy)-ethylamino]-4-oxo-4H-thiazol-(5Z)-ylidenemethyl]-quinoline-3-carbonitrile;

4-Ethoxy-6-[4-oxo-2-[(tetrahydro-pyran-4-ylmethyl)-amino]-4H-thiazol-(5Z)-ylidenemethyl]-quinoline-3-carbonitrile;

4-Ethoxy-6-[4-oxo-2-[(thiazol-2-ylmethyl)-amino]-4H-thiazol-(5Z)-ylidenemethyl]-quinoline-3-carbonitrile;

6-[2-Amino-4-oxo-4H-thiazol-(5Z)-ylidenemethyl]-4-[2-(2-methoxy-ethoxy)-ethoxy]-quinoline-3-carbonitrile;

4-{6-[2-Amino-4-oxo-4H-thiazol-(5Z)-ylidenemethyl]-3-cyano-quinolin-4-yloxy}-piperidine-1-carboxylic acid tert-butyl ester;

6-[2-Amino-4-oxo-4H-thiazol-(5Z)-ylidenemethyl]-4-(piperidin-4-yloxy)-quinoline-3-carbonitrile;

6-[2-tert-Butylamino-4-oxo-4H-thiazol-(5Z)-ylidenemethyl]-4-ethoxy-quinoline-3-carbonitrile;

6-[2-Cyclopropylamino-4-oxo-4H-thiazol-(5Z)-ylidenemethyl]-4-[2-(2-methoxy-ethoxy)-ethoxy]-quinoline-3-carbonitrile;

4-{3-Cyano-6-[2-cyclopropylamino-4-oxo-4H-thiazol-(5Z)-ylidenemethyl]-quinolin-4-yloxy}-piperidine-1-carboxylic acid tert-butyl ester;

6-(2-Cyclopropylamino-4-oxo-4H-thiazol-5-ylidenemethyl)-4-(piperidin-4-yloxy)-quinoline-3-carbonitrile hydrochloride;

4-Ethoxy-6-[2-((S)-2-hydroxy-2-phenyl-ethylamino)-4-oxo-4H-thiazol-(5Z)-ylidenemethyl]-quinoline-3-carbonitrile;

4-Ethoxy-6-[2-(R)-2-hydroxy-2-phenyl-ethylamino)-4-oxo-4H-thiazol-(5Z)-ylidenemethyl]-quinoline-3-carbonitrile;

6-[2-Cyclopropylamino-4-oxo-4H-thiazol-(5Z)-ylidenemethyl]-4-isopropoxy-quinoline-3-carbonitrile;

6-[2-Amino-4-oxo-4H-thiazol-(5Z)-ylidenemethyl]-4-isopropoxy-quinoline-3-carbonitrile;

6-[2-Amino-4-oxo-4H-thiazol-(5Z)-ylidenemethyl]-4-tert-butylsulfanyl-quinoline-3-carbonitrile;

6-[2-Amino-4-oxo-4H-thiazol-(5Z)-ylidenemethyl]-4-isopropylsulfanyl-quinoline-3-carbonitrile;

6-[2-(R)-1-Hydroxymethyl-2-methyl-propylamino)-4-oxo-4H-thiazol-(5Z)-ylidenemethyl]-4-isopropoxy-quinoline-3-carbonitrile;

6-[2-(R)-2-Hydroxy-1-phenyl-ethylamino)-4-oxo-4H-thiazol-(5Z)-ylidenemethyl-4-isopropoxy-quinoline-3-carbonitrile;

6-[2-Amino-4-oxo-4H-thiazol-(5Z)-ylidenemethyl]-4-(2,2,2-trifluoro-ethoxy)-quinoline-3-carbonitrile;

6-[2-(2,3-Dihydroxy-propylamino)-4-oxo-4H-thiazol-(5Z)-ylidenemethyl]-4-isopropylsulfanyl-quinoline-3-carbonitrile;

6-[2-Amino-4-oxo-4H-thiazol-(5Z)-ylidenemethyl]-4-(2,2,2-trifluoro-1-trifluoromethyl-ethoxy)-quinoline-3-carbonitrile;

6-[2-Amino-4-oxo-4H-thiazol-(5Z)-ylidenemethyl]-4-isobutyl-quinoline-3-carbonitrile;

6-[2-Amino-4-oxo-4H-thiazol-(5Z)-ylidenemethyl]-4-isopropylsulfanyl-quinoline-3-carbonitrile; compound with methanesulfonic acid;

6-[2-Amino-4-oxo-4H-thiazol-(5Z)-ylidenemethyl]-4-isobutyl-quinoline-3-carbonitrile; compound with methanesulfonic acid;

6-[2-Amino-4-oxo-4H-thiazol-(5Z)-ylidenemethyl]-4-butyl-quinoline-3-carbonitrile;

6-[2-Amino-4-oxo-4H-thiazol-(5Z)-ylidenemethyl]-4-(3-hydroxy-propylsulfanyl)-quinoline-3-carbonitrile;

6-[2-Amino-4-oxo-4H-thiazol-(5Z)-ylidenemethyl]-4-[3-(tert-butyl-dimethyl-silanyloxy)-propylsulfanyl]-quinoline-3-carbonitrile;

6-[2-Amino-4-oxo-4H-thiazol-(5Z)-ylidenemethyl]-4-hexyl-quinoline-3-carbonitrile;
6-[2-Amino-4-oxo-4H-thiazol-(5Z)-ylidenemethyl]-4-butylsulfanyl-quinoline-3-carbonitrile;
6-[2-Amino-4-oxo-4H-thiazol-(5Z)-ylidenemethyl]-4-ethylsulfanyl-quinoline-3-carbonitrile;
6-[2-Amino-4-oxo-4H-thiazol-(5Z)-ylidenemethyl]-4-methylsulfanyl-quinoline-3-carbonitrile;
4-Isopropoxy-6-[4-oxo-2-[(thiophen-2-ylmethyl)-amino]-4H-thiazol-(5Z)-ylidenemethyl]-quinoline-3-carbonitrile;
6-[2-Amino-4-oxo-4H-thiazol-(5Z)-ylidenemethyl]-4-cyclopropyl-quinoline-3-carbonitrile;
6-[2-(2-Hydroxy-1-hydroxymethyl-ethylamino)-4-oxo-4H-thiazol-(5Z)-ylidenemethyl]-4-isopropoxy-quinoline-3-carbonitrile;
6-[2-Hydrazino-4-oxo-4H-thiazol-(5Z)-ylidenemethyl]-4-isopropoxy-quinoline-3-carbonitrile;
2-Amino-5-[1-(3-methanesulfonyl-4-phenyl-quinolin-6-yl)-meth-(5Z)-ylidene]-thiazol-4-one;
6-[2-Amino-4-oxo-4H-thiazol-(5Z)-ylidenemethyl]-4-phenyl-quinoline-3-carbonitrile;
6-[2-Amino-4-oxo-4H-thiazol-(5Z)-ylidenemethyl]-4-pyridin-3-yl-quinoline-3-carbonitrile; compound with trifluoro-acetic acid;
6-[2-Amino-4-oxo-4H-thiazol-(5Z)-ylidenemethyl]-4-(1-ethyl-propoxy)-quinoline-3-carbonitrile;
6-[2-Amino-4-oxo-4H-thiazol-(5Z)-ylidenemethyl]-4-isobutylsulfanyl-quinoline-3-carbonitrile;
6-[2-Amino-4-oxo-4H-thiazol-(5Z)-ylidenemethyl]-4-isobutoxy-quinoline-3-carbonitrile;
6-[2-Amino-4-oxo-4H-thiazol-(5Z)-ylidenemethyl]-4-(2,2-dimethyl-propoxy)-quinoline-3-carbonitrile;
6-[2-Cyclopropylamino-4-oxo-4H-thiazol-(5Z)-ylidenemethyl]-4-(1-ethyl-propoxy)-quinoline-3-carbonitrile;
6-[2-Cyclopropylamino-4-oxo-4H-thiazol-(5Z)-ylidenemethyl]-4-isobutoxy-quinoline-3-carbonitrile;
6-[2-Cyclopropylamino-4-oxo-4H-thiazol-(5Z)-ylidenemethyl]-4-(2,2-dimethyl-propoxy)-quinoline-3-carbonitrile;
6-[2-Amino-4-oxo-4H-thiazol-(5Z)-ylidenemethyl]-4-propyl-quinoline-3-carbonitrile;
6-[2-Amino-4-oxo-4H-thiazol-(5Z)-ylidenemethyl]-4-pentyl-quinoline-3-carbonitrile;
6-[2-Amino-4-oxo-4H-thiazol-(5Z)-ylidenemethyl]-4-methyl-quinoline-3-carbonitrile;
2-Cyclopropylamino-5-[1-(4-ethoxy-3-methanesulfonyl-quinolin-6-yl)-meth-(5Z)-ylidene]-thiazol-4-one;
2-Amino-5-[1-(4-ethoxy-3-methanesulfonyl-quinolin-6-yl)-meth-(5Z)-ylidene]-thiazol-4-one;
6-[2-Amino-4-oxo-4H-thiazol-(5Z)-ylidenemethyl]-4-(tetrahydro-pyran-4-yloxy)-quinoline-3-carbonitrile;
6-[2-Amino-4-oxo-4H-thiazol-(5Z)-ylidenemethyl]-4-(2-methoxy-ethoxy)-quinoline-3-carbonitrile;
6-[2-Cyclopropylamino-4-oxo-4H-thiazol-(5Z)-ylidenemethyl]-4-(tetrahydro-pyran-4-yloxy)-quinoline-3-carbonitrile;
4-Butoxy-6-[2-cyclopropylamino-4-oxo-4H-thiazol-(5Z)-ylidenemethyl]-quinoline-3-carbonitrile;
6-[2-Amino-4-oxo-4H-thiazol-(5Z)-ylidenemethyl]-1-4-butoxy-quinoline-3-carbonitrile and
6-[2-Cyclopropylamino-4-oxo-4H-thiazol-(5Z)-ylidenemethyl]-4-(2-methoxy-ethoxy)-quinoline-3-carbonitrile.

As used herein the halogen includes all four halogens such as chlorine, fluorine, bromine and iodine.

As used in the specification, the term "lower alkyl", alone or in combination, means a monovalent straight or branched-chain saturated hydrocarbon alkyl group containing from one to six carbon atoms, such as methyl, ethyl, n-propyl, isopropyl, n-butyl, sec-butyl, isobutyl, tert-butyl, n-pentyl, n-hexyl and the like.

The term "cycloalkyl" means a cyclolower alkyl substituent which designates a monovalent unsubstituted 3- to 6-membered saturated carbocylic hydrocarbon ring. Among the preferred cycloalkyl substituents are cyclopropyl, cyclobutyl, cyclohexyl, etc.

The term "lower alkoxy" means a straight-chain or branched-chain alkoxy group formed from lower alkyl containing from one to six carbon atoms, such as methoxy, ethoxy, n-propoxy, isopropoxy, n-butoxy, tert-butoxy and the like.

The term "aryl" means a monovalent mono- or bicyclic unsubstituted aromatic hydrocarbon ring, such as phenyl or naphthyl, with phenyl being preferred.

The term "heterocycloalkyl" refers to a 4 to 6 membered monocyclic saturated ring containing 3 to 5 carbon atoms and one or two hetero atoms selected from the group consisting of oxygen, nitrogen or sulfur. Among the preferred heterocyclic alkyl groups are included mopholinyl, tetrahydro, thiopyranyl or tetrahydro pyranyl.

The term "heteroaromatic ring" refers to a monovalent 5 or 6 membered monocyclic heteroaromatic ring containing from 4 to 5 carbon atoms and from 1 to 2 hetero atoms selected from the group consisting of oxygen, nitrogen or sulfur. Among the preferred heteroaromatic groups are included thiopenyl, thioazole, pyridinyl, furanyl, etc.

The term "lower alkylene" designates a divalent saturated straight or branch chain hydrocarbon substituent containing from one to six carbon atoms.

The term "carboxy lower alkylene" denotes a lower alkylene substituent as designated hereinbefore substituted, preferably monosubstituted, with a carboxy radical.

The term "hydroxy lower alkylene" designates a lower alkylene substituent substituted, preferably monosubstituted, with a hydroxy group. Where an amido lower alkylene is used, this designates a lower alkylene substituent as set forth hereinbefore substituted with an amido substituent.

The term "hydroxyl alkyl" designates a lower alkyl substituent substituted, preferably di- or mono-substituted, with a hydroxyl group.

The term "mono- or di-halo lower alkylene substituents" designate a lower alkylene substituent which is either monosubstituted or disubstituted on one or two carbon atoms in the lower alkylene chain.

The term "haloalkyl" designates a lower alkyl substituent mono- or di-substituted by a halogen.

The term "amino lower alkylene" designates a lower alkylene substituent which is substituted, preferably monosubstituted, with an amino group.

The term "amido lower alkylene" designates a lower alkylene substituent as hereinbefore defined substituted on one position with an amido group. The amino group on the amino lower alkylene may be substituted by 1 or 2 lower alkyl groups. In the case of one lower alkyl group substitution, the term "mono-lower alkyl amino" is used. In the case of two lower alkyl substituents on the nitrogen atom of the amine group, the substituent is a "di-lower alkyl amino group."

The term "aryloxy" designates an aryloxy substituent where aryl is as above. The preferred aryl group is phenyl and the preferred aryloxy is phenoxy.

The term "perfluoro-lower alkyl" means any lower alkyl group wherein all the hydrogens of the lower alkyl group are substituted or replaced by fluorine. Among the preferred perfluoro-lower alkyl groups are trifluoromethyl, pentafluroethyl, heptafluoropropyl, etc with trifluromethyl being especially preferred.

The term "pharmaceutically acceptable salts" refers to conventional acid-addition salts or base-addition salts that retain the biological effectiveness and properties of the compounds of formulas I, II, III, IV and V and are formed from suitable non-toxic organic or inorganic acids, or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et al., *Pharmaceutical Dosage Forms and Drug Delivery Systems* (6th Ed. 1995) at pp. 196 and 1456-1457.

In accordance with this invention, the compounds of formula I can be prepared from a compound of the formula:

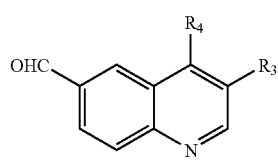

II wherein $R_3$ and $R_4$ are as above.

The compound of formula II is converted to the compound of formula I via the following reaction scheme.

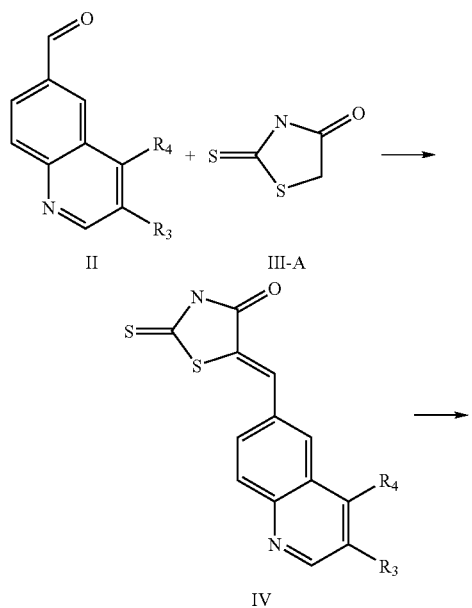

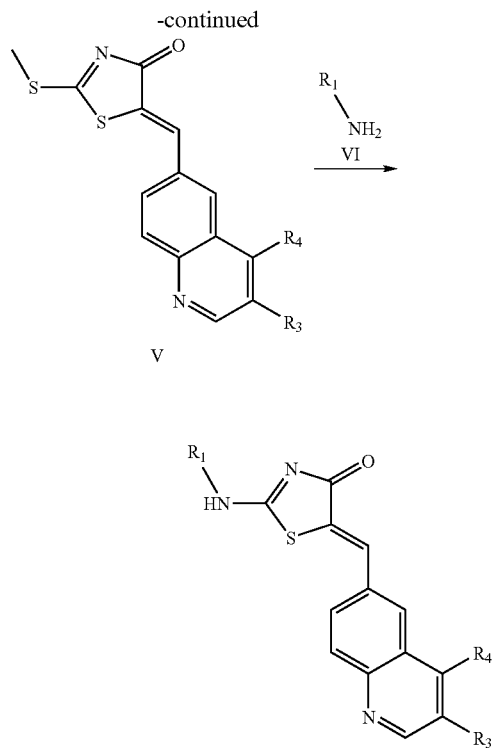

wherein $R_1$, $R_3$ and $R_4$ are as above.

In accordance with this invention, the compound of formula II is reacted with the compound of formula III-A (rhodanine (2-thioxo-thiazolin-4-one)) via a Knoevenegel reaction to produce the compound of formula IV. Any of the conditions conventional in carrying out Knoevenegel reaction can be utilized in carrying out this condensation. Generally, this reaction is carried out at reflux temperature in the presence of alkali metal acetate and acetic acid. In the next step of this synthesis, the resulting substituted thiazolidine of formula IV is treated with a methylating agent to methylate the thio group on the compound of formula IV to produce the compound of formula V. The preferred methylating agent is iodomethane. This reaction is carried out in an organic amine base such as diisopropylethylamine (DIEA). In carrying out this reaction, temperature and pressure are not critical and this reaction can be carried out at room temperature and atmospheric pressure. In fact, in carrying out this reaction, any of the conditions conventional in methylating a thio group can be used.

In the next step of this synthesis, the compound of formula V is reacted with the compound of formula VI to produce the compound of formula I. The compound of formula VI is an amine and any means conventionally used in amine substitution of methylthio group can be used in carrying out this reaction. In accordance with one embodiment, this substitution is carried out by reacting the compound of formula VI with the compound of formula V in the presence of a conventional solvent such as acetonitrile. Generally, this reaction is carried out in the presence of an amine base such as diisopropylethylamine.

On the other hand, the compound of formula I can be prepared by reacting the compound of formula II with a compound of the formula:

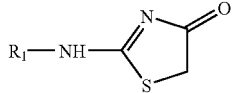

VII wherein $R_1$ is as above.

The reaction of the compound of formula VII with the compound of formula II to produce the compound of formula I, is carried out in an organic solvent such as benzene or toluene at high temperature of from 100° C. to 200° C. in a closed system. In this manner this reaction is carried out under high temperatures and pressure. The compound of formula VII can be directly formed by direct replacement thorough reacting the compound of the formula $R_1$—$NH_2$     VI wherein $R_1$ is as above with a compound of the formula III-A. The replacement reaction is generally carried out in the presence of an activator and an amine base. Among the preferred activators is mercuric chloride. This reaction is carried out in an inert organic solvent. Any conventional inert organic solvent such as acetonitrile, methylene chloride, etc. can be utilized. In carrying out this reaction, an amine base, such as diisoproprylethylamine, is used. In carrying out this reaction, temperature and pressure are not critical and this reaction can be carried out at room temperature and atmospheric pressure. In carrying out this reaction, any conventional method of replacing a mercapto group with an amine can be utilized.

In the compound of formula VI where $R_1$ is $R_2$—X— and X is a hydroxy lower alkylene, these compounds can be prepared from the corresponding amino acids or amino acid esters by reduction with an alkali metal borohydride. On the other hand, these hydroxy lower alkylene compounds can be prepared for the corresponding cyano carboxylic acid esters by reduction with lithium aluminum hydride. Reduction reduces the cyano group to an amino group and the ester to a hydroxy group. This reduction should take place before reacting the compound of formula VI with the compound of formula V.

On the other hand, where in the compound of formula $V_1$, $R_1$ is $R_2X$— and X is a carboxy lower alkylene, amido lower alkylene or imido lower alkylene, these compounds can be directly converted to the compound of formula I by reacting the corresponding compound of formula VI with the compound of formula V.

Where the rings Ⓟ or Ⓡ is an N-oxide of a nitrogen atom in a nitrogen containing ring which forms the rings Ⓟ or Ⓡ, these N-oxides can be formed from a tertiary ring nitrogen atom by oxidation. Any conventional method of oxidizing a tertiary nitrogen atom to an N-oxide can be utilized. The preferred oxidizing agent is m-chloroperbenzoic acid (MCPBA).

In accordance with this invention, the compound of formula II can be produced by the following reaction scheme:

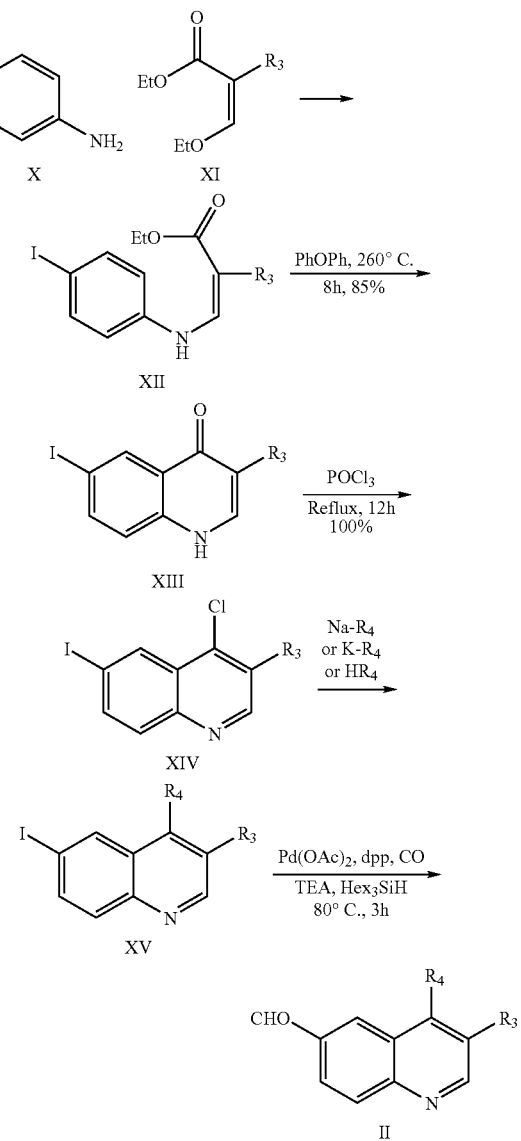

wherein $R_3$ is cyano or —C(=O)—$OR_{11}$ and $R_4$ is —O(CH$_2$CH$_2$O)$_y$—$R_{10}$,

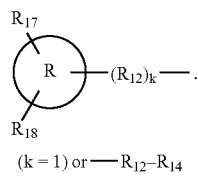

(k = 1) or —$R_{12}$–$R_{14}$

The ether ester of formula XI is condensed with iodoaniline, the compound of formula X, to produce the substituted amine of formula XII. This reaction is conventional condensation reaction wherein substitution of an alpha beta unsaturated ether by an amine is achieved by condensation of the amine with an ether. Generally this reaction is carried out at temperatures of from 80° C. to 200° C. in an inert organic solvent. Any conventional inert organic solvent can be utilized in carrying out this reaction. Among the conventional inert organic solvent solvents that can be utilized for carrying out this reaction are included toluene, benzene, etc. Generally this reaction is carried out by refluxing for long periods of time, i.e. above five hours.

The compound of formula XII is converted to the compound of formula XIII by cyclization of the compound of formula XII. This cyclization is carried out by heating compound of formula XII temperatures of at least 200° C. generally from 200° C. to 300° C. in the presence of high boiling ether such as biphenyl ether. The cyclized compound which contains an oxo group of formula XIII can be converted to the halognated compound of formula XIV by treatment with a halogenating agent such as phosphorous oxychloride. In this manner, the reaction mixture can be refluxed to convert the oxo group into a halide with good yields. Any of the conditions conventional in converting of hydroxyl group on the aromatic ring to the halogen can be used in carrying out this reaction.

If it is desired to produce the compounds of formula I wherein $R_4$ is a substitution —O(CH2CH2O)y-R10,

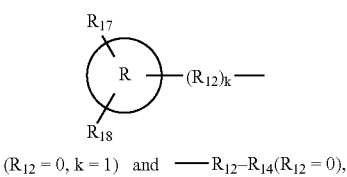

$(R_{12} = O, k = 1)$ and —$R_{12}$–$R_{14}$($R_{12} = O$), the compound of formula XIV is converted to the compound of formula XV by reacting the halogenated site of the compound of formula XIV with a sodium salt or potassium salt of the $R_4$ substituent one wishes to place at the 4-position of the compound of formula I. This reaction is carried out by heating the salt and the compound of formula XIV under high pressure in their corresponding alcohol solvent medium. Any conventional method of reacting a chlorine group with a sodium salt or potassium salt can be utilized to carry out this reaction.

If it is desired to produce the compounds of formula I wherein $R_4$ is

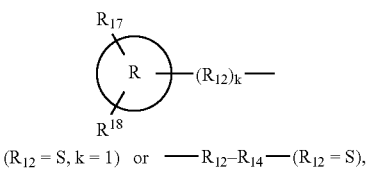

$(R_{12} = S, k = 1)$ or —$R_{12}$–$R_{14}$—($R_{12} = S$), the compound of formula XIV is converted to the compound of formula XV by reacting the halogenated site of the compound of formula XIV with a corresponding thiol of the formula HS—R. This reaction is carried out under a base at room temperature. Any conventional method of substitution of halogen group with thiol group can be utilized to effect this conversion.

In the last step of this synthesis, the compound of formula XV is converted to the compound of formula II using formylation reaction to convert the iodo group to the CHO group on the phenyl ring. This reaction can be carried out by reacting the compound of formula XV with carbon monoxide under pressure in the presence of diphenylpropyl phosphine (dpp) in the presence of a base utilizing palladium acetate as catalyst at temperature of from 40° C. to 120° C. Pressures generally from 50 to 80 psi are utilized in carrying out this reaction. Any conventional method of formylation reaction to convert a halide group on a phenyl ring by the means of reaction with carbon monoxide can be utilized to convert the compound of formula XV to the compound of formula II.

Or the compound of formula II can be produced by the following reaction scheme if it is desired to produce the compounds of formula I wherein $R_4$ is an lower alkyl or

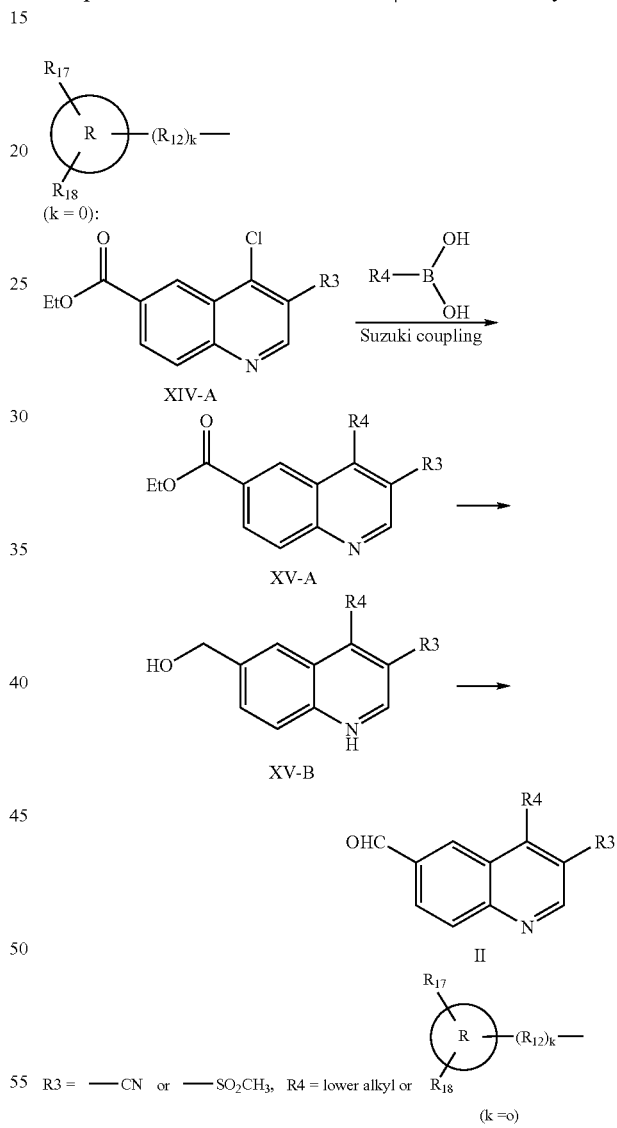

The chloro compound of formula XIV-A (synthesized as in example 46c when $R_3$=—CN or in example 61f when $R_3$=—SO$_2$CH$_3$) is converted to the compound of formula XV-A using Suzuki coupling with $R_4$ boronic acid. This C—C bond formation reaction can be carried out utilizing a palladium catalyst with a base at temperature from 50° C. to 200° C. Any conventional method of formation of C—C bond can be utilized to convert the compound of formula XIV-A to the compound of formula XV-A.

The compound of formula XV-A is converted to the compound of formula XV-B by reducing the ester group in the compound of formula XV-A to alcohol. In this reaction, quinoline ring is reduced to dihydydro-quinoline ring at the meantime. Generally it is preferred to use lithium borohydride as reducing agent. Any conventional method for reduction of ester can be utilized to effect this conversion.

The compound of formula XV-B is converted to the compound of formula II by oxidizing the alcohol group in the compound of formula XV-B to aldehyde. Any conventional method for oxidation of alcohol to aldehyde such as manganese dioxide can be utilized to effect this conversion.

In accordance under another embodiment where $R_3$ in the compound of formula XV is

the compound of formula:

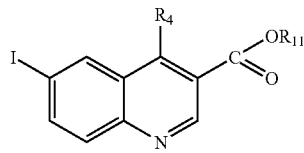

XV-A where $R_4$ and $R_{11}$ are as above.

This compound can be converted to the compound of the formula

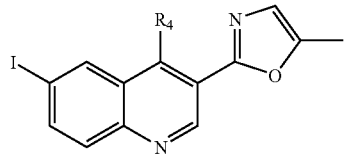

XV-B by reacting the compound of XV-A with an amine of formula

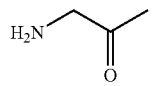

XXX to produce amide of formula

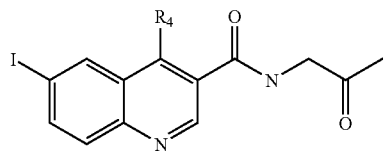

XVI

Any conventional method of reacting an amine with a carboxylic acid or ester thereof can be used in reacting the amine with the acid or ester of formula XV-A to form the amide of formula XVI. The amide of formula XVI is converted to the compound of XV-B by means of a cyclization reaction. This cyclization is carried out by utilizing Burgess Reagent ((methoxycarbonylsulfamoyl)triethylammonium hydroxide, inner salt) under a microwave. In this manner the compound of formula XV-B is produced. This compound can be formylated to produce the compound of formula II where $R_3$ is

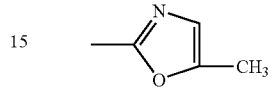

and the corresponding compound of formulae I-A and I-B where $R_3$ is this substituent.

This compound XV-A can be converted to the compound of the formula

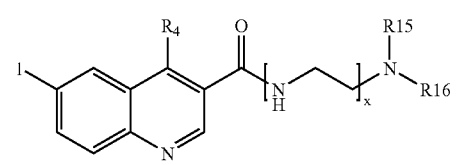

XV-C by reacting the compound of XV-A with an amine of formula

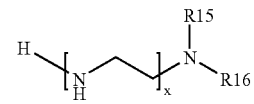

XXX-A to produce amide of formula XV-C

Any conventional method of reacting an amine with a carboxylic acid or ester thereof can be used in reacting the amine with the acid or ester of formula XV-A to form the amide of formula XV-C. This compound can be formylated to produce the compound of formula II where $R_3$ is

and the corresponding compound of formulae I-A and I-B where $R_3$ is this substituent.

Pharmaceutical compositions according to the invention may, alternatively or in addition to a compound of Formula I, comprise as an active ingredient pharmaceutically acceptable prodrugs, pharmaceutically active metabolites, and pharmaceutically acceptable salts of such compounds and metabolites. Such compounds, prodrugs, multimers, salts, and metabolites are sometimes referred to herein collectively as "active agents" or "agents."

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the active agents of the invention may be used to treat diseases mediated by modulation or regulation of the protein kinases CDK1. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of CDK1 protein kinase includes: preventing the disease condition from occurring in a mammal, particularly when the mammal is found to be predisposed to having the disease condition but has not yet been diagnosed as having it; modulating and/or inhibiting the disease condition; and/or alleviating the disease condition. The present invention is further directed to methods of modulating or inhibiting protein kinase CDK1 activity, for example in mammalian tissue, by administering the inventive agent. The activity of agents as anti-proliferatives is easily measured by known methods, for example by using whole cell cultures in an MTT assay. The activity of the inventive agents as modulators of CDK1 protein kinase activity may be measured by any of the methods available to those skilled in the art, including in vivo and/or in vitro assays. Examples of suitable assays for activity measurements include those described in International Publication No. WO 99/21845; Parast et al., Biochemistry, 37, 16788-16801 (1998); Connell-Crowley and Harpes, Cell Cycle: Materials and Methods, (Michele Pagano, ed. Springer, Berlin, Germany) (1995); International Publication No. WO 97/34876; and International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of formula I and an inert, pharmaceutically acceptable carrier or diluent. In one embodiment of the pharmaceutical compositions, efficacious levels of the inventive agents are provided so as to provide therapeutic benefits involving anti-proliferative ability. By "efficacious levels" is meant levels in which proliferation is inhibited, or controlled. These compositions are prepared in unit-dosage form appropriate for the mode of administration, e.g., parenteral or oral administration.

An inventive agent can be administered in conventional dosage form prepared by combining a therapeutically effective amount of an agent (e.g., a compound of formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methyl methacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent can be dissolved in an aqueous solution of an organic or inorganic acid. If a soluble salt form is not available, the agent may be dissolved in a suitable cosolvent or combinations of cosolvents.

It will be appreciated that the actual dosages of the agents used in the compositions of this invention will vary according to the particular complex being used, the particular composition formulated, the mode of administration and the particular site, host and disease being treated. Optimal dosages for a given, set of conditions can be ascertained by those skilled in the art using conventional dosage determination tests in view of the experimental data for an agent.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores.

EXAMPLES

Example 1

4-Methoxy-6-[4-oxo-2-((1R,2S)-2-phenyl-cyclopropylamino)-4H-thiazol-(5Z)-ylidenemethyl]-quinoline-3-carboxylic acid methyl ester

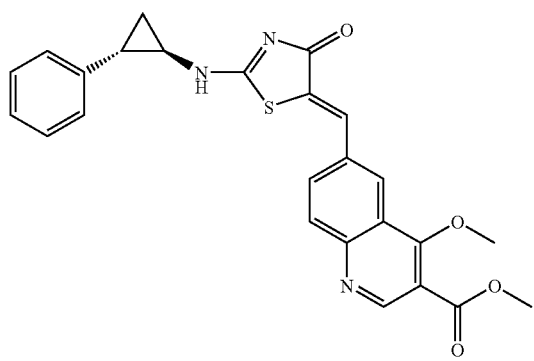

a) Preparation of 2-[(4-iodo-phenylamino)-methylene]-malonic acid diethyl ester

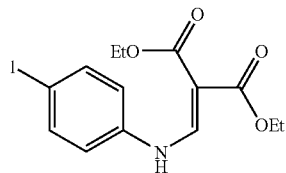

A mixture of 4-iodoaniline (50 g, 0.23 mol) and diethyl ethoxymethylenemalonate (50.3 g, 0.23 mmol) was stirred at 90° C. for 10 hours. 150 mL of ethanol was added and the mixture was refluxed for 3 h. After cooling, the solid was collected, washed with hexane and dried over the oven to obtain 2-[(4-iodo-phenylamino)-methylene]-malonic acid diethyl ester (81 g, 91%) as a white solid.

b) Preparation of 6-iodo-4-oxo-1,4-dihydro-quinoline-3-carboxylic acid ethyl ester

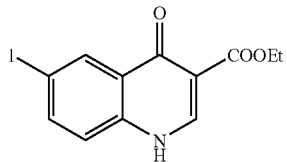

A mixture of 2-[(4-iodo-phenylamino)-methylene]-malonic acid diethyl ester (81 g, 0.21 mol) in diphenylether (60 mL) was refluxed at 240° C. for 14 h. After cooling, ethanol was added and the mixture was heated to reflux for 3 h. After cooling, the solid was collected by filtration, washed with hexane and dried to obtain 6-iodo-4-oxo-1,4-dihydro-quinoline-3-carboxylic acid ethyl ester (59 g, 83%) as a yellow solid.

c) Preparation of 4-chloro-6-iodo-quinoline-3-carboxylic acid ethyl ester

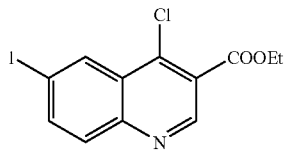

A mixture of 6-iodo-4-oxo-1,4-dihydro-quinoline-3-carboxylic acid ethyl ester (56 g, 0.16 mol) in phosphorus oxychloride (180 mL) was refluxed under $N_2$ for 14 h. After cooling, the solvent was removed by rotary evaporator and then by the oil pump. Sat. sodium bicarbonate (200 mL) was slowly added. The solid was collected by filtration, washed with sat. sodium bicarbonate, water and dried to obtain 4-chloro-6-iodo-quinoline-3-carboxylic acid ethyl ester (58 g, 98%) as a yellow solid.

d) Preparation of 6-iodo-4-methoxy-quinoline-3-carboxylic acid methyl ester

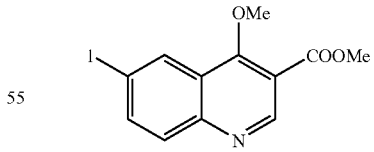

To the suspension of 4-chloro-6-iodo-quinoline-3-carboxylic acid ethyl ester (14 g, 0.039 mol) in anhydrous methanol (180 mL) was added sodium methoxide (4.16 g, 0.07 mol). The mixture was heated to 100° C. under a pressure tube and stirred for 10 h. After cooling to room temperature, the ice water was added. The solid was collected by filtration, washed with water and dried to obtain 6-iodo-4-methoxy-quinoline-3-carboxylic acid methyl ester (12 g, 92%) as a yellow solid. LC-MS m/e 344 (MH$^+$)

e) Preparation of 6-formyl-4-methoxy-quinoline-3-carboxylic acid methyl ester

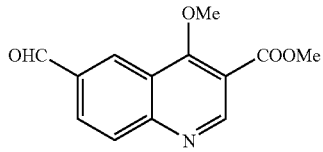

A mixture of 6-iodo-4-methoxy-quinoline-3-carboxylic acid methyl ester (example 1d) (1.37 g, 4 mmol), triethylamine (1.4 mL, 10 mmol), diphenylpropylphosphine (dpp, 45 uL, 0.2 mmol) and palladium(II) acetate (45 mg, 0.2 mmol) in dry N,N-dimethylformamide (30 mL) in pressure tube was stirred under carbon monoxide at 75 psi at room temperature for 10 min. After addition of trihexylsilane (2.8 mL, 8 mmol), the mixture was then stirred under carbon monoxide at 75 psi at 80° C. for 3 h. The reaction was allowed to cool to 25° C. and then extracted with methylene chloride (2×100 mL). The combined organic layers were successively washed with a saturated aqueous sodium bicarbonate solution (3×50 mL) and water (3×50 mL), dried over sodium sulfate, filtered, and concentrated in vacuo. Flash chromatography (Merck Silica gel 60, 70-230 mesh, 0%-40% ethyl acetate in hexanes in 30 min) afforded 6-formyl-4-methoxy-quinoline-3-carboxylic acid methyl ester (0.48 g, 50%) as a white solid.

f) Preparation of 2-((1R,2S)-2-phenyl-cyclopropylamino)-thiazol-4-one

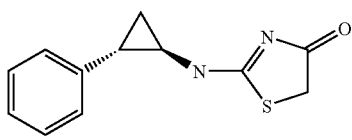

To a suspension of (1R,2S)-2-phenyl-cyclopropylamine hydrochloride (0.8 µg, 5 mmol) and rhodanine (2-thioxo-thiazolin-4-one) (0.68 g, 5 mmol) in acetonitrile (20 mL) was added DIEA (diisopropylethylamine) (2.61 mL, 15 mmol) at room temperature. Then, this solution was cooled to 0° C. and mercuric chloride (1.35 g, 5 mmol) was added in two portions within a period of 10 min. After addition, the suspension was allowed to warm to room temperature and stirred for 2 days. The resulting black solids were filtered through a plug of celite and washed with ethyl acetate (500 mL). The filtrates were removed under the vacuum and the crude residue was diluted with water (100 mL) and ethyl acetate (100 mL). The two layers were separated and the aqueous layer was extracted with ethyl acetate (2×100 mL). The combined organic extracts were washed with brine solution and dried over anhydrous magnesium sulfate. Filtration of the drying agent and removal of the solvent under the vacuum gave the crude residue which was purified by using a Biotage silica gel column chromatography to obtain 0.474 g (42% yield) of 2-((1R,2S)-2-phenyl-cyclopropylamino)-thiazol-4-one as a white amorphous solid: EI-HRMS m/e calcd for $C_{12}H_{12}N_2OS$ (M+) 232.0670, found 232.0665.

g) Preparation of 4-methoxy-6-[4-oxo-2-((1R,2S)-2-phenyl-cyclopropylamino)-4H-thiazol-(5Z)-ylidenemethyl]-quinoline-3-carboxylic acid methyl ester

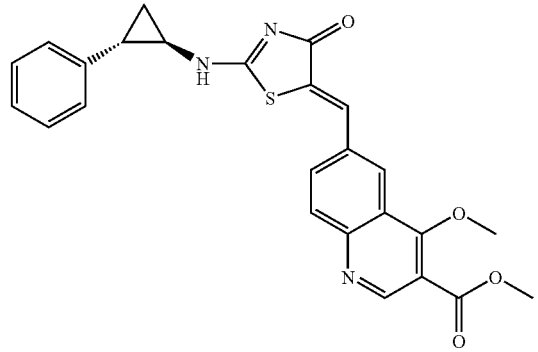

To the suspension of 6-formyl-4-methoxy-quinoline-3-carboxylic acid methyl ester (example 1e, 100 mg, 0.4 mmol), 2-((1R,2S)-2-phenyl-cyclopropylamino)-thiazol-4-one (example 1f, 93 mg, 0.4 mmol) and benzoic acid (5 mg, 0.04 mmol) in toluene (2 mL) were added and piperidine (5 uL, 0.04 mmol). The mixture was heated to 150° C. by microwave for 20 min. After cooling to room temperature, the solid was collected by filtration, washed with toluene and dried. Flash chromatography (Merck Silica gel 60, 70-230 mesh, 0%-10% methanol in methylene chloride in 30 min) afford 4-methoxy-6-[4-oxo-2-((1R,2S)-2-phenyl-cyclopropylamino)-4H-thiazol-(5Z)-ylidenemethyl]-quinoline-3-carboxylic acid methyl ester (55 mg, 30%) as a light yellow solid. LC-MS m/e 460 (MH+).

Example 2

4-Methoxy-6-[4-oxo-2-((1R,2S)-2-phenyl-cyclopropylamino)-4H-thiazol-(5Z)-ylidenemethyl]-quinoline-3-carboxylic acid amide

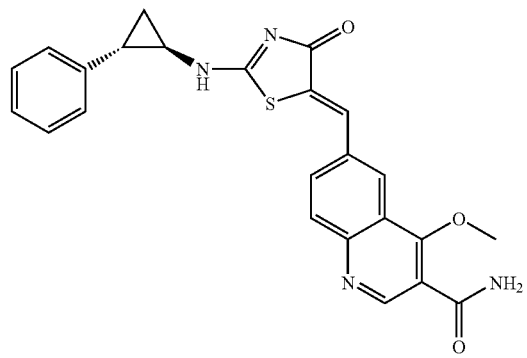

a) Preparation of 6-iodo-4-methoxy-quinoline-3-carboxylic acid amide

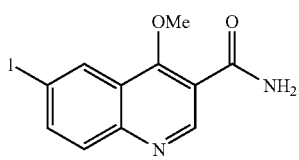

A suspension of 6-iodo-4-methoxy-quinoline-3-carboxylic acid methyl ester (example 1d) (1.7 g, 5 mmol) in ammonium hydroxide (28%, 75 mL) was heated at 150° C. for 4 days under pressure tube. After cooling, the solvent was removed by rotary evaporator. The solid was collected by filtration, washed with water and dried to obtain 6-iodo-4-methoxy-quinoline-3-carboxylic acid amide (1.4 g, 88%) as a black solid. LC-MS m/e 329 (MH$^+$).

b) Preparation of 6-formyl-4-methoxy-quinoline-3-carboxylic acid amide

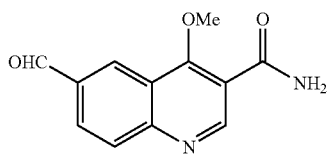

A mixture of 6-iodo-4-methoxy-quinoline-3-carboxylic acid amide (example 1d) (1.3 g, 4 mmol), triethylamine (1.4 mL, 3.5 mmol), diphenylpropylphosphine (dpp, 45 uL, 0.2 mmol) and palladium(II) acetate (45 mg, 0.2 mmol) in dry N,N-dimethylformamide (30 mL) in pressure tube was stirred under carbon monoxide at 75 psi at room temperature for 10 min. After addition of trihexylsilane (0.2.9 mL, 8 mmol), the mixture was then stirred under carbon monoxide at 75 psi at 80° C. for 4 h. The reaction was allowed to cool to 25° C. and then extracted with methylene chloride (2×150 mL). The combined organic layers were successively washed with water (3×50 mL), dried over sodium sulfate, filtered, and concentrated in vacuo. Flash chromatography (Merck Silica gel 60, 70-230 mesh, 20%-100% ethyl acetate in hexanes in 30 min) afforded 6-formyl-4-methoxy-quinoline-3-carboxylic acid amide (0.58 g, 64%) as a light yellow solid.

c) Preparation of 4-methoxy-6-[4-oxo-2-((1R,2S)-2-phenyl-cyclopropylamino)-4H-thiazol-(5Z)-ylidenemethyl]-quinoline-3-carboxylic acid amide

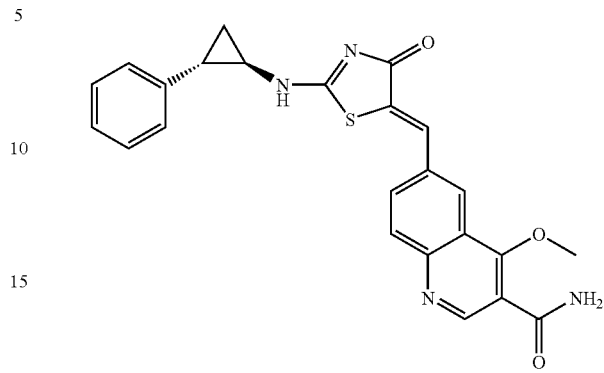

Similar procedure as described in example 1g was used, starting from 6-formyl-4-methoxy-quinoline-3-carboxylic acid amide (example 2b) and 2-((1R,2S)-2-phenyl-cyclopropylamino)-thiazol-4-one (example 1f) to give 4-methoxy-6-[4-oxo-2-((1R,2S)-2-phenyl-cyclopropylamino)-4H-thiazol-(5Z)-ylidenemethyl]-quinoline-3-carboxylic acid amide. LC-MS m/e 445 (MH$^+$).

Example 3

6-[2-((R)-1-Hydroxymethyl-2-phenyl-ethylamino)-4-oxo-4H-thiazol-(5Z)-ylidenemethyl]-4-methoxy-quinoline-3-carboxylic acid amide trifluoro-acetic acid salt

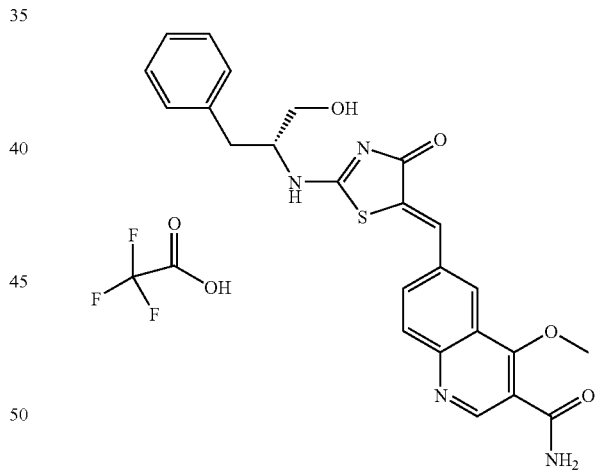

a) Preparation of 2-(1-hydroxymethyl-2-phenyl-ethylamino)-thiazol-4-one

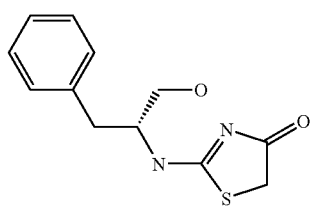

Similar procedure as described in example 1f was used, starting (R)-1-hydroxymethyl-2-phenyl-ethylamine, rhodanine (2-thioxo-thiazolin-4-one) and DIEA (diisopropyl-ethyl-amine) to give 2-(1-hydroxymethyl-2-phenyl-ethylamino)-thiazol-4-one. LC-MS m/e 251 (MH+).

c) Preparation of 6-[2-((R)-1-hydroxymethyl-2-phenyl-ethylamino)-4-oxo-4H-thiazol-(5Z)-ylidenemethyl]-4-methoxy-quinoline-3-carboxylic acid amide trifluoro-acetic acid salt Similar procedure as described in example 1g was used, starting from 6-formyl-4-methoxy-quinoline-3-carboxylic acid amide (example 2b) and 2-(1-Hydroxymethyl-2-phenyl-ethylamino)-thiazol-4-one (example 3a). HPLC (Reverse C18, 10%-90% acetonitrile (0.1% TFA) in water in 10 min) gave 6-[2-((R)-1-hydroxymethyl-2-phenyl-ethylamino)-4-oxo-4H-thiazol-(5Z)-ylidenemethyl]-4-methoxy-quinoline-3-carboxylic acid amide trifluoro-acetic acid salt. LC-MS m/e 463 (MH+).

Example 4

6-[2-((R)-2-Hydroxy-1-phenyl-ethylamino)-4-oxo-4H-thiazol-(5Z)-ylidenemethyl]-4-methoxy-quinoline-3-carboxylic acid amide

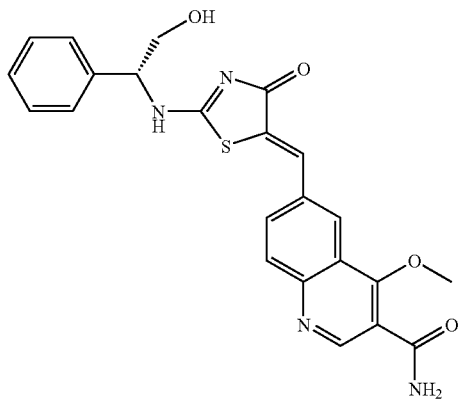

a) Preparation of 2-((R)-2-hydroxy-1-phenyl-ethylamino)-thiazol-4-one

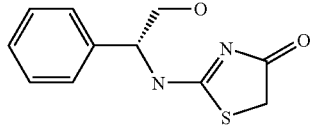

Similar procedure as described in example 1f was used, starting (R)-1-hydroxymethyl-2-phenyl-ethylamine, rhodanine (2-thioxo-thiazolin-4-one) and DIEA to give 2-((R)-2-hydroxy-1-phenyl-ethylamino)-thiazol-4-one. LC-MS m/e 251 (MH+).

b) Preparation of 6-[2-((R)-2-hydroxy-1-phenyl-ethylamino)-4-oxo-4H-thiazol-(5Z)-ylidenemethyl]-4-methoxy-quinoline-3-carboxylic acid amide Similar procedure as described in example 1g was used, starting from 6-formyl-4-methoxy-quinoline-3-carboxylic acid amide (example 2b) and 2-((R)-2-hydroxy-1-phenyl-ethylamino)-thiazol-4-one (example 3a) to give 6-[2-((R)-2-hydroxy-1-phenyl-ethylamino)-4-oxo-4H-thiazol-(5Z)-ylidenemethyl]-4-methoxy-quinoline-3-carboxylic acid amide. LC-MS m/e 449 (MH+).

Example 5

6-[2-((R)-2-Hydroxy-1-phenyl-ethylamino)-4-oxo-4H-thiazol-(5Z)-ylidenemethyl]-4-methoxy-quinoline-3-carboxylic acid methyl ester

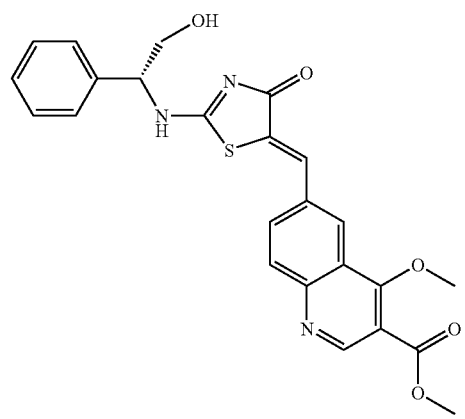

Similar procedure as described in example 1g was used, starting from 6-formyl-4-methoxy-quinoline-3-carboxylic acid methyl ester (example 1e) and 2-((R)-2-hydroxy-1-phenyl-ethylamino)-thiazol-4-one (example 3a) to give 6-[2-((R)-2-hydroxy-1-phenyl-ethylamino)-4-oxo-4H-thiazol-(5Z)-ylidenemethyl]-4-methoxy-quinoline-3-carboxylic acid methyl ester. LC-MS m/e 464 (MH+).

Example 6

4-Methoxy-6-[4-oxo-2-((1R,2S)-2-phenyl-cyclopropylamino)-4H-thiazol-(5Z)-ylidenemethyl]-quinoline-3-carboxylic acid

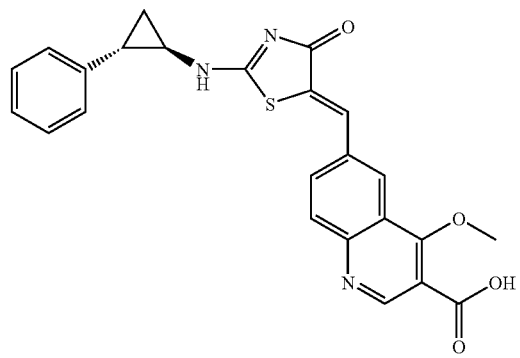

To the suspension of 4-methoxy-6-[4-oxo-2-((1R,2S)-2-phenyl-cyclopropylamino)-4H-thiazol-(5Z)-ylidenemethyl]-quinoline-3-carboxylic acid methyl ester (example 1) (50 mg, 0.11 mmol) in methanol (2 mL) was added 1 N aqueous sodium hydroxide solution (0.5 mL, 0.5 mmol). After stirring for 12 hours, the crude product was purified by HPLC (reverse C18, 10%-90% acetonitrile in water in 10 min) to afford 4-methoxy-6-[4-oxo-2-((1R,2S)-2-phenyl-cyclopropylamino)-4H-thiazol-(5Z)-ylidenemethyl]-quinoline-3-carboxylic acid. LC-MS m/e 446 (MH$^+$).

Example 7

6-[2-((R)-2-Hydroxy-1-phenyl-ethylamino)-4-oxo-4H-thiazol-(5Z)-ylidenemethyl]-4-methoxy-quinoline-3-carboxylic acid

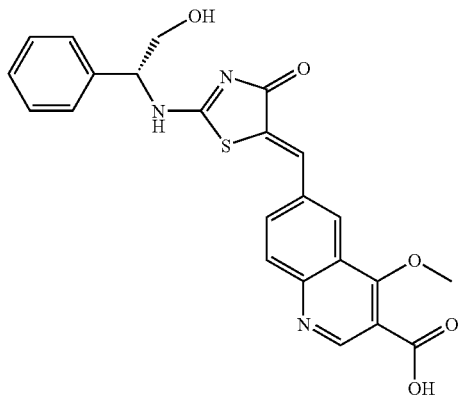

Similar procedure as described in example 5 was used, starting from 6-[2-((R)-2-hydroxy-1-phenyl-ethylamino)-4-oxo-4H-thiazol-(5Z)-ylidenemethyl]-4-methoxy-quinoline-3-carboxylic acid methyl ester (example 5) to give 6-[2-((R)-2-hydroxy-1-phenyl-ethylamino)-4-oxo-4H-thiazol-(5Z)-ylidenemethyl]-4-methoxy-quinoline-3-carboxylic acid. LC-MS m/e 450 (MH$^+$).

Example 8

4-Methoxy-6-[4-oxo-2-((1R,2S)-2-phenyl-cyclopropylamino)-4H-thiazol-(5Z)-ylidenemethyl]-quinoline-3-carboxylic acid (2-dimethylamino-ethyl)-amide; hydrochloride

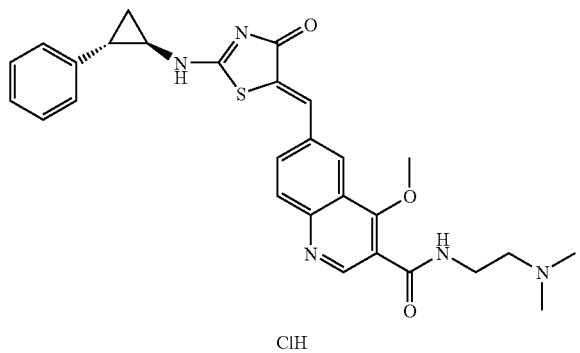

To the suspension of 4-methoxy-6-[4-oxo-2-((1R,2S)-2-phenyl-cyclopropylamino)-4H-thiazol-(5Z)-ylidenemethyl]-quinoline-3-carboxylic acid methyl ester (example 1) (50 mg, 0.11 mmol) in chloroform (5 mL) was added dimethylethylenediamine (0.048 mL, 0.44 mmol). The mixture was stirring at 120° C. for 3 h. After cooling, the solid was collected by filtration and washed with methylenechloride. The solid was dissolved in acetonitrile and 1N hydrochloride acid (0.22 mL, 0.22 mmol) was added. The resulting solution was lyophilized to give 4-methoxy-6-[4-oxo-2-((1R,2S)-2-phenyl-cyclopropylamino)-4H-thiazol-(5Z)-ylidenemethyl]-quinoline-3-carboxylic acid (2-dimethylamino-ethyl)-amide; hydrochloride. LC-MS m/e 516 (MH$^+$).

Example 9

4-Ethoxy-6-[4-oxo-2-((1R,2S)-2-phenyl-cyclopropylamino)-4H-thiazol-(5Z)-ylidenemethyl]-quinoline-3-carboxylic acid ethyl ester

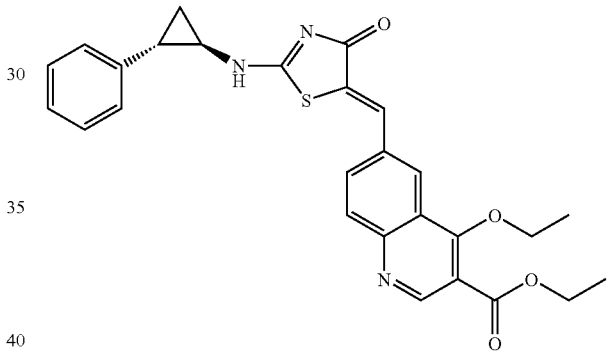

a) Preparation of 6-iodo-4-ethoxy-quinoline-3-carboxylic acid ethyl ester

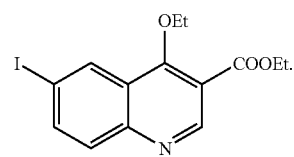

To the suspension of 4-chloro-6-iodo-quinoline-3-carboxylic acid ethyl ester (example 1c, 1.5 g, 4.1 mmol) in anhydrous ethanol (25 mL) was added sodium ethoxide (0.7 g, 10.3 mol). The mixture was heated to 100° C. under a pressure tube and stirred for 4 h. After cooling to room temperature, the ice water was added. The solid was collected by filtration, washed with water and dried to obtain 6-iodo-4-ethoxy-quinoline-3-carboxylic acid ethyl ester (0.58 g, 38%) as a yellow solid. LC-MS m/e 372 (MH$^+$)

b) Preparation of 6-formyl-4-ethoxy-quinoline-3-carboxylic acid ethyl ester

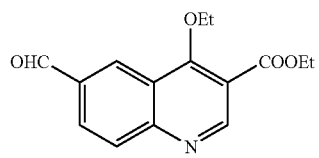

A mixture of 6-iodo-4-ethoxy-quinoline-3-carboxylic acid ethyl ester (example 9a) (0.58 g, 1.56 mmol), triethylamine (0.54 mL, 3.91 mmol), diphenylpropylphosphine (dpp, 36 uL, 0.16 mmol) and palladium(II) acetate (35 mg, 0.16 mmol) in dry N,N-dimethylformamide (16 mL) in pressure tube was stirred under carbon monoxide at 75 psi at room temperature for 10 min. After addition of trihexylsilane (1.11 mL, 3.13 mmol), the mixture was then stirred under carbon monoxide at 75 psi at 80° C. for 3 h. The reaction was allowed to cool to 25° C. and then extracted with methylene chloride (2×100 mL). The combined organic layers were successively washed with a saturated aqueous sodium bicarbonate solution (3×50 mL) and water (3×50 mL), dried over sodium sulfate, filtered, and concentrated in vacuo. Flash chromatography (Merck Silica gel 60, 70-230 mesh, 0%-40% ethyl acetate in hexanes in 30 min) afforded 6-formyl-4-ethoxy-quinoline-3-carboxylic acid ethyl ester (0.25 g, 59%) as a white solid.

c) Preparation of 4-ethoxy-6-[4-oxo-2-((1R,2S)-2-phenyl-cyclopropylamino)-4H-thiazol-(5Z)-ylidenemethyl]-quinoline-3-carboxylic acid ethyl ester

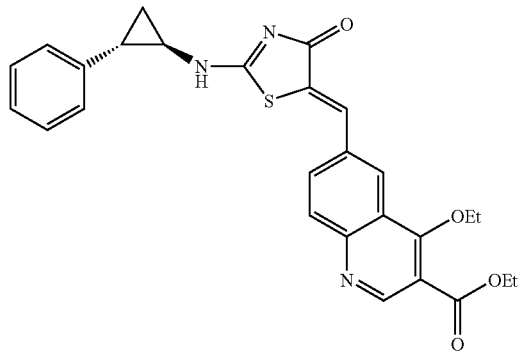

Similar procedure as described in example 1g was used, starting from 6-formyl-4-ethoxy-quinoline-3-carboxylic acid ethyl ester (example 9b) and 2-((1R,2S)-2-phenyl-cyclopropylamino)-thiazol-4-one (example 1f) to give 4-ethoxy-6-[4-oxo-2-((1R,2S)-2-phenyl-cyclopropylamino)-4H-thiazol-(5Z)-ylidenemethyl]-quinoline-3-carboxylic acid ethyl ester. LC-MS m/e 488 (MH$^+$).

Example 10

4-Methoxy-6-[4-oxo-2-((1R,2S)-2-phenyl-cyclopropylamino)-4H-thiazol-(5Z)-ylidenemethyl]-quinoline-3-carboxylic acid dimethylamide

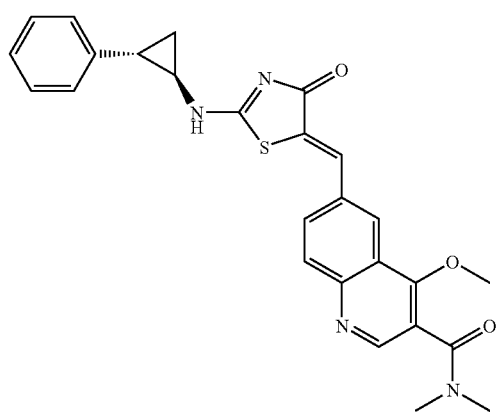

a) Preparation of 6-formyl-4-methoxy-quinoline-3-carboxylic acid

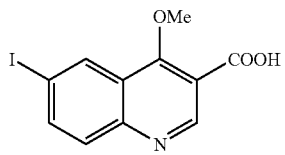

To the suspension of 6-iodo-4-methoxy-quinoline-3-carboxylic acid methyl ester (example 1d) (5.91 g, 17.2 mmol) in methanol (20 mL) was slowly added the solution of sodium hydroxide (2.76 g, 69 mmol) in water (10 mL). The mixture was stirred at room temperature for 3 hours. The solution was adjusted pH=5.0 using aqueous acetic acid solution. After adding more water, the solid was collected by filtration, washed with water and dried to obtain 6-formyl-4-methoxy-quinoline-3-carboxylic acid. LC-MS m/e 330 (MH$^+$)

b) Preparation of 6-iodo-4-methoxy-quinoline-3-carboxylic acid dimethylamide

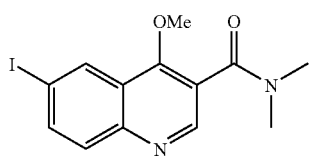

To the mixture of 6-iodo-4-methoxy-quinoline-3-carboxylic acid (example 1b) (1.5 g, 4.56 mmol), 2 M dimethylamine in THF (tetrahydrofuran) (9.11 mL, 18.2 mmol), HOBt (0.74 g, 5.5 mmol) and DIEA (diisopropylethylamine) (2.38 mL, 13.7 mmol) in DMF (N,N-dimethylformamide)

(40 mL) was slowly added the solution of O-benzotriazol-1-yl-N,N,N',N'-tetramethyluronium hexafluorophosphate (HBTU) (2.08 g, 5.47 mmol) in DMF (10 mL). After stirring at room temperature for 3 hours, the product was extracted with methylene chloride (2×100 mL). The combined organic layers were successively washed with a saturated aqueous sodium bicarbonate solution (3×50 mL) and water (3×50 mL), dried over sodium sulfate, filtered, and concentrated in vacuo. Flash chromatography (Merck Silica gel 60, 70-230 mesh, using ethyl acetate as eluant) afforded 6-iodo-4-methoxy-quinoline-3-carboxylic acid dimethylamide (1.27 g, 78%) as a solid. LC-MS m/e 357 (MH$^+$).

c) Preparation of 6-formyl-4-methoxy-quinoline-3-carboxylic acid dimethylamide

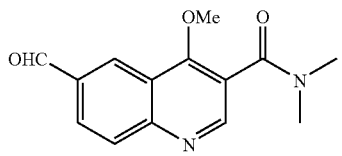

A mixture of 6-iodo-4-methoxy-quinoline-3-carboxylic acid dimethylamide (example 10b) (1.27 g, 3.57 mmol), trethylamine (1.23 mL, 8.93 mmol), diphenylpropylphosphine (dpp, 81 uL, 0.36 mmol) and palladium(II) acetate (80 mg, 0.36 mmol) in dry N,N-dimethylformamide (20 mL) in pressure tube was stirred under carbon monoxide at 75 psi at room temperature for 10 min. After addition of trihexylsilane (2.54 mL, 7.14 mmol), the mixture was then stirred under carbon monoxide at 75 psi at 80° C. for 3 h. The reaction was allowed to cool to 25° C. and then extracted with methylene chloride (2×100 mL). The combined organic layers were successively washed with a saturated aqueous sodium bicarbonate solution (3×50 mL) and water (3×50 mL), dried over sodium sulfate, filtered, and concentrated in vacuo. Flash chromatography (Merck Silica gel 60, 70-230 mesh, 0%-40% ethyl acetate in hexanes in 30 min) afforded 6-formyl-4-methoxy-quinoline-3-carboxylic acid dimethylamide as a white solid. LC-MS m/e 259 (MH$^+$).

d) Preparation of 4-methoxy-6-[4-oxo-2-((1R,2S)-2-phenyl-cyclopropylamino)-4H-thiazol-(5Z)-ylidenemethyl]-quinoline-3-carboxylic acid dimethylamide

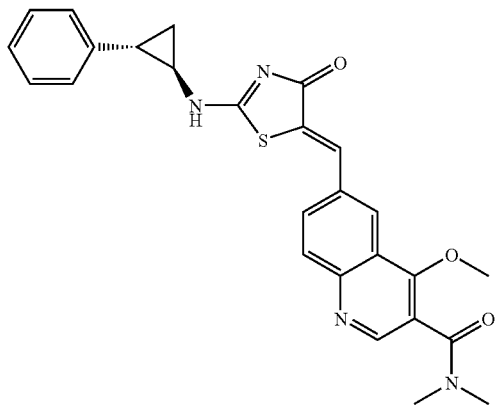

Similar procedure as described in example 1g was used, starting from 6-formyl-4-methoxy-quinoline-3-carboxylic acid dimethylamide (example 9c) and 2-((1R,2S)-2-phenyl-cyclopropylamino)-thiazol-4-one (example 1f) to give 4-methoxy-6-[4-oxo-2-((1R,2S)-2-phenyl-cyclopropylamino)-4H-thiazol-(5Z)-ylidenemethyl]-quinoline-3-carboxylic acid dimethylamide. LC-MS m/e 473 (MH$^+$).

Example 11

4-Methoxy-6-[4-oxo-2-((1R,2S)-2-phenyl-cyclopropylamino)-4H-thiazol-(5Z)-ylidenemethyl]-quinoline-3-carboxylic acid methyl ester hydrochloric salt

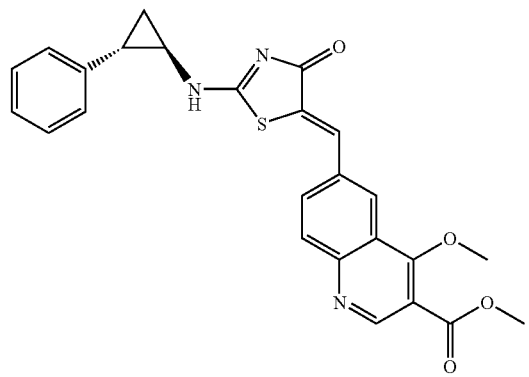

To the solution of 4-methoxy-6-[4-oxo-2-((1R,2S)-2-phenyl-cyclopropylamino)-4H-thiazol-(5Z)-ylidenemethyl]-quinoline-3-carboxylic acid methyl ester (example 1, 20 mg) acetonitrile and water was added 1 N HCl aqueous solution. The solution was lyophilized from to give 4-methoxy-6-[4-oxo-2-((1R,2S)-2-phenyl-cyclopropylamino)-4H-thiazol-(5Z)-ylidenemethyl]-quinoline-3-carboxylic acid methyl ester hydrochloric salt. LC-MS m/e 460 (MH$^+$).

Example 12

4-Ethoxy-6-[4-oxo-2-((1R,2S)-2-phenyl-cyclopropylamino)-4H-thiazol-(5Z)-ylidenemethyl]-quinoline-3-carbonitrile

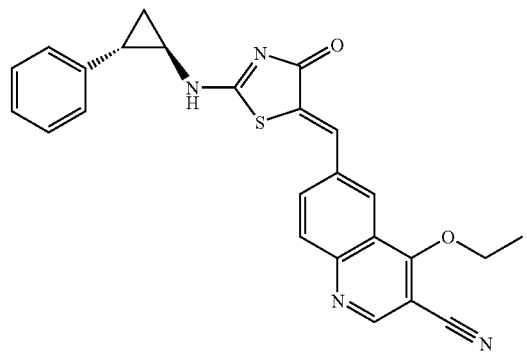

To the suspension of 4-ethoxy-6-formyl-quinoline-3-carbonitrile (example 14e) (68 mg, 0.3 mmol) and 2-((1R,2S)-2-phenyl-cyclopropylamino)-thiazol-4-one (example 1f, 70 mg, 0.3 mmol) in toluene (2 mL) was added benzolic acid (3.5 mg, 0.03 mmol) and piperidine (35 uL, 0.03 mmol). The mixture was heated to 150° C. by microwave for 20 min.

After cooling to room temperature, the solid was collected by filtration, washed with toluene and dried. Flash chromatography (Merck Silica gel 60, 230-400 mesh, 0%-5% methanol in methylene chloride in 30 min) afforded 4-ethoxy-6-[4-oxo-2-((1R,2S)-2-phenyl-cyclopropylamino)-4H-thiazol-(5Z)-ylidenemethyl]-quinoline-3-carbonitrile (35 mg, 27%) as a light yellow solid: LC-MS m/e 441 (MH⁺).

Example 13

4-Ethoxy-6-[2-((R)-2-hydroxy-1-phenyl-ethylamino)-4-oxo-4H-thiazol-(5Z)-ylidenemethyl]-quinoline-3-carbonitrile

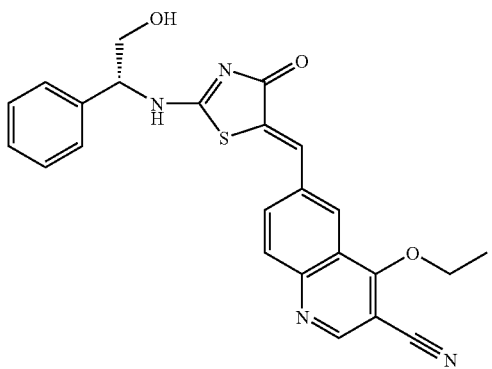

Similar procedure as described in example 1g was used, starting from 4-ethoxy-6-formyl-quinoline-3-carbonitrile (example 14e) and 2-((R)-2-hydroxy-1-phenyl-ethylamino)-thiazol-4-one (example 3a) to give 4-ethoxy-6-[2-((R)-2-hydroxy-1-phenyl-ethylamino)-4-oxo-4H-thiazol-(5Z)-ylidenemethyl]-quinoline-3-carbonitrile. LC-MS m/e 445 (MH⁺).

Example 14

4-Ethoxy-6-[2-[2-(3-fluoro-phenyl)-ethylamino]-4-oxo-4H-thiazol-(5Z)-ylidenemethyl]-quinoline-3-carbonitrile

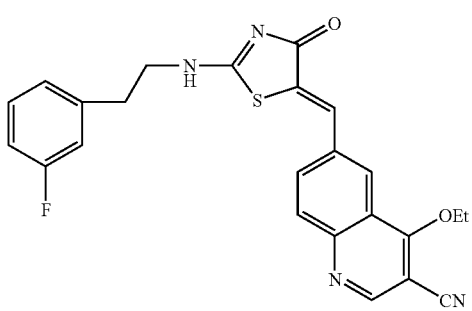

a) Preparation of 2-cyano-3-(4-iodo-phenylamino)-acrylic acid ethyl ester and (E)-2-cyano-3-(4-iodo-phenylamino)-acrylic acid ethyl ester

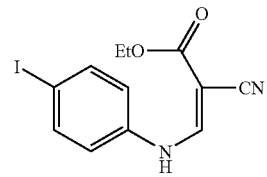

A mixture of 4-iodoaniline (110 g, 0.5 mol) and ethyl ethoxymethylenecyanoacetate (85 g, 0.5 mmol) in toluene (250 mL) was stirred at reflux for 10 hours. After cooling to room temperature, ether (250 mL) was added. The solid was collected, washed with ether and dried over the oven to obtain the mixture of (Z)-2-cyano-3-(4-iodo-phenylamino)-acrylic acid ethyl ester and (E)-2-cyano-3-(4-iodo-phenylamino)-acrylic acid ethyl ester (150 g, 88%) as a white solid. LC-MS m/e 343 (MH⁺).

b) Preparation of 6-iodo-4-oxo-1,4-dihydro-quinoline-3-carbonitrile

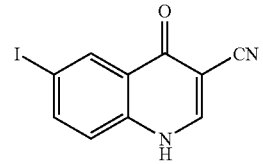

A mixture of (Z)-2-cyano-3-(4-iodo-phenylamino)-acrylic acid ethyl ester and (E)-2-cyano-3-(4-iodo-phenylamino)-acrylic acid ethyl ester (example 14a, 150 g, 0.44 mol) in diphenylether (1500 mL) was refluxed at 260° C. for 12 h. After cooling, ether was added. The solid was collected by filtration, washed with ether and dried to obtain 6-iodo-4-oxo-1,4-dihydro-quinoline-3-carbonitrile (110.5 g, 85%) as a black solid. LC-MS m/e 297 (MH⁺).

c) Preparation of 4-chloro-6-iodo-quinoline-3-carbonitrile

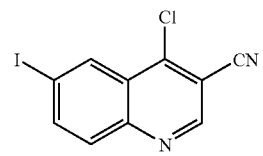

A mixture of 6 6-iodo-4-oxo-1,4-dihydro-quinoline-3-carbonitrile (example 14b) (100 g, 0.34 mol) in phosphorus oxychloride (300 mL) was refluxed under N2 for 7 h. After cooling, the solvent was removed by rotary evaporator and then by the oil pump. Sat. sodium bicarbonate (200 mL) and ice water were slowly added. The solid was collected by filtration, washed with sat. sodium bicarbonate, water and dried to obtain 4-chloro-6-iodo-quinoline-3-carbonitrile (58 g, 98%) as a yellow solid. LC-MS m/e 315 (MH⁺).

d) Preparation of 4-ethoxy-6-iodo-quinoline-3-carbonitrile

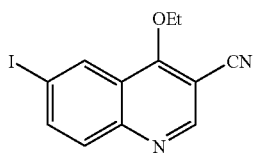

To the suspension of 4-chloro-6-iodo-quinoline-3-carbonitrile (example 14c) (14 g, 0.039 mol) in anhydrous ethanol (180 mL) was added sodium ethoxide (4.16 g, 0.07 mol). The mixture was heated to 100° C. under a pressure tube and stirred for 10 h. After cooling to room temperature, the ice water was added. The solid was collected by filtration, washed with water and dried to obtain 4-Ethoxy-6-iodo-quinoline-3-carbonitril (12 g, 92%) as a yellow solid. LC-MS m/e 325 (MH$^+$).

e) Preparation of 4-ethoxy-6-formyl-quinoline-3-carbonitrile

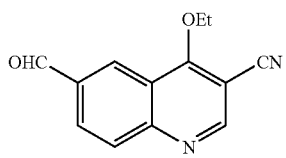

A mixture of 4-ethoxy-6-iodo-quinoline-3-carbonitrile (example 14d, 6.4 g, 20 mmol), trethylamine (6.9 mL, 50 mmol), diphenylpropylphosphine (dpp, 0.23 uL, 1 mmol) and palladium(II) acetate (0.22 g, 1 mmol) in dry N,N-dimethylformamide (120 mL) in pressure tube was stirred under carbon monoxide at 75 psi at room temperature for 10 min. After addition of trihexylsilane (14 mL, 40 mmol), the mixture was then stirred under carbon monoxide at 75 psi at 80° C. for 3 h. The reaction was allowed to cool to 25° C. and then extracted with ethyl acetate (2×200 mL). The combined organic layers were successively washed with a saturated aqueous sodium bicarbonate solution (3×50 mL) and water (3×50 mL), dried over sodium sulfate, filtered, and concentrated in vacuo. Flash chromatography (Merck Silica gel 60, 70-230 mesh, 5%-40% ethyl acetate in hexanes in 30 min) afforded 4-ethoxy-6-formyl-quinoline-3-carbonitrile (2.3 g, 51%) as a white solid. LC-MS m/e 227 (MH$^+$).

f) Preparation of 4-ethoxy-6-[4-oxo-2-thioxo-thiazolidin-(5Z)-ylidenemethyl]-quinoline-3-carbonitrile

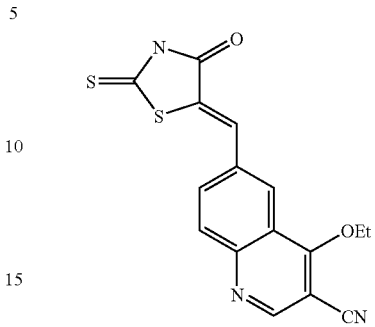

The suspension of 4-ethoxy-6-formyl-quinoline-3-carbonitrile (example 14e, 1.13 g, 5 mmol) and rodahnine (2-thioxo-thiazolin-4-one) (1.0 g, 7.5 mmol) in anhydrous toluene (50 mL) was added ammonium acetate (0.77 g, 10 mmol). The mixture was stirred under reflux for 6 h. After cooling to room temperature, the solid was collected by filtration, washed with water, toluene and dried to obtain 4-ethoxy-6-[4-oxo-2-thioxo-thiazolidin-(5Z)-ylidenemethyl]-quinoline-3-carbonitrile (1.7 g, 100%) as a grey solid. LC-MS m/e 342 (MH$^+$)

g) Preparation of 4-ethoxy-6-[2-methylsulfanyl-4-oxo-4H-thiazol-(5Z)-ylidenemethyl]-quinoline-3-carbonitrile

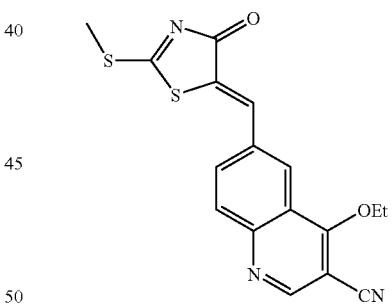

To the suspension of 4-ethoxy-6-[4-oxo-2-thioxo-thiazolidin-(5Z)-ylidenemethyl]-quinoline-3-carbonitrile (example 14f) (1.7 g, 5 mmol), iodomethane (0.62 mL, 10 mmol) and DIEA (diisopropylethylamine) (1.7 mL, 10 mmol) in anhydrous ethanol (25 mL) was stirred at room temperature for 24 h. After adding hexane (50 mL), the solid was collected by filtration, washed with hexane and dried. Flash chromatography (Merck Silica gel 60, 230-400 mesh, 0%-5% methanol in methylene chloride in 30 min) afforded to obtain 4-ethoxy-6-[2-methylsulfanyl-4-oxo-4H-thiazol-(5Z)-ylidenemethyl]-quinoline-3-carbonitrile(1.25 g, 75%) as a yellow solid. LC-MS m/e 356 (MH$^+$)

h) Preparation of 4-ethoxy-6-[2-[2-(3-fluoro-phenyl)-ethylamino]-4-oxo-4H-thiazol-(5Z)-ylidenemethyl]-quinoline-3-carbonitrile The suspension of 4-ethoxy-6-[2-methylsulfanyl-4-oxo-4H-thiazol-(5Z)-ylidenemethyl]-quinoline-3-carbonitrile (example 14 g) (71 mg, 0.2 mmol), m-fluorophenylethylamine (28 ul, 0.22 mmol) and DIEA (diisopropylethylamine) (0.11 mL, 0.44 mmol) in acetonitrile (2 mL) was stirred under at 80° C. for 4 h. After cooling to room temperature, the solid was collected by filtration, washed with a little bit of acetonitrile and dried. Flash chromatography (Merck Silica gel 60, 230-400 mesh, 0%-5% methanol in methylene chloride in 30 min) afforded 4-ethoxy-6-[2-[2-(3-fluoro-phenyl)-ethylamino]-4-oxo-4H-thiazol-(5Z)-ylidenemethyl]-quinoline-3-carbonitrile (60 mg, 67%) as a light yellow solid: LC-MS m/e 447 (MH$^+$).

Example 15

6-[2-Amino-4-oxo-4H-thiazol-(5Z)-ylidenemethyl]-4-ethoxy-quinoline-3-carbonitrile

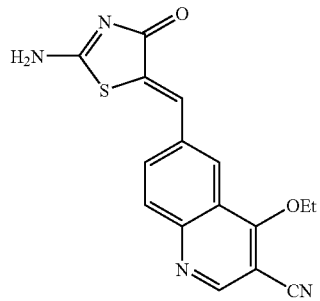

To the suspension of 4-ethoxy-6-formyl-quinoline-3-carbonitrile (example 14e) (45 mg, 0.2 mmol) and pseudothiohydantoin (35 mg, 0.3 mmol) in acetic acid (1 mL) was added sodium acetate (66 mg, 0.8 mol). The mixture was heated to 110° C. for 4 h. After cooling to room temperature, the ice water was added. The solid was collected by filtration, washed with water and dried. Flash chromatography (Merck Silica gel 60, 230-400 mesh, 0%-5% methanol in methylene chloride in 30 min) afforded 6-[2-amino-4-oxo-4H-thiazol-(5Z)-ylidenemethyl]-4-ethoxy-quinoline-3-carbonitrile (30 mg, 47%) as a light yellow solid: LC-MS m/e 445 (MH$^+$).

Example 16

2-[2-(3-Fluoro-phenyl)-ethylamino]-5-[1-[4-methoxy-3-(5-methyl-oxazol-2-yl)-quinolin-6-yl]-meth-(Z)-ylidene]-thiazol-4-one

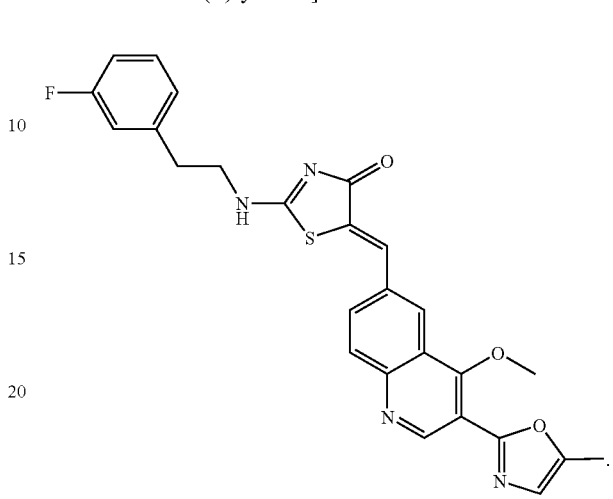

a) Preparation of 1-amino-propan-2-one hydrochloride

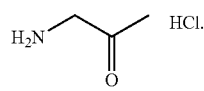

To the solution of Boc-glycine Weinreb amide (10 g, 46 mmol) in dry THF (tetrahydrofuran) (100 mL) was slowly added 1.4 M methyl magnesium chloride in toluene/THF (72 mL, 100 mmol) at −15° C. to −5° C. under N$_2$. After addition, the mixture was stirred at room temperature for over night. After adding aqueous 1.0N HCl solution (115 mL) at 0° C., the product was extracted with ethyl acetate (150 mL). The organic layers were successively washed with water (150 mL), dried over sodium sulfate, filtered, and concentrated in vacuo. Flash chromatography (Merck Silica gel 60, 70-230 mesh, 0-30% ethyl acetate in hexane in 30 min) afforded (2-oxo-propyl)-carbamic acid tert-butyl ester (6.99 g, 88%) as colorless oil.

To (2-oxo-propyl)-carbamic acid tert-butyl ester (6.99 mg, 40.4 mmol) was added 4 N HCl in dioxane (120 mL). After stirring 12 h and removal of the solvent, ether was added. The solid was collected by filtration and washed with ether and dried to give 1-amino-propan-2-one hydrochloride (4.51 g, 100%).

b) Preparation of 6-iodo-4-methoxy-quinoline-3-carboxylic acid (2-oxo-propyl)-amide

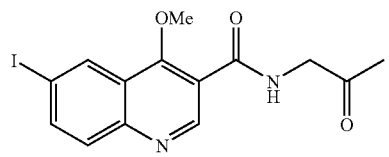

To the mixture of 6-iodo-4-methoxy-quinoline-3-carboxylic acid (example 1b) (4 g, 12.2 mmol), 1-aminopropan-2-one hydrochloride (3.94 g, 36.5 mmol), HOBt (1.97 g, 14.6 mmol) and DIEA (diisopropylethylamine) (8.5 mL, 48.8 mmol) in DMF (N,N-dimethylformamide) (100 mL) was slowly added the solution of O-benzotriazol-1-yl-N,N,N',N'-tetramethyluronium hexafluorophosphate (HBTU) (5.5 g, 14.6 mmol) in DMF (10 mL). After stirring at room temperature for 12 hours, the product was extracted with methylene chloride (2×300 mL). The combined organic layers were successively washed with a saturated aqueous sodium bicarbonate solution (3×150 mL) and water (3×150 mL), dried over sodium sulfate, filtered, and concentrated in vacuo. Flash chromatography (Merck Silica gel 60, 70-230 mesh, 0-10% MeOH in methylene chloride) afforded 6-iodo-4-methoxy-quinoline-3-carboxylic acid (2-oxo-propyl)-amide (1.63 g, 33%) as a yellow solid. LC-MS m/e 385 (MH⁺).

c) Preparation of 6-iodo-4-methoxy-3-(5-methyl-oxazol-2-yl)-quinoline

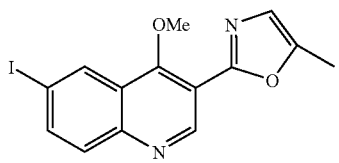

A mixture of 6-iodo-4-methoxy-quinoline-3-carboxylic acid (2-oxo-propyl)-amide (example 16b) (1.3 g, 3.38 mmol) and Burgess Regent ((methoxycarbonylsulfamoyl)-triethylammonium hydroxide, inner salt) (2.0 g, 8.5 mmol) in THF was heated to 150° C. for 15 min by microwave. The solvent was removed by rotary evaporator. Flash chromatography (Merck Silica gel 60, 70-230 mesh, 0%-50% ethyl acetate in hexanes in 30 min) afforded 6-iodo-4-methoxy-3-(5-methyl-oxazol-2-yl)-quinoline (0.49 g, 40%) as a white solid. LC-MS m/e 367 (MH⁺).

d) Preparation of 6-formyl-4-methoxy-3-(5-methyl-oxazol-2-yl)-quinoline

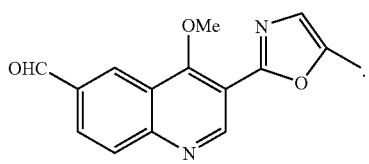

A mixture of 6-iodo-4-methoxy-3-(5-methyl-oxazol-2-yl)-quinoline (example 16c) (492 mg, 1.34 mmol), trethylamine (0.46 mL, 3.35 mmol), diphenylpropylphosphine (dpp, 31 uL, 0.13 mmol) and palladium(II) acetate (31 mg, 0.13 mmol) in dry N,N-dimethylformamide (20 mL) in pressure tube was stirred under carbon monoxide at 75 psi at room temperature for 10 min. After addition of trihexylsilane (1.01 mL, 2.68 mmol), the mixture was then stirred under carbon monoxide at 75 psi at 80° C. for 5 h. The reaction was allowed to cool to 25° C. and then extracted with ethyl acetate (2×100 mL). The combined organic layers were successively washed with a saturated aqueous sodium bicarbonate solution (3×50 mL) and water (3×50 mL), dried over sodium sulfate, filtered, and concentrated in vacuo. Flash chromatography (Merck Silica gel 60, 70-230 mesh, 0%-50% ethyl acetate in hexanes in 30 min) afforded 6-formyl-4-methoxy-3-(5-methyl-oxazol-2-yl)-quinoline (144 mg, 40%) as a white solid. LC-MS m/e 269 (MH⁺).

e) Preparation of 2-[2-(3-fluoro-phenyl)-ethylamino]-thiazol-4-one

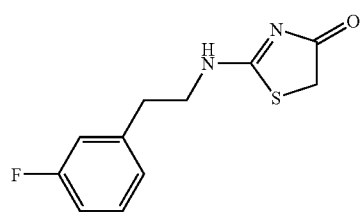

Similar procedure as described in example 1f was used, starting from 2-(3-fluoro-phenyl)-ethylamine, rhodanine (2-thioxo-thiazolin-4-one) and DIEA to give 2-[2-(3-fluoro-phenyl)-ethylamino]-thiazol-4-one. LC-MS m/e 239 (MH⁺).

f) Preparation of 2-[2-(3-Fluoro-phenyl)-ethylamino]-5-[1-[4-methoxy-3-(5-methyl-oxazol-2-yl)-quinolin-6-yl]-meth-(Z)-ylidene]-thiazol-4-one Similar procedure as described in example 1g was used, starting from 6-formyl-4-methoxy-3-(5-methyl-oxazol-2-yl)-quinoline (example 16d), 2-[2-(3-fluoro-phenyl)-ethylamino]-thiazol-4-one (example 16e), benzolic and piperidine to give 2-[2-(3-Fluoro-phenyl)-ethylamino]-5-[1-[4-methoxy-3-(5-methyl-oxazol-2-yl)-quinolin-6-yl]-meth-(Z)-ylidene]-thiazol-4-one. LC-MS m/e 489 (MH⁺).

Example 17

4-Ethoxy-6-[4-oxo-2-[(pyridin-2-ylmethyl)-amino]-4H-thiazol-(5Z)-ylidenemethyl]-quinoline-3-carbonitrile

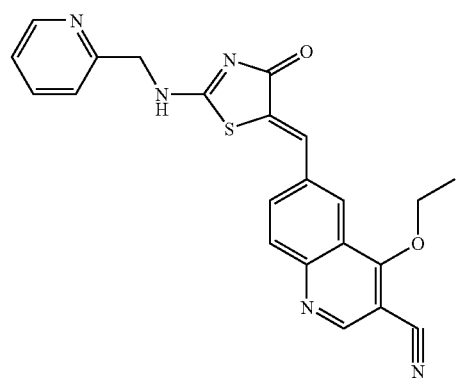

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), (pyridin-2-ylmethyl)-amine and DIEA to give 4-ethoxy-6-[4-oxo-2-[(pyridin-2-ylmethyl)-amino]-4H-thiazol-(5Z)-ylidenemethyl]-quinoline-3-carbonitrile. LC-MS m/e 416 (MH⁺).

Example 18

4-Ethoxy-6-[2-(2-hydroxy-2-phenyl-ethylamino)-4-oxo-4H-thiazol-(5Z)-ylidenemethyl]-quinoline-3-carbonitrile

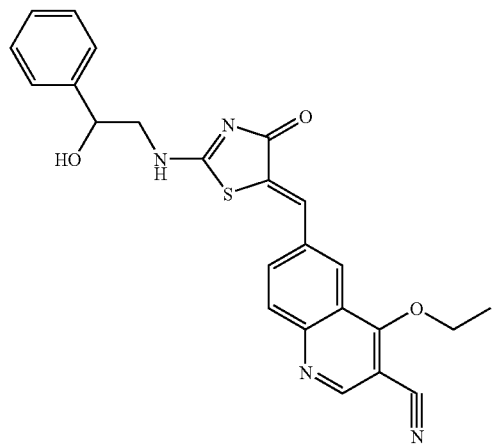

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), 2-hydroxy-2-phenyl-ethylamine and DIEA to give 4-ethoxy-6-[2-(2-hydroxy-2-phenyl-ethylamino)-4-oxo-4H-thiazol-(5Z)-ylidenemethyl]-quinoline-3-carbonitrile. LC-MS m/e 445 (MH$^+$).

Example 19

4-Ethoxy-6-[4-oxo-2-[(4-trifluoromethyl-pyridin-2-ylmethyl)-amino]-4H-thiazol-(5Z)-ylidenemethyl]-quinoline-3-carbonitrile

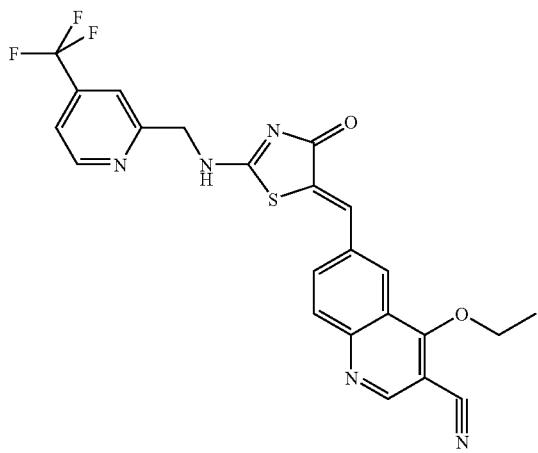

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), 4-trifluoromethyl-pyridin-2-ylmethylamine and DIEA to give 4-ethoxy-6-[4-oxo-2-[(4-trifluoromethyl-pyridin-2-ylmethyl)-amino]-4H-thiazol-(5Z)-ylidenemethyl]-quinoline-3-carbonitrile. LC-MS m/e 484 (MH$^+$).

Example 20

4-Ethoxy-6-[2-(2-imidazol-1-yl-ethylamino)-4-oxo-4H-thiazol-(5Z)-ylidenemethyl]-quinoline-3-carbonitrile

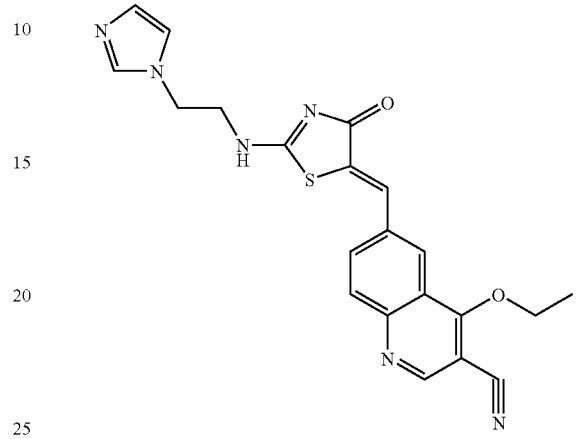

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), 2-imidazol-1-yl-ethylamine and DIEA to give 4-ethoxy-6-[2-(2-imidazol-1-yl-ethylamino)-4-oxo-4H-thiazol-(5Z)-ylidenemethyl]-quinoline-3-carbonitrile. LC-MS m/e 417 (MH$^+$).

Example 21

4-Ethoxy-6-[4-oxo-2-[(pyrazin-2-ylmethyl)-amino]-4H-thiazol-(5Z)-ylidenemethyl]-quinoline-3-carbonitrile

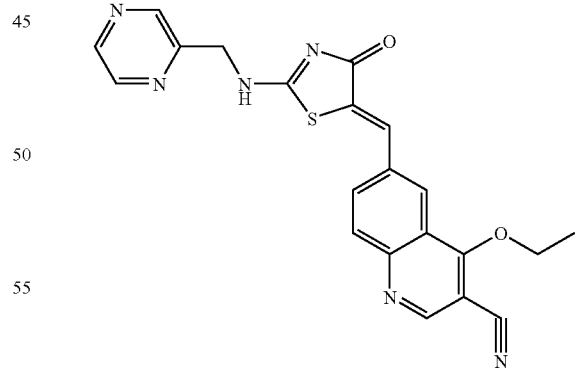

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), pyrazin-2-ylmethylamine and DIEA to give 4-ethoxy-6-[4-oxo-2-[(pyrazin-2-ylmethyl)-amino]-4H-thiazol-(5Z)-ylidenemethyl]-quinoline-3-carbonitrile. LC-MS m/e 417 (MH$^+$).

Example 22

4-Ethoxy-6-[4-oxo-2-[(pyrimidin-2-ylmethyl)-amino]-4H-thiazol-(Z)-ylidenemethyl]-quinoline-3-carbonitrile

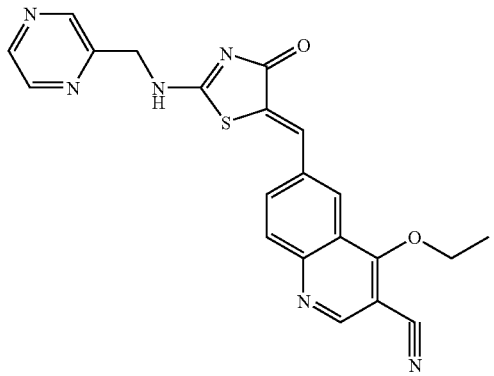

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), pyrimidin-2-ylmethylamine and DIEA to give 4-ethoxy-6-[4-oxo-2-[(pyrimidin-2-ylmethyl)-amino]-4H-thiazol-(5Z)-ylidenemethyl]-quinoline-3-carbonitrile. LC-MS m/e 417 (MH$^+$).

Example 23

6-[2-(2,2-Difluoro-2-pyridin-2-yl-ethylamino)-4-oxo-4H-thiazol-(Z)-ylidenemethyl]-4-ethoxy-quinoline-3-carbonitrile

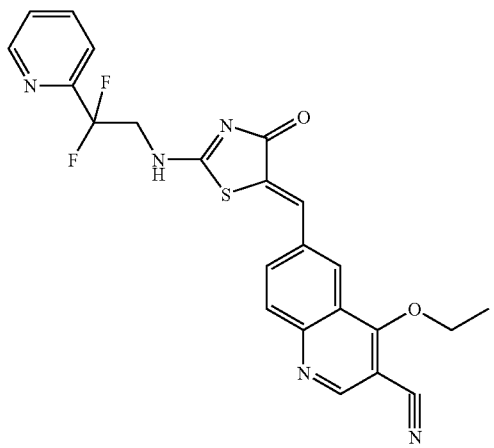

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), 2,2-difluoro-2-pyridin-2-yl-ethylamine and DIEA to give 6-[2-(2,2-Difluoro-2-pyridin-2-yl-ethylamino)-4-oxo-4H-thiazol-(5Z)-ylidenemethyl]-4-ethoxy-quinoline-3-carbonitrile. LC-MS m/e 466 (MH$^+$).

Example 24

6-[2-Cyclopropylamino-4-oxo-4H-thiazol-(5Z)-ylidenemethyl]-4-ethoxy-quinoline-3-carbonitrile

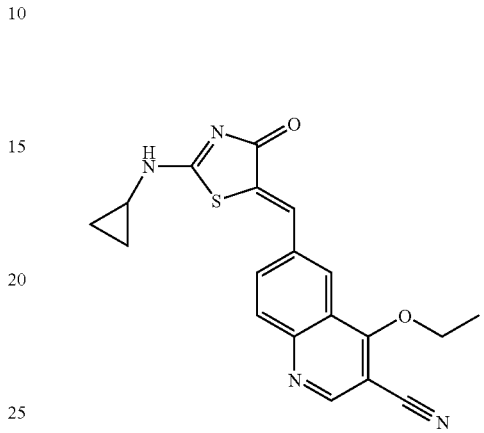

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), cyclopropylamine and DIEA to give 6-[2-Cyclopropylamino-4-oxo-4H-thiazol-(5Z)-ylidenemethyl]-4-ethoxy-quinoline-3-carbonitrile. LC-MS m/e 365 (MH$^+$).

Example 25

6-[2-[2-(2-methoxy-ethoxy)-ethylamino]-4-oxo-4H-thiazol-(5Z)-ylidenemethyl]-4-ethoxy-quinoline-3-carbonitrile

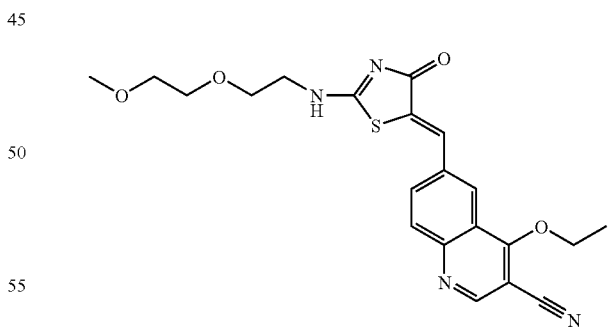

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), 2-(2-methoxy-ethoxy)-ethylamine and DIEA to give 6-[2-[2-(2-methoxy-ethoxy)-ethylamino]-4-oxo-4H-thiazol-(5Z)-ylidenemethyl]-4-ethoxy-quinoline-3-carbonitrile. LC-MS m/e 427 (MH$^+$).

Example 26

4-Ethoxy-6-[4-oxo-2-[(tetrahydro-pyran-4-ylmethyl)-amino]-4H-thiazol-(5Z)-ylidenemethyl]-quinoline-3-carbonitrile

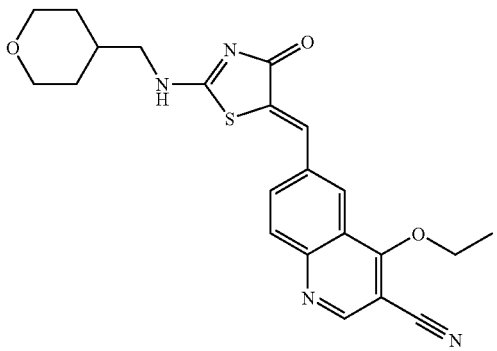

Similar procedure as described in example 14h was used, starting from 4-ethoxy-6-[4-oxo-2-thioxo-thiazolidin-(5Z)-ylidenemethyl]-quinoline-3-carbonitrile (example 14g), (tetrahydro-pyran-4-ylmethylamine and DIEA to give 4-Ethoxy-6-[4-oxo-2-[(tetrahydro-pyran-4-ylmethyl)-amino]-4H-thiazol-(5Z)-ylidenemethyl]-quinoline-3-carbonitrile. LC-MS m/e 423 (MH$^+$).

Example 27

4-Ethoxy-6-[4-oxo-2-[(thiazol-2-ylmethyl)-amino]-4H-thiazol-(5Z)-ylidenemethyl]-quinoline-3-carbonitrile

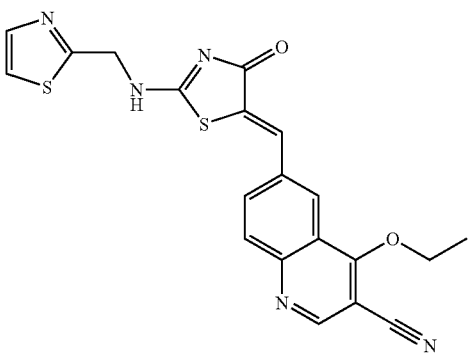

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), thiazol-2-ylmethyl-amine and DIEA to give 4-ethoxy-6-[4-oxo-2-[(thiazol-2-ylmethyl)-amino]-4H-thiazol-(5Z)-ylidenemethyl]-quinoline-3-carbonitrile. LC-MS m/e 422 (MH$^+$).

Example 28

6-[2-amino-4-oxo-4H-thiazol-(5Z)-ylidenemethyl]-4-[2-(2-methoxy-ethoxy)-ethoxy]-quinoline-3-carbonitrile

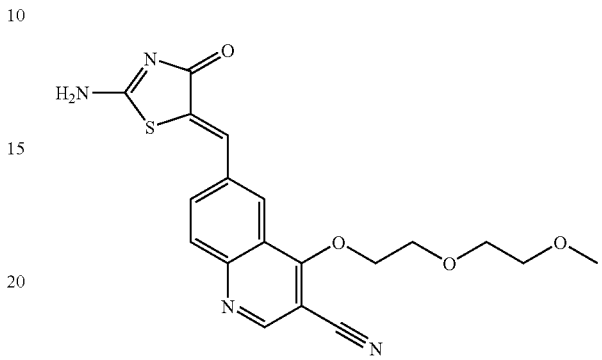

a) Preparation of 6-ido-4-[2-(2-methoxy-ethoxy)-ethoxy]-quinoline-3-carbonitrile

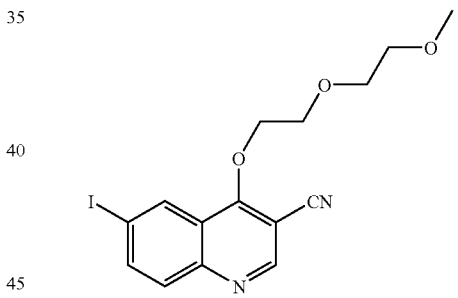

To the solution of diethylene glycol monomethyl ether (0.75 mL, 6.4 mmol) in DMF (10 mL) was added sodium hydride (0.26 g, 6.4 mmol). After stirring at room temperature for 30 min, 6-iodo-quinoline-3-carbonitrile (example 14c) (1.0 g, 3.18 mmol) was added to the mixture. After further stirring at room temperature for 30 min, ice water was slowly added to the reaction. The reaction was extracted with methylene chloride. The combined organic layers were successively washed with a saturated aqueous sodium bicarbonate solution and water, dried over sodium sulfate, filtered, and concentrated in vacuo. Flash chromatography (Merck Silica gel 60, 70-230 mesh, 0%-45% ethyl acetate in hexanes in 30 min) afforded 6-iodo-4-[2-(2-methoxy-ethoxy)-ethoxy]-quinoline-3-carbonitrile (0.59 g, 46%) as a light yellow solid. LC-MS m/e 399 (MH$^+$).

b) Preparation of 6-formyl-4-[2-(2-methoxy-ethoxy)-ethoxy]-quinoline-3-carbonitrile

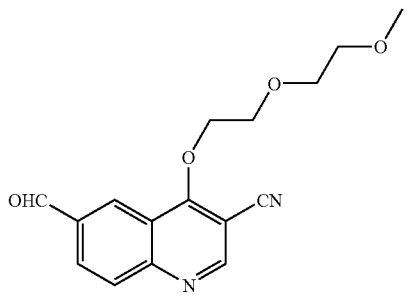

A mixture of 6-iodo-4-[2-(2-methoxy-ethoxy)-ethoxy]-quinoline-3-carbonitrile (example 14d) (0.78 g, 1.96 mmol), trethylamine (6.81 mL, 4.9 mmol), diphenylpropylphosphine (dpp, 44 uL, 0.2 mmol) and palladium(II) acetate (44 mg, 0.2 mmol) in dry DMSO (15 mL) in pressure tube was stirred under carbon monoxide at 75 psi at room temperature for 10 min. After addition of trihexylsilane (1.4 mL, 4.0 mmol), the mixture was then stirred under carbon monoxide at 75 psi at 80° C. for 5 h. The reaction was allowed to cool to 25° C. and then extracted with ethyl acetate (2×200 mL). The combined organic layers were successively washed with a saturated aqueous sodium bicarbonate solution (3×50 mL) and water (3×50 mL), dried over sodium sulfate, filtered, and concentrated in vacuo. Flash chromatography (Merck Silica gel 60, 70-230 mesh, 5%-50% ethyl acetate in hexanes in 30 min) afforded 6-formyl-4-[2-(2-methoxy-ethoxy)-ethoxy]-quinoline-3-carbonitrile (0.47 g, 81%) as a white solid. LC-MS m/e 301 (MH$^+$).

c) Preparation of 6-[2-amino-4-oxo-4H-thiazol-(5Z)-ylidenemethyl]-4-[2-(2-methoxy-ethoxy)-ethoxy]-quinoline-3-carbonitrile

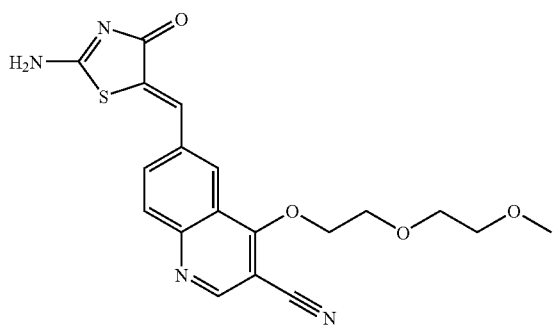

The suspension of 6-formyl-4-[2-(2-methoxy-ethoxy)-ethoxy]-quinoline-3-carbonitrile (example 28b, 50 mg, 0.17 mmol), pseudothiohydantoin (19.3 mg, 0.17 mmol), and sodium acetate (55 mg, 0.68 mmol) in acetic acid (180 uL) was stirred at 130° C. for 12 h. After cooling to room temperature, water was added. The solid was collected by filtration, washed with water and dried. Flash chromatography (Merck Silica gel 60, 70-230 mesh, 0%-7% methanol in methylene chloride in 30 min) afforded 6-[2-amino-4-oxo-4H-thiazol-(5Z)-ylidenemethyl]-4-[2-(2-methoxy-ethoxy)-ethoxy]-quinoline-3-carbonitrile (16.2 mg, 24%) as a slight yellow solid. LC-MS m/e 399 (MH$^+$).

Example 29

4-{6-[2-Amino-4-oxo-4H-thiazol-(5Z)-ylidenemethyl]-3-cyano-quinolin-4-yloxy}-piperidine-1-carboxylic acid tert-butyl ester

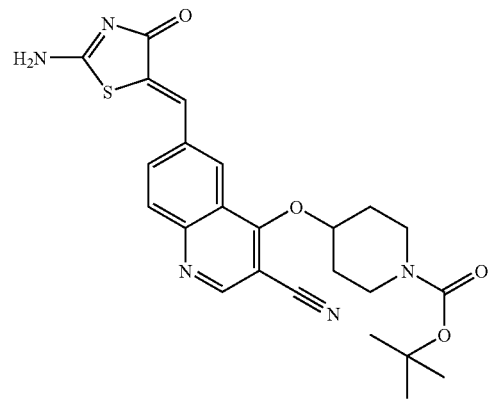

a) Preparation of 4-(3-cyano-6-iodo-quinolin-4-yloxy)-piperidine-1-carboxylic acid tert-butyl ester

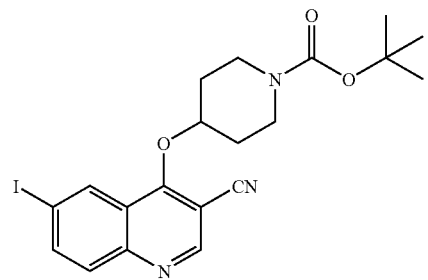

Similar procedure as described in example 28a was used, starting from 4-hydroxy-piperidine-1-carboxylic acid tert-butyl ester, 6-iodo-quinoline-3-carbonitrile (example 14c) and sodium hydride to give 4-(3-cyano-6-iodo-quinolin-4-yloxy)-piperidine-1-carboxylic acid tert-butyl ester. LC-MS m/e 480 (MH$^+$).

b) Preparation of 4-(3-cyano-6-formyl-quinolin-4-yloxy)-piperidine-1-carboxylic acid tert-butyl ester

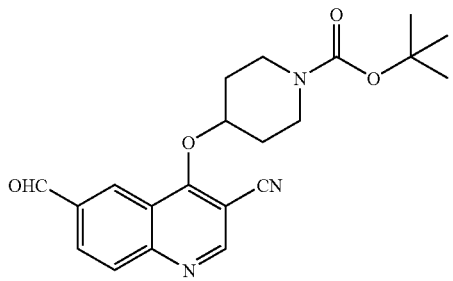

Similar procedure as described in example 28b was used, starting from 4-(3-cyano-6-iodo-quinolin-4-yloxy)-piperidine-1-carboxylic acid tert-butyl ester (example 31a), trethylamine, diphenylpropylphosphine, palladium(II) acetate and trihexylsilane to give 4-(3-cyano-6-formyl-quinolin-4-yloxy)-piperidine-1-carboxylic acid tert-butyl ester. LC-MS m/e 382 (MH$^+$).

c) Preparation of 4-{6-[2-amino-4-oxo-4H-thiazol-(5Z)-ylidenemethyl]-3-cyano-quinolin-4-yloxy}-piperidine-1-carboxylic acid tert-butyl ester Similar procedure as described in example 28c was used, starting from 4-(3-cyano-6-formyl-quinolin-4-yloxy)-piperidine-1-carboxylic acid tert-butyl ester, pseudothiohydantoin, sodium acetate and acetic acid to give 4-{6-[2-amino-4-oxo-4H-thiazol-(5Z)-ylidenemethyl]-3-cyano-quinolin-4-yloxy}-piperidine-1-carboxylic acid tert-butyl ester. LC-MS m/e 480 (MH$^+$).

Example 30

6-[2-Amino-4-oxo-4H-thiazol-(5Z)-ylidenemethyl]-4-(piperidin-4-yloxy)-quinoline-3-carbonitrile hydrochloride

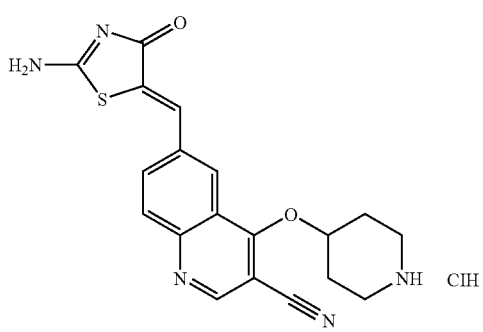

To 4-{6-[2-amino-4-oxo-4H-thiazol-(5Z)-ylidenemethyl]-3-cyano-quinolin-4-yloxy}-piperidine-1-carboxylic acid tert-butyl ester (example 29, 34 mg, 0.071 mmol) was added 4N HCl in dioxane (3 mL). After stirring 30 min and removal of the solvent, ether was added. The solid was collected by filtration and washed with ether and dried to give 6-[2-amino-4-oxo-4H-thiazol-(5Z)-ylidenemethyl]-4-(piperidin-4-yloxy)-quinoline-3-carbonitrile hydrochloride. LC-MS m/e 480 (MH$^+$).

Example 31

6-[2-tert-Butylamino-4-oxo-4H-thiazol-(5Z)-ylidenemethyl]-4-ethoxy-quinoline-3-carbonitrile

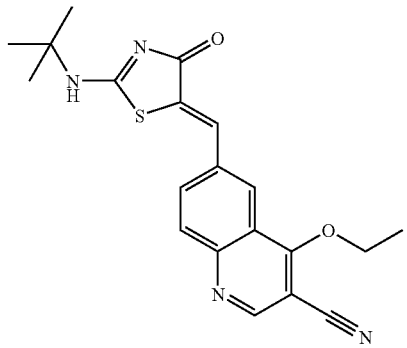

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), tert-butylamine and DIEA to give 6-[2-tert-Butylamino-4-oxo-4H-thiazol-(5Z)-ylidenemethyl]-4-ethoxy-quinoline-3-carbonitrile. LC-MS m/e 381 (MH$^+$).

Example 32

6-[2-Cyclopropylamino-4-oxo-4H-thiazol-(5Z)-ylidenemethyl]-4-[2-(2-methoxy-ethoxy)-ethoxy]-quinoline-3-carbonitrile

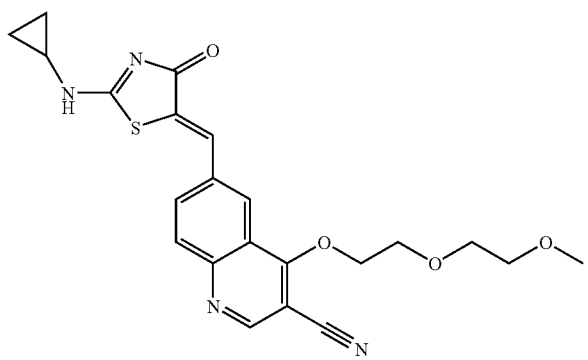

Similar procedure as described in example 28c was used, starting from 6-formyl-4-[2-(2-methoxy-ethoxy)-ethoxy]-quinoline-3-carbonitrile (example 30b), 2-cyclopropylamino-thiazol-4-one, sodium acetate and acetic acid to give 6-[2-cyclopropylamino-4-oxo-4H-thiazol-(5Z)-ylidenemethyl]-4-[2-(2-methoxy-ethoxy)-ethoxy]-quinoline-3-carbonitrile. LC-MS m/e 439 (MH$^+$).

Example 33

4-{3-Cyano-6-[2-cyclopropylamino-4-oxo-4H-thiazol-(5Z)-ylidenemethyl]-quinolin-4-yloxy}-piperidine-1-carboxylic acid tert-butyl ester

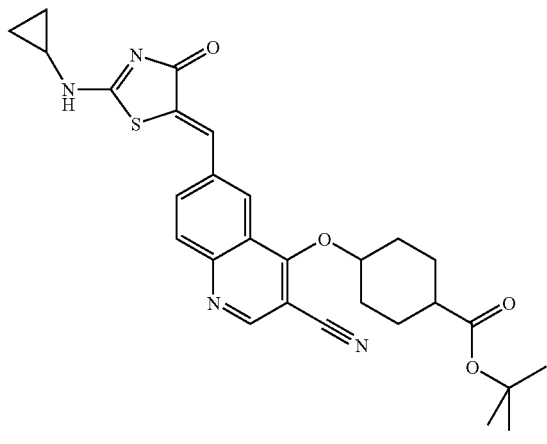

Similar procedure as described in example 28c was used, starting from 4-(3-cyano-6-formyl-quinolin-4-yloxy)-piperidine-1-carboxylic acid tert-butyl ester (example 31b), 2-cyclopropylamino-thiazol-4-one, sodium acetate and acetic acid to give 4-{3-cyano-6-[2-cyclopropylamino-4-oxo-4H-thiazol-(5Z)-ylidenemethyl]-quinolin-4-yloxy}-piperidine-1-carboxylic acid tert-butyl ester. LC-MS m/e 520 (MH$^+$).

Example 34

6-(2-Cyclopropylamino-4-oxo-4H-thiazol-5-ylidenemethyl)-4-(piperidin-4-yloxy)-quinoline-3-carbonitrile; hydrochloride

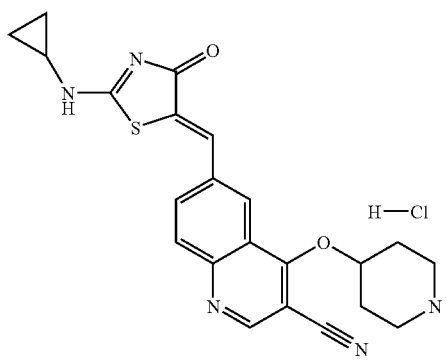

Similar procedure as described in example 30 was used, starting from 4-{3-cyano-6-[2-cyclopropylamino-4-oxo-4H-thiazol-(5Z)-ylidenemethyl]-quinolin-4-yloxy}-piperidine-1-carboxylic acid tert-butyl ester (example 33) and 4N HCl/Dioxane to give 6-(2-cyclopropylamino-4-oxo-4H-thiazol-5-ylidenemethyl)-4-(piperidin-4-yloxy)-quinoline-3-carbonitrile; hydrochloride. LC-MS m/e 420 (MH$^+$).

Example 35

4-Ethoxy-6-[2-((S)-2-hydroxy-2-phenyl-ethylamino)-4-oxo-4H-thiazol-(5Z)-ylidenemethyl]-quinoline-3-carbonitrile

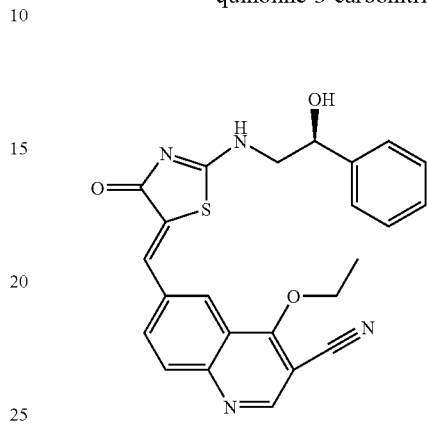

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), 2-((S)-2-hydroxy-2-phenyl-ethylamine and DIEA to give 4-ethoxy-6-[2-((S)-2-hydroxy-2-phenyl-ethylamino)-4-oxo-4H-thiazol-(5Z)-ylidenemethyl]-quinoline-3-carbonitrile. LC-MS m/e 445 (MH$^+$).

Example 36

4-Ethoxy-6-[2-((R)-2-hydroxy-2-phenyl-ethylamino)-4-oxo-4H-thiazol-(5Z)-ylidenemethyl]-quinoline-3-carbonitrile

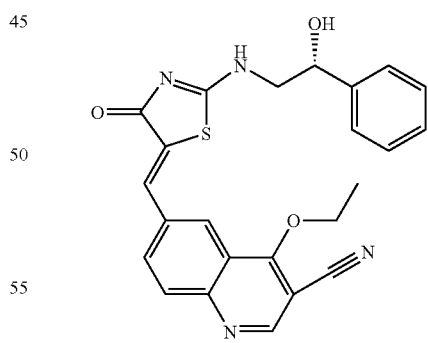

Similar procedure as described in example 14h was used, starting from 4-ethoxy-6-[2-methylsulfanyl-4-oxo-4H-thiazol-(5Z)-ylidenemethyl]-quinoline-3-carbonitrile (example 14g), 2-((R)-2-hydroxy-2-phenyl-ethylamine and DIEA to give 4-ethoxy-6-[2-((R)-2-hydroxy-2-phenyl-ethylamino)-4-oxo-4H-thiazol-(5Z)-ylidenemethyl]-quinoline-3-carbonitrile. LC-MS m/e 445 (MH$^+$).

Example 37

6-[2-Cyclopropylamino-4-oxo-4H-thiazol-(5Z)-ylidenemethyl]-4-isopropoxy-quinoline-3-carbonitrile

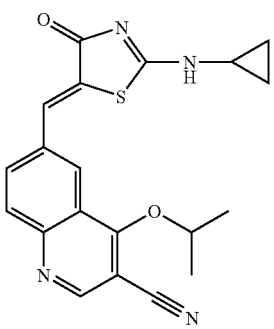

a) Preparation of 4-isoproxy-6-iodo-quinoline-3-carbonitrile

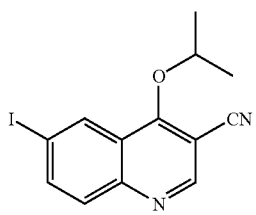

To the suspension of 4-chloro-6-iodo-quinoline-3-carbonitrile (example 14c, 3 g, 9.55 mmol) in anhydrous isopropanol (60 mL) was added sodium isopropoxide (3.2 g, 38.2 mmol). The mixture was heated to 120° C. under a pressure tube and stirred for 7 h. After cooling to room temperature, the ice water was added. The solid was collected by filtration, washed with water and saturated sodium carbonate and dried to obtain 4-isoproxy-6-iodo-quinoline-3-carbonitril (1.63 g, 51%) as a yellow solid. LC-MS m/e 339 (MH$^+$).

b) Preparation of 4-isoproxy-6-formyl-quinoline-3-carbonitrile

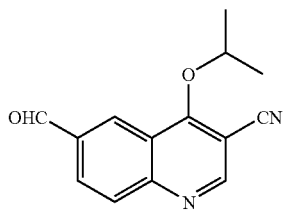

A mixture of 4-isoproxy-6-iodo-quinoline-3-carbonitrile (example 37a, 1.4 g, 4.14 mmol), trethylamine (1.43 mL, 10.35 mmol), diphenylpropylphosphine (dpp, 95 uL, 0.41 mmol) and palladium(II) acetate (0.093 g, 0.41 mmol) in dry DMSO (40 mL) in pressure tube was stirred under carbon monoxide at 75 psi at room temperature for 10 min. After addition of trihexylsilane (2.95 mL, 8.3 mmol), the mixture was then stirred under carbon monoxide at 70 psi at 80° C. for 4 h. The reaction was allowed to cool to 25° C. and then extracted with methylene chloride (2×100 mL). The combined organic layers were successively washed with a saturated aqueous sodium bicarbonate solution (3×50 mL) and water (3×50 mL), dried over sodium sulfate, filtered, and concentrated in vacuo. Flash chromatography (Merck Silica gel 60, 70-230 mesh, 0%-50% ethyl acetate in hexanes in 40 min) afforded 4-isoproxy-6-formyl-quinoline-3-carbonitrile (0.48 g, 48%) as a white solid. LC-MS m/e 241 (MH$^+$).

c) Preparation of 2-cyclopropylamino-thiazol-4-one

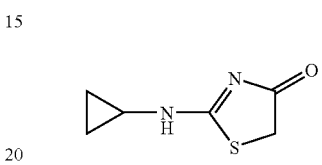

Similar procedure as described in example 1f was used, starting cyclopropylamine, rhodanine (2-thioxo-thiazolin-4-one) and DIEA to give 2-cyclopropylamino-thiazol-4-one. LC-MS m/e 157 (MH$^+$).

d) Preparation of 6-[2-cyclopropylamino-4-oxo-4H-thiazol-(5Z)-ylidenemethyl]-4-isopropoxy-quinoline-3-carbonitrile The suspension of 4-isoproxy-6-formyl-quinoline-3-carbonitrile (example 37b, 50 mg, 0.21 mmol), 2-cyclopropylamino-thiazol-4-one (example 37c, 32.5 mg, 0.21 mmol) and sodium acetate (68.2 mg, 0.83 mmol) was stirred for 10 min. To the above solution was added acetic acid (0.12 mL). The mixture was heated to 130° C. for 1 h. After cooling to room temperature, the ice water was added. The solid was collected by filtration, washed with water and dried. Flash chromatography (Merck Silica gel 60, 230-400 mesh, 0%-10% methanol in methylene chloride in 30 min) afforded 6-[2-cyclopropylamino-4-oxo-4H-thiazol-(5Z)-ylidenemethyl]-4-isopropoxy-quinoline-3-carbonitrile (58 mg, 73%) as a light yellow solid: LC-MS m/e 379 (MH$^+$).

Example 38

6-[2-Amino-4-oxo-4H-thiazol-(5Z)-ylidenemethyl]-4-isopropoxy-quinoline-3-carbonitrile

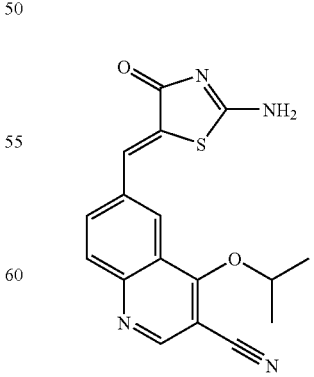

The suspension of 4-isoproxy-6-formyl-quinoline-3-carbonitrile (example 37b, 100 mg, 0.42 mmol), pseudothiohydantoin (65 mg, 0.42 mmol) and sodium acetate (137 mg, 1.66 mmol) was stirred for 10 min. To the above solution was added acetic acid (0.2 mL). The mixture was heated to 130° C. for 1 h. After cooling to room temperature, the ice water was added. The solid was collected by filtration, washed with water and saturated sodium carbonate and dried. Flash chromatography (Merck Silica gel 60, 230-400 mesh, 0%-10% methanol in methylene chloride in 30 min) afforded 6-[2-amino-4-oxo-4H-thiazol-(5Z)-ylidenemethyl]-4-isopropoxy-quinoline-3-carbonitrile (71 mg, 50%) as a light yellow solid: LC-MS m/e 339 (MH$^+$).

Example 39

6-[2-Amino-4-oxo-4H-thiazol-(5Z)-ylidenemethyl]-4-tert-butylsulfanyl-quinoline-3-carbonitrile

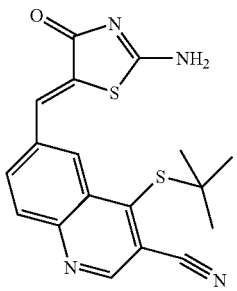

a) Preparation of 4-tert-Butylsulfanyl-6-iodo-quinoline-3-carbonitrile

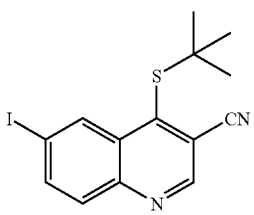

To the solution of 4-chloro-6-iodo-quinoline-3-carbonitrile (example 14c, 1.0 g, 3.18 mmol) in anhydrous DMF (1 mL) and DIEA (1.67 mL, 9.54 mmol) was added 2-methyl-2-propanethiol (0.72 ul, 6.4 mmol). The mixture was stirred at room temperature for 4 h. The reaction was extracted with methylene chloride (2×100 mL). The combined organic layers were successively washed with water (3×50 mL), dried over sodium sulfate, filtered, and concentrated in vacuo. Flash chromatography (Merck Silica gel 60, 70-230 mesh, 0%-50% ethyl acetate in hexanes in 30 min) afforded 4-tert-butylsulfanyl-6-iodo-quinoline-3-carbonitrile (0.57 g, 48%) as a white solid. LC-MS m/e 369 (MH$^+$).

b) Preparation of 4-tert-butylsulfanyl-6-formyl-quinoline-3-carbonitrile

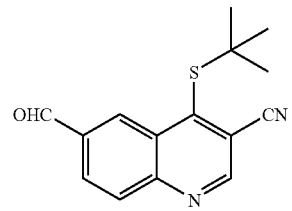

Similar procedure as described in example 37b was used, starting from 4-tert-butylsulfanyl-6-iodo-quinoline-3-carbonitrile (example 39a), trethylamine, diphenylpropylphosphine (dpp), palladium(II) acetate, carbon monoxide and trihexylsilane to give 4-tert-butylsulfanyl-6-formyl-quinoline-3-carbonitrile. LC-MS m/e 271 (MH$^+$).

c) Preparation of 6-[2-amino-4-oxo-4H-thiazol-(5Z)-ylidenemethyl]-4-tert-butylsulfanyl-quinoline-3-carbonitrile Similar procedure as described in example 38 was used, starting from 4-tert-butylsulfanyl-6-formyl-quinoline-3-carbonitrile (example 39b), pseudothiohydantoin, sodium acetate and acetic acid to give 6-[2-amino-4-oxo-4H-thiazol-(5Z)-ylidenemethyl]-4-tert-butylsulfanyl-quinoline-3-carbonitrile. LC-MS m/e 369 (MH$^+$).

Example 40

6-[2-Amino-4-oxo-4H-thiazol-(5Z)-ylidenemethyl]-4-tert-butylsulfanyl-quinoline-3-carbonitrile

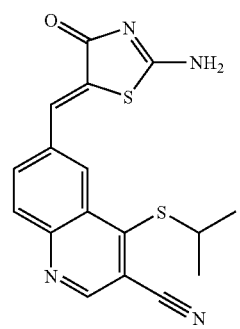

a) Preparation of 4-isopropylsulfanyl-6-iodo-quinoline-3-carbonitrile

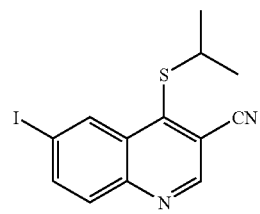

Similar procedure as described in example 39a was used, starting from 4-chloro-6-iodo-quinoline-3-carbonitrile (example 14c), DIEA and 2-propanethiol to give 4-isopropyl-sulfanyl-6-iodo-quinoline-3-carbonitrile. LC-MS m/e 355 (MH+).

b) Preparation of 4-isopropylsulfanyl-6-formyl-quinoline-3-carbonitrile

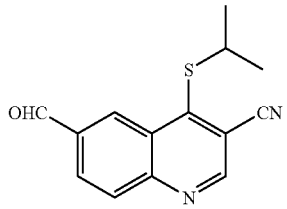

Similar procedure as described in example 37b was used, starting from 4-isoproxy-6-iodo-quinoline-3-carbonitrile (example 40a), trethylamine, diphenylpropylphosphine (dpp), palladium(II) acetate, carbon monoxide and trihexylsilane to give 4-isopropylsulfanyl-6-formyl-quinoline-3-carbonitrile. LC-MS m/e 257 (MH+).

c) Preparation of 6-[2-amino-4-oxo-4H-thiazol-(5Z)-ylidenemethyl]-4-isopropylsulfanyl-quinoline-3-carbonitrile Similar procedure as described in example 38 was used, starting from 4-isopropylsulfanyl-6-formyl-quinoline-3-carbonitrile (example 40b), pseudothiohydantoin, sodium acetate and acetic acid to give 6-[2-amino-4-oxo-4H-thiazol-(5Z)-ylidenemethyl]-4-isopropylsulfanyl-quinoline-3-carbonitrile. LC-MS m/e 355 (MH+).

Example 41

6-[2-((R)-1-Hydroxymethyl-2-methyl-propylamino)-4-oxo-4H-thiazol-(5Z)-ylidenemethyl]-4-isopropoxy-quinoline-3-carbonitrile

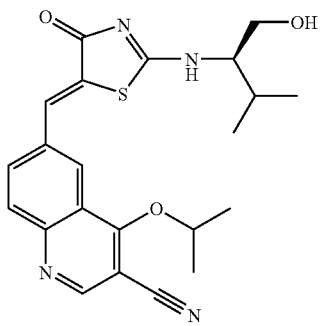

a) Preparation of 4-isoproxy-6-[4-oxo-2-thioxo-thiazolidin-(5Z)-ylidenemethyl]-quinoline-3-carbonitrile

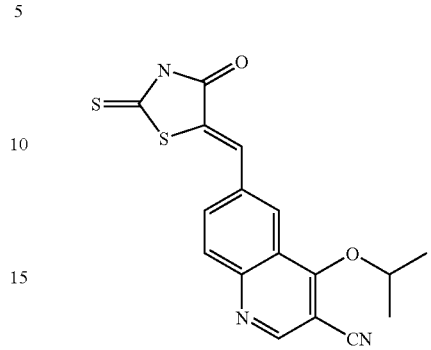

The suspension of 4-isoproxy-6-formyl-quinoline-3-carbonitrile (example 37b, 290 mg, 1.21 mmol), rodahnine (2-thioxo-thiazolin-4-one) (161 mg, 1.21 mmol) and sodium acetate (397 mg, 4.84 mmol) was stirred for 10 min. To the above solution was added acetic acid (0.73 mL). The mixture was heated to 130° C. for 2 h. After cooling to room temperature, the ice water was added. The solid was collected by filtration, washed with water and dried to obtain 4-isoproxy-6-[4-oxo-2-thioxo-thiazolidin-(5Z)-ylidenemethyl]-quinoline-3-carbonitrile (0.4 g, 88%) as a yellow solid. LC-MS m/e 356 (MH+)

b) Preparation of 4-isoproxy-6-[2-methylsulfanyl-4-oxo-4H-thiazol-(5Z)-ylidenemethyl]-quinoline-3-carbonitrile

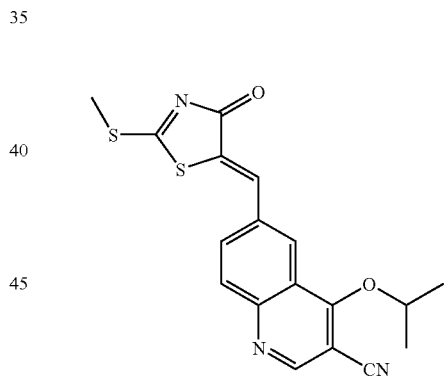

To the suspension of 4-isoproxy-6-[4-oxo-2-thioxo-thiazolidin-(5Z)-ylidenemethyl]-quinoline-3-carbonitrile (example 41a, 0.41 g, 1.14 mmol), iodomethane (0.14 mL, 2.3 mmol) and DIEA (diisopropylethylamine) (0.3 mL, 1.7 mmol) in anhydrous ethanol (4 mL) was stirred at room temperature for 24 h. After adding water (50 mL), the solid was collected by filtration, washed with water and dried to give 4-isoproxy-6-[2-methylsulfanyl-4-oxo-4H-thiazol-(5Z)-ylidenemethyl]-quinoline-3-carbonitrile (0.26 mg, 62%) as a yellow solid. LC-MS m/e 370 (MH+)

c) Preparation of 6-[2-((R)-1-hydroxymethyl-2-methyl-propylamino)-4-oxo-4H-thiazol-(5Z)-ylidenemethyl]-4-isopropoxy-quinoline-3-carbonitrile The suspension of 4-isoproxy-6-[2-methylsulfanyl-4-oxo-4H-thiazol-(5Z)-ylidenemethyl]-quinoline-3-carbonitrile (example 41b, 37 mg, 0.1 mmol), (R)-(−)-2-amino-3-methyl-1-butanol (20 mg, 0.2 mmol) and DIEA (diisopropylethylamine) (0.052 mL, 0.3 mmol) in acetonitrile (2 mL) was stirred under at 75° C. for 4 h. After cooling to room temperature, Flash chromatography (Merck Silica gel 60, 230-400 mesh, 0%-5% methanol in methylene chloride in 30 min) afforded 6-[2-((R)-1-hydroxymethyl-2-methyl-propylamino)-4-oxo-4H-thiazol-(5Z)-ylidenemethyl]-4-isopropoxy-quinoline-3-carbonitrile (25 mg, 60%) as a light yellow solid: LC-MS m/e 425 (MH$^+$).

Example 42

6-[2-((R)-2-Hydroxy-1-phenyl-ethylamino)-4-oxo-4H-thiazol-(5Z)-ylidenemethyl]-4-isopropoxy-quinoline-3-carbonitrile

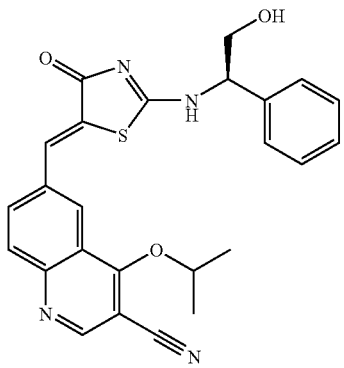

Similar procedure as described in example 41c was used, starting from 4-isoproxy-6-[2-methylsulfanyl-4-oxo-4H-thiazol-(5Z)-ylidenemethyl]-quinoline-3-carbonitrile (example 41b), (R)-2-hydroxy-1-phenyl-ethylamine and DIEA. After the reaction was completed, the solid was collected by filtration, washed with a little bit of acetonitrile and dried. Flash chromatography (Merck Silica gel 60, 230-400 mesh, 0%-5% methanol in methylene chloride in 30 min) afforded 6-[2-((R)-2-hydroxy-1-phenyl-ethylamino)-4-oxo-4H-thiazol-(5Z)-ylidenemethyl]-4-isopropoxy-quinoline-3-carbonitrile. LC-MS m/e 459 (MH$^+$).

Example 43

6-[2-Amino-4-oxo-4H-thiazol-(5Z)-ylidenemethyl]-4-(2,2,2-trifluoro-ethoxy)-quinoline-3-carbonitrile

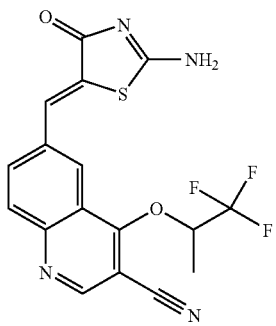

a) Preparation of 6-iodo-4-(2,2,2-trifluoro-ethoxy)-quinoline-3-carbonitrile

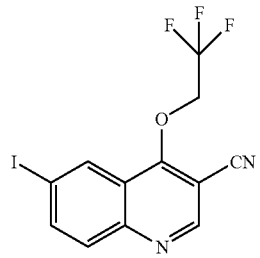

The solution of sodium hydride (60%, 0.76 g, 19.1 mmol) in anhydrous THF (90 mL) was stirred at room temperature for 30 min. To the above solution was added 4-chloro-6-iodo-quinoline-3-carbonitrile (example 14c, 3 g, 9.55 mmol). The mixture was stirred at room temperature for 1 h. The reaction was extracted with methylene chloride (2×100 mL). The combined organic layers were successively washed with water (3×50 mL), dried over sodium sulfate, filtered, and concentrated in vacuo. Flash chromatography (Merck Silica gel 60, 70-230 mesh, 0%-50% ethyl acetate in hexanes in 30 min) afforded 6-iodo-4-(2,2,2-trifluoro-ethoxy)-quinoline-3-carbonitrile (1.67 g, 45%) as a white solid. LC-MS m/e 379 (MH$^+$).

b) Preparation of 6-formyl-4-(2,2,2-trifluoro-ethoxy)-quinoline-3-carbonitrile

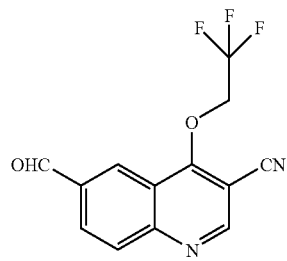

Similar procedure as described in example 37b was used, starting from 6-iodo-4-(2,2,2-trifluoro-ethoxy)-quinoline-3-carbonitrile (example 40a), trethylamine, diphenylpropylphosphine (dpp), palladium(II) acetate, carbon monoxide and trihexylsilane to give 6-formyl-4-(2,2,2-trifluoro-ethoxy)-quinoline-3-carbonitrile. LC-MS m/e 281 (MH$^+$).

c) Preparation of 6-[2-amino-4-oxo-4H-thiazol-(5Z)-ylidenemethyl]-4-(2,2,2-trifluoro-ethoxy)-quinoline-3-carbonitrile Similar procedure as described in example 38 was used, starting from 6-formyl-4-(2,2,2-trifluoro-ethoxy)-quinoline-3-carbonitrile (example 43b), pseudothiohydantoin, sodium acetate and acetic acid to give 6-[2-amino-4-oxo-4H-thiazol-(5Z)-ylidenemethyl]-4-(2,2,2-trifluoro-ethoxy)-quinoline-3-carbonitrile. LC-MS m/e 379 (MH$^+$).

Example 44

6-[2-(2,3-Dihydroxy-propylamino)-4-oxo-4H-thiazol-(5Z)-ylidenemethyl]-4-isopropylsulfanyl-quinoline-3-carbonitrile

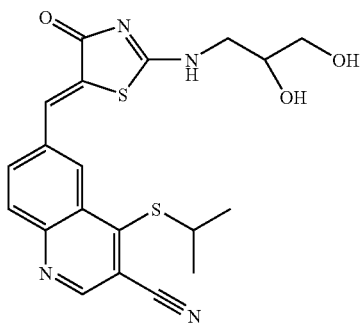

Similar procedure as described in example 41c was used, starting from 4-isoproxy-6-[2-methylsulfanyl-4-oxo-4H-thiazol-(5Z)-ylidenemethyl]-quinoline-3-carbonitrile (example 41b), 2,3-dihydroxy-propylamine and DIEA. After the reaction was completed, the solid was collected by filtration, washed with a little bit of acetonitrile and dried. Flash chromatography (Merck Silica gel 60, 230-400 mesh, 0%-5% methanol in methylene chloride in 30 min) afforded 6-[2-(2,3-dihydroxy-propylamino)-4-oxo-4H-thiazol-(5Z)-ylidenemethyl]-4-isopropylsulfanyl-quinoline-3-carbonitrile. LC-MS m/e 429 (MH$^+$).

Example 45

6-[2-Amino-4-oxo-4H-thiazol-(5Z)-ylidenemethyl]-4-(2,2,2-trifluoro-1-trifluoromethyl-ethoxy)-quinoline-3-carbonitrile

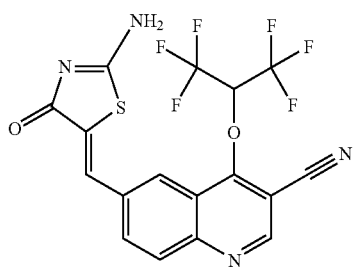

a) Preparation of 6-iodo-4-(2,2,2-trifluoro-1-trifluoromethyl-ethoxy)-quinoline-3-carbonitrile

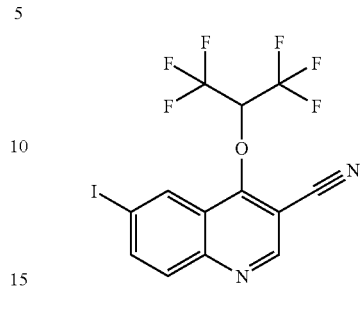

To the suspension of 4-chloro-6-iodo-quinoline-3-carbonitrile (example 14c, 3.14 g, 10 mmol) and potassium carbonate (5.5 g, 40 mmol) ih tetrahydrofuran (10 mL) was added 1,1,1,3,3,3-hexafluoro-propanol. The mixture was stirred at room temperature for 2 days. After adding water, the solid was collected by filtration and washed with saturated sodium carbonate and water, and dried to give 6-iodo-4-(2,2,2-trifluoro-1-trifluoromethyl-ethoxy)-quinoline-3-carbonitrile (3.7 g, 83%) as a brown solid. LC-MS m/e 447 (MH$^+$).

b) Preparation of 6-formyl-4-(2,2,2-trifluoro-1-trifluoromethyl-ethoxy)-quinoline-3-carbonitrile

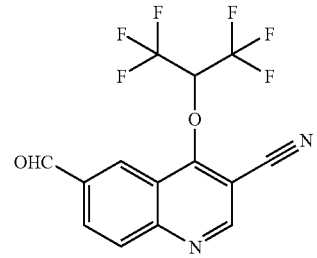

Similar procedure as described in example 37b was used, starting from 6-iodo-4-(2,2,2-trifluoro-1-trifluoromethyl-ethoxy)-quinoline-3-carbonitrile (example 45a), trethylamine, diphenylpropylphosphine (dpp), palladium(II) acetate, carbon monoxide and trihexylsilane to give 6-formyl-4-(2,2,2-trifluoro-1-trifluoromethyl-ethoxy)-quinoline-3-carbonitrile. LC-MS m/e 349 (MH$^+$).

c) Preparation of 6-[2-amino-4-oxo-4H-thiazol-(5Z)-ylidenemethyl]-4-(2,2,2-trifluoro-1-trifluoromethyl-ethoxy)-quinoline-3-carbonitrile Similar procedure as described in example 38 was used, starting from 6-formyl-4-(2,2,2-trifluoro-1-trifluoromethyl-ethoxy)-quinoline-3-carbonitrile (example 45b), pseudothiohydantoin, sodium acetate and acetic acid to give 6-[2-amino-4-oxo-4H-thiazol-(5Z)-ylidenemethyl]-4-(2,2,2-trifluoro-1-trifluoromethyl-ethoxy)-quinoline-3-carbonitrile. LC-MS m/e 447 (MH$^+$).

Example 46

6-[2-Amino-4-oxo-4H-thiazol-(5Z)-ylidenemethyl]-4-isobutyl-quinoline-3-carbonitrile

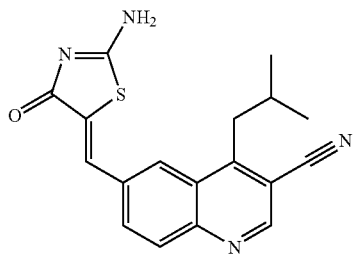

a) Preparation of 4-(2-cyano-2-ethoxycarbonyl-vinylamino)-benzoic acid ethyl ester

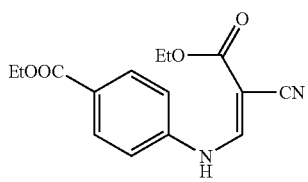

The mixture of triethyl orthoformate (33.3 mL, 0.2 mol) and ethyl cyanoacetate (21.3 mL, 0.2 mol) in acetic anhydride (80 mL) was heated at 150-160° C. for 5 h. After cooling to room temperature, the solvent was removed under reduced pressure to give ethyl 2-cyano-3-ethoxyacrylate as a yellow solid (28.5 g, 84%).

The mixture of ethyl 2-cyano-3-ethoxyacrylate (28.5 g, 0.168 mol) and 4-aminobenzoic acid ethyl ester (26.5 g, 0.16 mol) was heated at 150° C. for 2 h, detected by HPLC. After cooling to room temperature, the reaction mixture was dried under reduced pressure to give 4-(2-cyano-2-ethoxycarbonyl-vinylamino)-benzoic acid ethyl ester as a grey solid. LC-MS m/e 289 (MH$^+$).

b) Preparation of 3-cyano-4-oxo-1,4-dihydro-quinoline-6-carboxylic acid ethyl ester

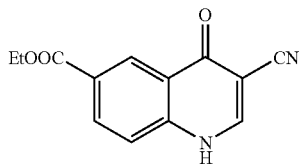

The mixture of 4-(2-cyano-2-ethoxycarbonyl-vinylamino)-benzoic acid ethyl ester (55 g, 0.19 mol) in diphenyl ether (300 mL) was stirred under reflux for 4 h. HPLC showed all the starting material disappeared. After cooling to 40° C., the solution was poured into petroleum ether (1000 mL). The solid was filtered, washed with petroleum ether, ethyl acetate and dried to give 3-cyano-4-oxo-1,4-dihydro-quinoline-6-carboxylic acid ethyl ester as a brown solid (39 g, 85%). HPLC showed 90% purity. LC-MS m/e 243 (MH$^+$)

c) Preparation of 4-chloro-3-cyano-quinoline-6-carboxylic acid ethyl ester

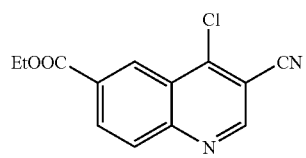

A mixture of 6 6-iodo-4-oxo-1,4-dihydro-quinoline-3-carbonitrile (example 14b, 100 g, 0.34 mol) in phosphorus oxychloride (300 mL) was refluxed under N$_2$ for 12 h. After cooling, the solvent was removed by rotary evaporator and then by the oil pump. The ice water and saturated sodium bicarbonate (200 mL) and ice water were slowly added. The solid was collected by filtration, washed with saturated sodium carbonate, water and dried to obtain 4-chloro-3-cyano-quinoline-6-carboxylic acid ethyl ester (12.6 g, 97%) as a grey solid. LC-MS m/e 261 (MH$^+$).

d) Preparation of 3-cyano-4-isobutyl-quinoline-6-carboxylic acid ethyl ester

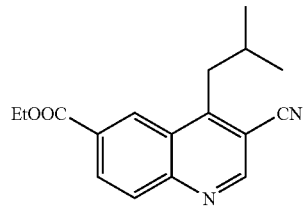

The mixture of 4-chloro-3-cyano-quinoline-6-carboxylic acid ethyl ester (example 46c, 1.3 g, 5 mmol), (2-methylpropyl)boronic acid (1.0 g, 10 mmol), sodium carbonate (3.18 g, 30 mmol) and POPd (bis[bis(1,1-dimethylethyl) phosphinous acid-κP]dichloropalladium, CAS: 391683-95-7) (75 mg, 0.15 mmol) in dimethyloxyethane (DME) (20 mL) was stirred at 100° C. for 2 days. After cooling to room temperature, the product was extracted with ethylacetate. The combined organic layers were successively washed with water, dried over sodium sulfate, filtered, and concentrated in vacuo. Flash chromatography (Merck Silica gel 60, 70-230 mesh, 0%-50% ethyl acetate in hexanes in 30 min) afforded 3-cyano-4-isobutyl-quinoline-6-carboxylic acid ethyl ester (1.1 g, 79%) as a clear oil. LC-MS m/e 283 (MH$^+$).

e) Preparation of 6-hydroxymethyl-4-isobutyl-1,4-dihydro-quinoline-3-carbonitrile

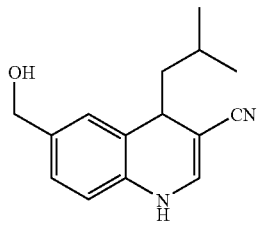

To the suspension of lithium borohydride (93 mg, 4.3 mmol) and methanol (170 uL, 4.3 mmol) in ether (20 mL) was added the solution of 3-cyano-4-isobutyl-quinoline-6-carboxylic acid ethyl ester (example 46d, 600 mg, 2.1 mmol) in ether (5 mL). The mixture was stirred at reflux overnight. The mixture of water and methanol (v/v 1:1, 40 mL) was added to the above solution. Then 1 N HCl (3 mL) was added to quench the reaction. The product was extracted with ethylacetate. The combined organic layers were successively washed with water, dried over sodium sulfate, filtered, and concentrated in vacuo. Flash chromatography (Merck Silica gel 60, 70-230 mesh, 5%-50% ethyl acetate in hexanes in 50 min) afforded 6-hydroxymethyl-4-isobutyl-1,4-dihydro-quinoline-3-carbonitrile (220 mg, 43%) as a yellow solid. LC-MS m/e 243 (MH$^+$).

f) Preparation of 6-formyl-4-isobutyl-quinoline-3-carbonitrile

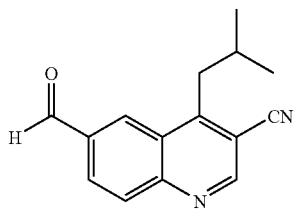

To the solution of 6-hydroxymethyl-4-isobutyl-1,4-dihydro-quinoline-3-carbonitrile (200 mg, 0.83 mmol) in chloroform (6 mL) was added manganese dioxide (300 mg). The mixture was stirred at reflux for 10 h. After removal of the solid by filtration, the filtrate was concentrated in vacuo. Flash chromatography (Merck Silica gel 60, 70-230 mesh, 0%-30% ethyl acetate in hexanes in 30 min) afforded 6-formyl-4-isobutyl-quinoline-3-carbonitrile (110 mg, 56%) as a white solid. LC-MS m/e 239 (MH$^+$).

g) Preparation of 6-[2-amino-4-oxo-4H-thiazol-(5Z)-ylidenemethyl]-4-isobutyl-quinoline-3-carbonitrile Similar procedure as described in example 38 was used, starting from 6-formyl-4-isobutyl-quinoline-3-carbonitrile (example 46f), pseudothiohydantoin, sodium acetate and acetic acid to give 6-[2-amino-4-oxo-4H-thiazol-(5Z)-ylidenemethyl]-4-isobutyl-quinoline-3-carbonitrile. LC-MS m/e 337 (MH$^+$).

Example 47

6-[2-Amino-4-oxo-4H-thiazol-(5Z)-ylidenemethyl]-4-isopropylsulfanyl-quinoline-3-carbonitrile methanesulfonic acid salt

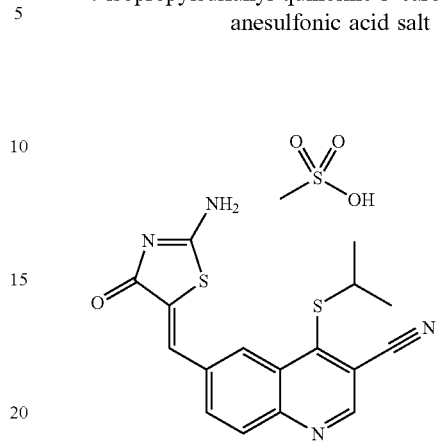

To the solution of 6-[2-amino-4-oxo-4H-thiazol-(5Z)-ylidenemethyl]-4-isobutyl-quinoline-3-carbonitrile (example 40c, 30 mg, 0.085 mmol) in methylene chloride (2.5 mL) and methanol (2.5 mL) was added methanesulfonic acid (13 uL, 0.196 mmol) in methanol (1 mL). After stirring for 10 min, ether (20 mL) was added slowly. The mixture was stirred for 1 h. The solid was collected by filtration and washed with ether and dried to give 6-[2-amino-4-oxo-4H-thiazol-(5Z)-ylidenemethyl]-4-isopropylsulfanyl-quinoline-3-carbonitrile methanesulfonic acid salt as light yellow solid (30 mg, 75%). LC-MS m/e 355 (MH$^+$).

Example 48

6-[2-Amino-4-oxo-4H-thiazol-(5Z)-ylidenemethyl]-4-isobutyl-quinoline-3-carbonitrile methanesulfonic acid salt

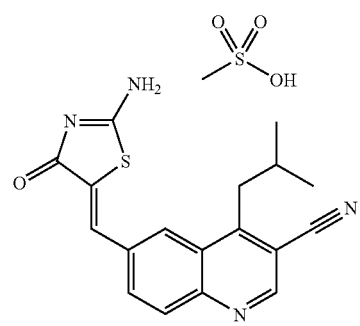

Similar procedure as described in example 47 was used, starting from 6-[2-amino-4-oxo-4H-thiazol-(5Z)-ylidenemethyl]-4-isobutyl-quinoline-3-carbonitrile (example 46g) and methanesulfonic acid to give 6-[2-amino-4-oxo-4H-thiazol-(5Z)-ylidenemethyl]-4-isobutyl-quinoline-3-carbonitrile methanesulfonic acid salt. LC-MS m/e 337 (MH$^+$).

Example 49

6-[2-Amino-4-oxo-4H-thiazol-(5Z)-ylidenemethyl]-4-butyl-quinoline-3-carbonitrile

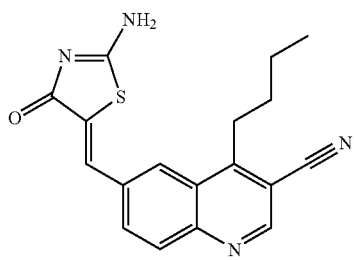

a) Preparation of 3-cyano-4-butyl-quinoline-6-carboxylic acid ethyl ester

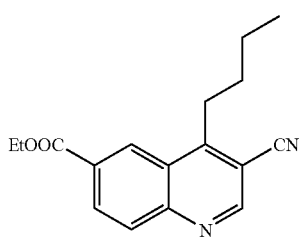

Similar procedure as described in example 46d was used, starting from 4-chloro-3-cyano-quinoline-6-carboxylic acid ethyl ester, butylboronic acid, sodium carbonate and POPd to give 3-cyano-4-butyl-quinoline-6-carboxylic acid ethyl ester as a clear oil. LC-MS m/e 283 (MH$^+$).

b) Preparation of 6-hydroxymethyl-4-butyl-1,4-dihydro-quinoline-3-carbonitrile

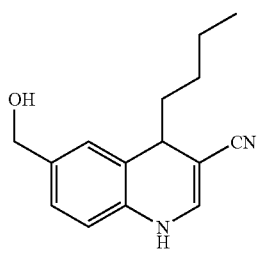

Similar procedure as described in example 46e was used, starting from 3-cyano-4-butyl-quinoline-6-carboxylic acid ethyl ester (example 49a) and lithium borohydride to give 6-hydroxymethyl-4-butyl-1,4-dihydro-quinoline-3-carbonitrile as a yellow solid. LC-MS m/e 243 (MH$^+$).

c) Preparation of 6-formyl-4-butyl-quinoline-3-carbonitrile

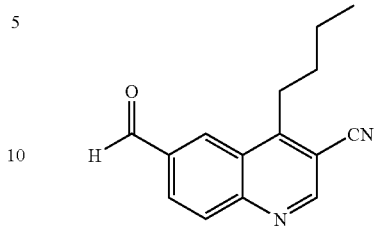

Similar procedure as described in example 46f was used, starting from 6-hydroxymethyl-4-butyl-1,4-dihydro-quinoline-3-carbonitrile (example 49b) and manganese dioxide to give 6-formyl-4-isobutyl-quinoline-3-carbonitrile as a white solid. LC-MS m/e 239 (MH$^+$).

d) Preparation of 6-[2-amino-4-oxo-4H-thiazol-(5Z)-ylidenemethyl]-4-isobutyl-quinoline-3-carbonitrile Similar procedure as described in example 38 was used, starting from 6-formyl-4-butyl-quinoline-3-carbonitrile (example 49c), pseudothiohydantoin, sodium acetate and acetic acid to give 6-[2-amino-4-oxo-4H-thiazol-(5Z)-ylidenemethyl]-4-butyl-quinoline-3-carbonitrile. LC-MS m/e 337 (MH$^+$).

Example 50

6-[2-Amino-4-oxo-4H-thiazol-(5Z)-ylidenemethyl]-4-(3-hydroxy-propylsulfanyl)-quinoline-3-carbonitrile

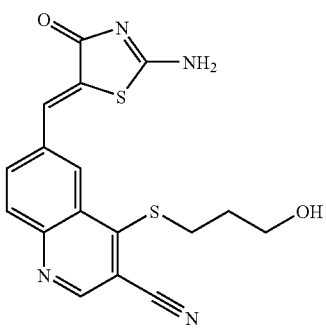

a) Preparation of 4-(3-hydroxy-propylsulfanyl)-6-iodo-quinoline-3-carbonitrile

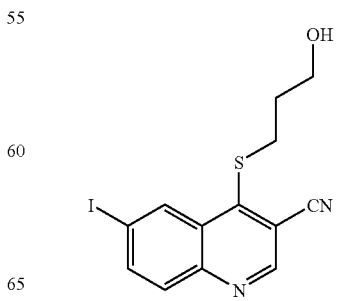

Similar procedure as described in example 39a was used, starting from 4-chloro-6-iodo-quinoline-3-carbonitrile (example 14c), DIEA and 3-mercapto-1-propanol to give 4-(3-hydroxy-propylsulfanyl)-6-iodo-quinoline-3-carbonitrile. LC-MS m/e 371 (MH+).

b) Preparation of 4-[3-(tert-butyl-dimethyl-silanyloxy)-propylsulfanyl]-6-iodo-quinoline-3-carbonitrile

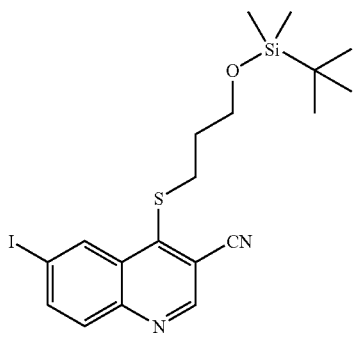

To the solution of 4-(3-hydroxy-propylsulfanyl)-6-iodo-quinoline-3-carbonitrile (example 50a, 3.0 g, 8.1 mmol) and imidazole (2.2 g, 32.4 mmol) in DMF (10 mL) was added dropwisely the solution of tert-butyldimethylsilyl chloride (TBDMS-Cl, 2.94 g, 19.4 mmol) in DMF (10 mL). The reaction mixture was stirred at room temperature overnight. The product was extracted with ethylacetate. The combined organic layers were successively washed with water, dried over sodium sulfate, filtered, and concentrated in vacuo. Flash chromatography (Merck Silica gel 60, 70-230 mesh, 5%-30% ethyl acetate in hexanes in 50 min) afforded 4-[3-(tert-butyl-dimethyl-silanyloxy)-propylsulfanyl]-6-iodo-quinoline-3-carbonitrile (3.41 g, 87%) as a yellow solid. LC-MS m/e 485 (MH+).

c) Preparation of 4-[3-(tert-butyl-dimethyl-silanyloxy)-propylsulfanyl]-6-formyl-quinoline-3-carbonitrile

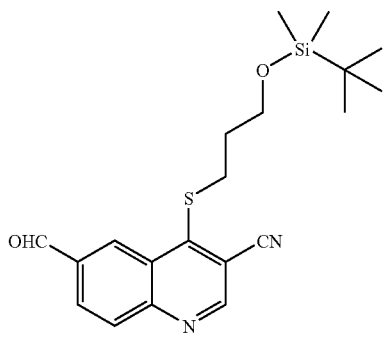

Similar procedure as described in example 37b was used, starting from 4-[3-(tert-butyl-dimethyl-silanyloxy)-propylsulfanyl]-6-iodo-quinoline-3-carbonitrile (example 50b), trethylamine, diphenylpropylphosphine (dpp), palladium(II) acetate, carbon monoxide and trihexylsilane to give 4-[3-(tert-butyl-dimethyl-silanyloxy)-propylsulfanyl]-6-formyl-quinoline-3-carbonitrile. LC-MS m/e 387 (MH+).

d) Preparation of 6-[2-amino-4-oxo-4H-thiazol-(5Z)-ylidenemethyl]-4-(3-hydroxy-propylsulfanyl)-quinoline-3-carbonitrile The suspension of 4-[3-(tert-butyl-dimethyl-silanyloxy)-propylsulfanyl]-6-formyl-quinoline-3-carbonitrile (example 50c, 200 mg, 0.52 mmol), pseudothiohydantoin (81 mg, 0.52 mmol) and sodium acetate (170 mg, 2.1 mmol) was stirred for 10 min. To the above solution was added acetic acid (0.3 mL). The mixture was heated to 130° C. for 1 h. After cooling to room temperature, the ice water was added. The solid was collected by filtration, washed with water and saturated sodium carbonate and dried. Flash chromatography (Merck Silica gel 60, 230-400 mesh, 0%-10% methanol in methylene chloride in 30 min) afforded two products: 6-[2-amino-4-oxo-4H-thiazol-(5Z)-ylidenemethyl]-4-(3-hydroxy-propylsulfanyl)-quinoline-3-carbonitrile (34 mg, 18%) as a light yellow solid: LC-MS m/e 371 (MH+) and another product 6-[2-amino-4-oxo-4H-thiazol-(5Z)-ylidenemethyl]-4-[3-(tert-butyl-dimethyl-silanyloxy)-propylsulfanyl]-quinoline-3-carbonitrile (90 mg, 36%) as a light yellow solid: LC-MS m/e 485 (MH+).

Example 51

6-[2-amino-4-oxo-4H-thiazol-(5Z)-ylidenemethyl]-4-[3-(tert-butyl-dimethyl-silanyloxy)-propylsulfanyl]-quinoline-3-carbonitrile

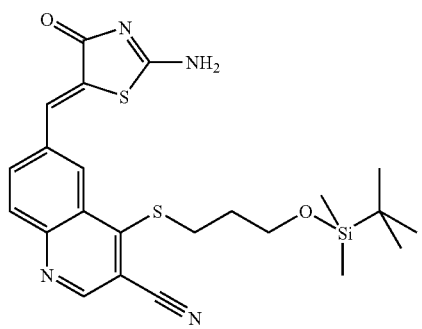

See example 50d for the preparation of 6-[2-amino-4-oxo-4H-thiazol-(5Z)-ylidenemethyl]-4-[3-(tert-butyl-dimethyl-silanyloxy)-propylsulfanyl]-quinoline-3-carbonitrile.

Example 52

6-[2-Amino-4-oxo-4H-thiazol-(5Z)-ylidenemethyl]-4-hexyl-quinoline-3-carbonitrile

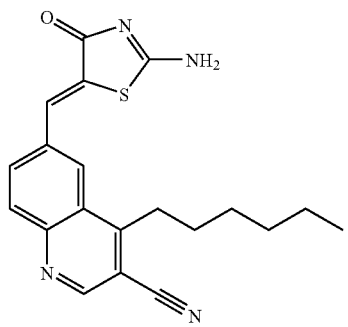

a) Preparation of 3-cyano-4-hexyl-quinoline-6-carboxylic acid ethyl ester

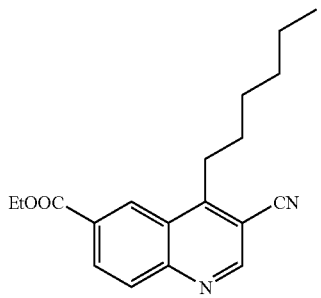

Similar procedure as described in example 46d was used, starting from 4-chloro-3-cyano-quinoline-6-carboxylic acid ethyl ester (example 46c), n-hexylboronic acid, sodium carbonate and POPd to give 3-cyano-4-hexyl-quinoline-6-carboxylic acid ethyl ester as a clear oil. LC-MS m/e 311 (MH$^+$).

b) Preparation of 4-hexyl-6-hydroxymethyl-1,4-dihydro-quinoline-3-carbonitrile

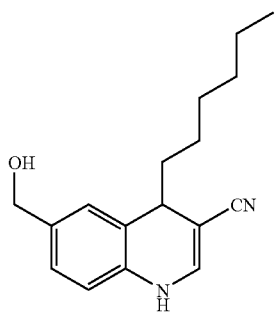

Similar procedure as described in example 46e was used, starting from 3-cyano-4-hexyl-quinoline-6-carboxylic acid ethyl ester (example 52a) and lithium borohydride to give 4-hexyl-6-hydroxymethyl-1,4-dihydro-quinoline-3-carbonitrile as a yellow solid. LC-MS m/e 271 (MH$^+$).

c) Preparation of 6-formyl-4-hexyl-quinoline-3-carbonitrile

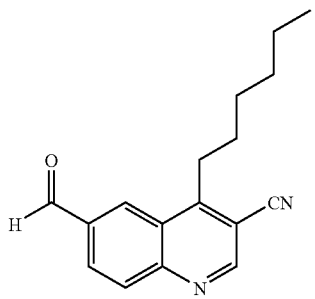

Similar procedure as described in example 46f was used, starting from 4-hexyl-6-hydroxymethyl-1,4-dihydro-quinoline-3-carbonitrile (example 52b) and manganese dioxide to give 6-formyl-4-hexyl-quinoline-3-carbonitrile as a white solid. LC-MS m/e 267 (MH$^+$).

d) Preparation of 6-[2-amino-4-oxo-4H-thiazol-(5Z)-ylidenemethyl]-4-hexyl-quinoline-3-carbonitrile Similar procedure as described in example 38 was used, starting from 6-formyl-4-hexyl-quinoline-3-carbonitrile (example 52c), pseudothiohydantoin, sodium acetate and acetic acid to give 6-[2-amino-4-oxo-4H-thiazol-(5Z)-ylidenemethyl]-4-hexyl-quinoline-3-carbonitrile. LC-MS m/e 365 (MH$^+$).

Example 53

6-[2-Amino-4-oxo-4H-thiazol-(5Z)-ylidenemethyl]-4-butylsulfanyl-quinoline-3-carbonitrile

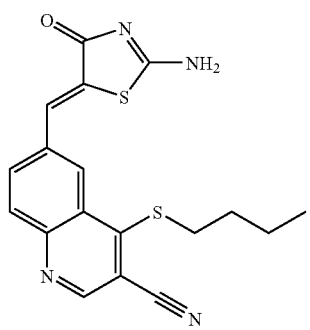

a) Preparation of 4-butylsulfanyl-6-iodo-quinoline-3-carbonitrile

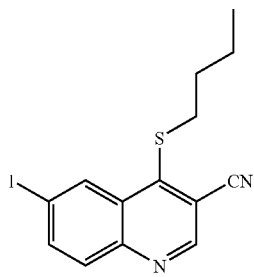

Similar procedure as described in example 39a was used, starting from 4-chloro-6-iodo-quinoline-3-carbonitrile (example 14c), butane-1-thiol and DIEA to give 4-butylsulfanyl-6-iodo-quinoline-3-carbonitrile. LC-MS m/e 369 (MH$^+$).

b) Preparation of
4-butylsulfanyl-6-formyl-quinoline-3-carbonitrile

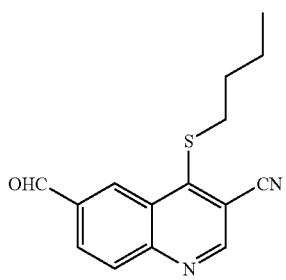

Similar procedure as described in example 37b was used, starting from 4-butylsulfanyl-6-iodo-quinoline-3-carbonitrile (example 53a), triethylamine, diphenylpropylphosphine (dpp), palladium(II) acetate, carbon monoxide and trihexylsilane to give 4-butylsulfanyl-6-formyl-quinoline-3-carbonitrile. LC-MS m/e 271 (MH$^+$).

c) Preparation of 6-[2-amino-4-oxo-4H-thiazol-(5Z)-ylidenemethyl]-4-butylsulfanyl-quinoline-3-carbonitrile Similar procedure as described in example 38 was used, starting from 4-butylsulfanyl-6-formyl-quinoline-3-carbonitrile (example 53b), pseudothiohydantoin, sodium acetate and acetic acid to give 6-[2-amino-4-oxo-4H-thiazol-(5Z)-ylidenemethyl]-4-butylsulfanyl-quinoline-3-carbonitrile. LC-MS m/e 367 (MH$^+$).

Example 54

6-[2-Amino-4-oxo-4H-thiazol-(5Z)-ylidenemethyl]-4-ethylsulfanyl-quinoline-3-carbonitrile

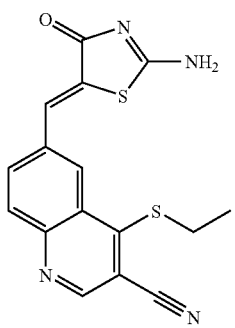

a) Preparation of
4-ethylsulfanyl-6-iodo-quinoline-3-carbonitrile

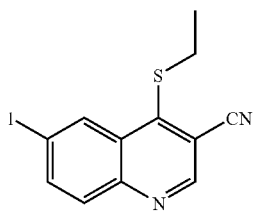

Similar procedure as described in example 39a was used, starting from 4-chloro-6-iodo-quinoline-3-carbonitrile (example 14c), ethanethiol and DIEA to give 4-ethylsulfanyl-6-iodo-quinoline-3-carbonitrile. LC-MS m/e 341 (MH$^+$).

b) Preparation of
4-ethylsulfanyl-6-formyl-quinoline-3-carbonitrile

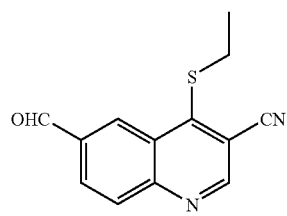

Similar procedure as described in example 37b was used, starting from 4-ethylsulfanyl-6-iodo-quinoline-3-carbonitrile (example 54a), triethylamine, diphenylpropylphosphine (dpp), palladium(II) acetate, carbon monoxide and trihexylsilane to give 4-ethylsulfanyl-6-formyl-quinoline-3-carbonitrile. LC-MS m/e 243 (MH$^+$).

c) Preparation of 6-[2-amino-4-oxo-4H-thiazol-(5Z)-ylidenemethyl]-4-ethylsulfanyl-quinoline-3-carbonitrile Similar procedure as described in example 38 was used, starting from 4-ethylsulfanyl-6-formyl-quinoline-3-carbonitrile (example 54b), pseudothiohydantoin, sodium acetate and acetic acid to give 6-[2-amino-4-oxo-4H-thiazol-(5Z)-ylidenemethyl]-4-ethylsulfanyl-quinoline-3-carbonitrile. LC-MS m/e 341 (MH$^+$).

Example 55

6-[2-Amino-4-oxo-4H-thiazol-(5Z)-ylidenemethyl]-4-methylsulfanyl-quinoline-3-carbonitrile

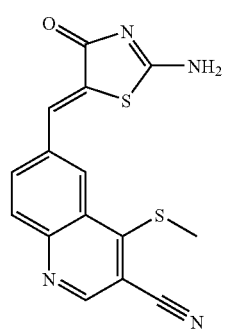

a) Preparation of 6-iodo-4-methylsulfanyl-quinoline-3-carbonitrile

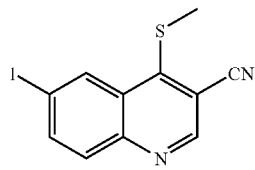

Similar procedure as described in example 39a was used, starting from 4-chloro-6-iodo-quinoline-3-carbonitrile (example 14c), methanethiol and DIEA to give 6-iodo-4-methylsulfanyl-quinoline-3-carbonitrile. LC-MS m/e 327 (MH$^+$).

b) Preparation of 6-formyl-4-methylsulfanyl-quinoline-3-carbonitrile

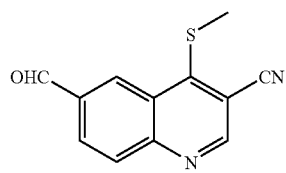

Similar procedure as described in example 37b was used, starting from 6-iodo-4-methylsulfanyl-quinoline-3-carbonitrile (example 55a), triethylamine, diphenylpropylphosphine (dpp), palladium(II) acetate, carbon monoxide and trihexylsilane to give 6-formyl-4-methylsulfanyl-quinoline-3-carbonitrile. LC-MS m/e 229 (MH$^+$).

c) Preparation of 6-[2-amino-4-oxo-4H-thiazol-(5Z)-ylidenemethyl]-4-methylsulfanyl-quinoline-3-carbonitrile Similar procedure as described in example 38 was used, starting from 6-formyl-4-methylsulfanyl-quinoline-3-carbonitrile (example 55b), pseudothiohydantoin, sodium acetate and acetic acid to give 6-[2-amino-4-oxo-4H-thiazol-(5Z)-ylidenemethyl]-4-methylsulfanyl-quinoline-3-carbonitrile. LC-MS m/e 327 (MH$^+$).

Example 56

4-Isopropoxy-6-[4-oxo-2-[(thiophen-2-ylmethyl)-amino]-4H-thiazol-(5Z)-ylidenemethyl]-quinoline-3-carbonitrile

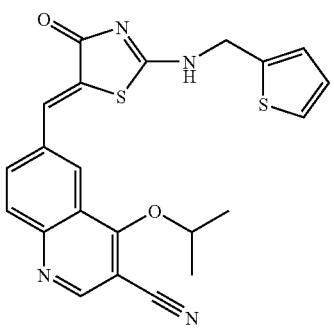

Similar procedure as described in example 41c was used, starting from 4-isoproxy-6-[2-methylsulfanyl-4-oxo-4H-thiazol-(5Z)-ylidenemethyl]-quinoline-3-carbonitrile (example 41b), 2-thiophenemethylamine and DIEA. After the reaction was completed, the solid was collected by filtration, washed with a little bit of acetonitrile and dried. Flash chromatography (Merck Silica gel 60, 230-400 mesh, 0%-5% methanol in methylene chloride in 30 min) afforded 4-isopropoxy-6-[4-oxo-2-[(thiophen-2-ylmethyl)-amino]-4H-thiazol-(5Z)-ylidenemethyl]-quinoline-3-carbonitrile. LC-MS m/e 435 (MH$^+$).

Example 57

6-[2-Amino-4-oxo-4H-thiazol-(5Z)-ylidenemethyl]-4-cyclopropyl-quinoline-3-carbonitrile

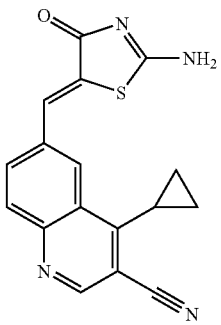

a) Preparation of 3-cyano-4-cyclopropyl-quinoline-6-carboxylic acid ethyl ester

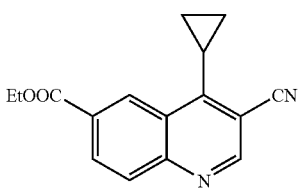

Similar procedure as described in example 46d was used, starting from 4-chloro-3-cyano-quinoline-6-carboxylic acid ethyl ester (example 46c), cyclopropylboronic acid, sodium carbonate and POPd to give 3-cyano-4-cyclopropyl-quinoline-6-carboxylic acid ethyl ester as colorless oil. LC-MS m/e 267 (MH+).

b) Preparation of 4-cyclopropyl-6-hydroxymethyl-1,4-dihydro-quinoline-3-carbonitrile

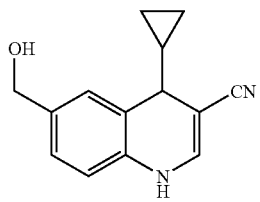

Similar procedure as described in example 46e was used, starting from 3-cyano-4-cyclopropyl-quinoline-6-carboxylic acid ethyl ester (example 57a) and lithium borohydride to give 4-cyclopropyl-6-hydroxymethyl-1,4-dihydro-quinoline-3-carbonitrile as a yellow solid. LC-MS m/e 227 (MH+).

c) Preparation of 4-cyclopropyl-6-formyl-quinoline-3-carbonitrile

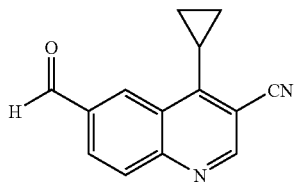

Similar procedure as described in example 46f was used, starting from 4-cyclopropyl-6-hydroxymethyl-1,4-dihydro-quinoline-3-carbonitrile (example 57b) and manganese dioxide to give 4-cyclopropyl-6-formyl-quinoline-3-carbonitrile as a white solid. LC-MS m/e 223 (MH+).

d) Preparation of 6-[2-amino-4-oxo-4H-thiazol-(5Z)-ylidenemethyl]-4-cyclopropyl-quinoline-3-carbonitrile Similar procedure as described in example 38 was used, starting from 4-cyclopropyl-6-formyl-quinoline-3-carbonitrile (example 57c), pseudothiohydantoin, sodium acetate and acetic acid to give 6-[2-amino-4-oxo-4H-thiazol-(5Z)-ylidenemethyl]-4-cyclopropyl-quinoline-3-carbonitrile. LC-MS m/e 321 (MH+).

Example 58

6-[2-(2-Hydroxy-1-hydroxymethyl-ethylamino)-4-oxo-4H-thiazol-(5Z)-ylidenemethyl]-4-isopropoxy-quinoline-3-carbonitrile

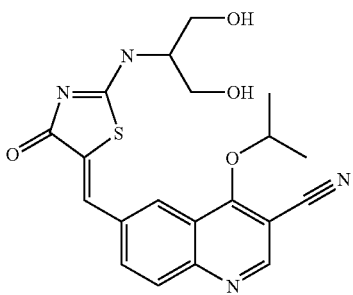

Similar procedure as described in example 41c was used, starting from 4-isoproxy-6-[2-methylsulfanyl-4-oxo-4H-thiazol-(5Z)-ylidenemethyl]-quinoline-3-carbonitrile (example 41b), 2-amino-propane-1,3-diol and DIEA. After the reaction was completed, the solid was collected by filtration, washed with a little bit of acetonitrile and dried. Flash chromatography (Merck Silica gel 60, 230-400 mesh, 0%-5% methanol in methylene chloride in 30 min) afforded 6-[2-(2-hydroxy-1-hydroxymethyl-ethylamino)-4-oxo-4H-thiazol-(5Z)-ylidenemethyl]-4-isopropoxy-quinoline-3-carbonitrile. LC-MS m/e 413 (MH+).

Example 59

6-[2-Hydrazino-4-oxo-4H-thiazol-(5Z)-ylidenemethyl]-4-isopropoxy-quinoline-3-carbonitrile

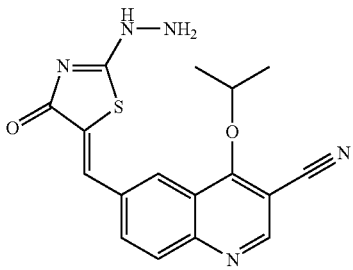

To the solution of 4-isoproxy-6-[2-methylsulfanyl-4-oxo-4H-thiazol-(5Z)-ylidenemethyl]-quinoline-3-carbonitrile (example 41b, 73 mg, 0.2 mmol) and diisopropylethylamine (0.104 mL, 0.6 mmol) in acetonitrile (3 mL), anhydrous hydrazine (0.014 mL, 0.4 mmol) in acetonitrile (1 mL) was slowly added. The resulted reaction mixture was stirred at room temperature for 1 hour. After the reaction was completed, solvent was removed. Flash chromatography (Merck Silica gel 60, 230-400 mesh, 0%-20% methanol in methylene chloride in 40 min) afforded 6-[2-hydrazino-4-oxo-4H-thiazol-(5Z)-ylidenemethyl]-4-isopropoxy-quinoline-3-carbonitrile. LC-MS m/e 354 (MH+).

Example 60

6-[2-Hydrazino-4-oxo-4H-thiazol-(5Z)-ylidenemethyl]-4-isopropoxy-quinoline-3-carbonitrile hydrochloride salt

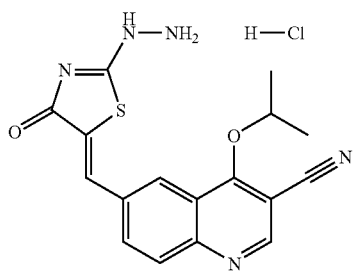

To the solution of 6-[2-hydrazino-4-oxo-4H-thiazol-(5Z)-ylidenemethyl]-4-isopropoxy-quinoline-3-carbonitrile (example 59, 15 mg, 0.042 mmol) in acetonitrile and water (8 mL), hydrochloride acid (1N, 0.17 mL) was added. The reaction completed by stirring the above mixture at room temperature for a short period of time. Then the solvents and excess hydrochloride acid were removed by vacuum and lyophilizer to give 6-[2-hydrazino-4-oxo-4H-thiazol-(5Z)-ylidenemethyl]-4-isopropoxy-quinoline-3-carbonitrile hydrochloride salt. LC-MS m/e 354 (MH$^+$).

Example 61

2-Amino-5-[1-(3-methanesulfonyl-4-phenyl-quinolin-6-yl)-meth-(Z)-ylidene]-thiazol-4-one

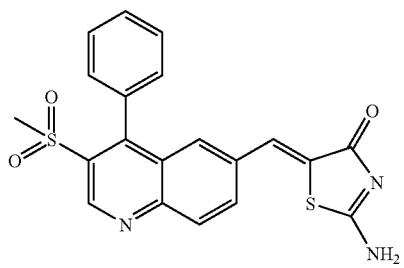

a) Preparation of methylsulfanyl-acetic acid ethyl ester

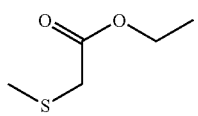

A solution of ethyl bromoacetate (167 g, 1 mol) and sodium thiomethoxide (20%, 367.5 g, 1.05 mol) in ethanol (500 mL) was heated at refluxing temperature for 5 hours. After cooling to the room temperature, most of the solvent was evaporated under reduced pressure, and then water was added. The resulted mixture was extracted with ethyl acetate. The organic layers were collected, dried over sodium sulfate, filtered, and concentrated to give methylsulfanyl-acetic acid ethyl ester (73.4 g, 55%) as colorless oil. LC-MS m/e 135 (MH$^+$).

b) Preparation of methanesulfonyl-acetic acid ethyl ester

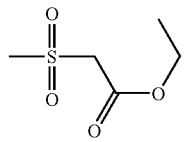

To the solution of methylsulfanyl-acetic acid ethyl ester (example 61a, 73.4 g, 0.547 mol) in methylene chloride (1000 mL), 3-chloroperoxybenzoic acid (m-CPBA, 217 g, 1.094 mol) was added in portions to maintain the temperature under 10 degrees. After addition, the reaction mixture was allowed to stir at about room temperature for 24 hours. After the reaction, the solid was filtered, the filtrate was neutralized with potassium carbonate to pH=7. The organic layer was collected, washed with brine, dried over sodium sulfate, and then concentrated in vacuo to give methanesulfonyl-acetic acid ethyl ester (90 g, 100%) as a solid. LC-MS m/e 167 (MH$^+$).

c) Preparation of 3-ethoxy-2-methanesulfonyl-acrylic acid ethyl ester

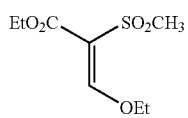

A mixture of methanesulfonyl-acetic acid ethyl ester (example 61b) (90 g, 0.547 mol), triethyl orthoformate (242.9 g, 0.641 mol), and acetic anhydride (227 mL) was heated at 130-140° C. for three hours. After cooling the reaction to room temperature, solvent was removed under reduced pressure to give 3-ethoxy-2-methanesulfonyl-acrylic acid ethyl ester (purity 50%). The crude compound was used in the following reaction without further purification. LC-MS m/e 223 (MH$^+$).

d) Preparation of 4-(2-ethoxycarbonyl-2-methanesulfonyl-vinylamino)-benzoic acid ethyl ester

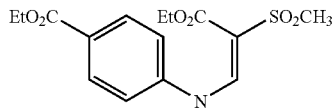

The compound of 3-ethoxy-2-methanesulfonyl-acrylic acid ethyl ester (example 61c, 52 g, 0.234 mol) and aniline (38.65 g, 0.234 mol) was mixed and heated at 140-150° C. under stirring for two hours. After cooling the reaction to room temperature, solvent was removed to give 4-(2-ethoxycarbonyl-2-methanesulfonyl-vinylamino)-benzoic acid ethyl ester. The crude compound was used in the following reaction without further purification. LC-MS m/e 342 (MH$^+$).

e) Preparation of 4-hydroxy-3-methanesulfonyl-quinoline-6-carboxylic acid ethyl ester

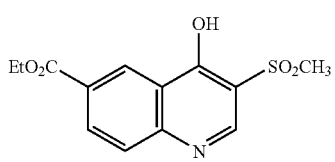

To the solution of 4-(2-ethoxycarbonyl-2-methanesulfonyl-vinylamino)-benzoic acid ethyl ester (example 61d) in phosphorous oxychloride (700 mL), Polyphosphoric acid (PPA, 445 g) was added. The resulted mixture was heated at 70 degrees for 8 hours under mechanical stirring. After the reaction, the reaction mixture was cooled to room temperature, and then phosphorous oxychloride was evaporated under reduced pressure. To the residue, water was added. The solid was filtered, collected, washed with water thoroughly, and then dried. Column chromatography gave 4-hydroxy-3-methanesulfonyl-quinoline-6-carboxylic acid ethyl ester (25 g, purity 70%). LC-MS m/e 232 (MH$^+$)

f) Preparation of 4-chloro-3-methanesulfonyl-quinoline-6-carboxylic acid ethyl ester

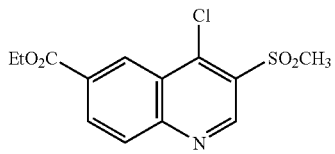

4-Hydroxy-3-methanesulfonyl-quinoline-6-carboxylic acid ethyl ester (example 61e, 15 g, 51 mmol) was dissolved in phosphorous oxychloride (450 mL). Then the reaction mixture was heated at the refluxing temperature for 6 hours. After cooling the reaction to about room temperature, the solvent was evaporated under reduced pressure. Dichloromethane was added to the residue, followed by extraction with water. The organic layers were collected, dried over sodium sulfate, filtered, and then concentrated in vacuo. Column chromatography gave 4-chloro-3-methanesulfonyl-quinoline-6-carboxylic acid ethyl ester (22 g, purity 70%). LC-MS m/e 250 (MH$^+$).

g) Preparation of 3-methanesulfonyl-4-phenyl-quinoline-6-carboxylic acid ethyl ester

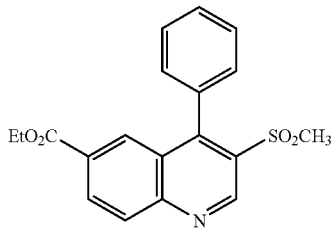

To the solution of 4-chloro-3-methanesulfonyl-quinoline-6-carboxylic acid ethyl ester (example 61f, 200 mg, 0.64 mmol) in DME (8 mL), phenylboronic acid (116 mg, 0.96 mmol), a catalytical amount of tetrakis(triphenylphosphine)-palladium(0) (147 mg, 0.13 mmol), and sodium carbonate solution (2 M, 1.12 ml, 2.23 mmol) were added. The resulted solution was heated under the microwave irradiation at 150 degrees for 15 min. After cooling to room temperature, the reaction mixture was filtered through a bed of celite with DME. The filtrate was quenched with water, and then extracted with ethyl acetate. The organic layers were collected, washed with brain, dried over sodium sulfate, and then concentrated in vacuo. Flash chromatography (Merck Silica gel 60, 70-230 mesh, 30%-50% ethyl acetate in hexane in 15 min, then 50% ethyl acetate in hexane in 9 min) afforded 3-methanesulfonyl-4-phenyl-quinoline-6-carboxylic acid ethyl ester (159 mg, 70%). LC-MS m/e 356 (MH$^+$).

h) Preparation of (3-methanesulfonyl-4-phenyl-quinolin-6-yl)-methanol

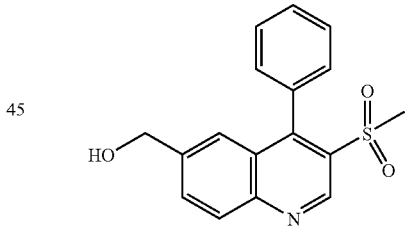

3-Methanesulfonyl-4-phenyl-quinoline-6-carboxylic acid ethyl ester (example 61g, 100 mg, 0.28 mmol) in anhydrous tetrahydrofuran (8 mL) was cooled to 0° C. First portion of diisobutylaminum hydride in THF (1 M, 930 uL, 0.93 mmol) was added to the above mixture, and the reaction went for 1 hr at about room temperature. Then the reaction was cooled to 0° C., and second portion of diisobutylaluminum hydride in THF (1 M, 930 uL, 0.93 mmol) was added. The reaction continued for another 45 min at about room temperature. The completion of the reaction was monitored using LC-MS. Additional portion of diisobutylaluminum hydride in THF (1 M, 620 uL, 0.62 mmol) was added, and the reaction went for another 30 min. The reaction was quenched with saturated sodium bicarbonate solution, followed by extraction with ethyl acetate. The organic solution was filtered through a bed of celit with ethyl acetate. The filtrate was collected, washed with water, brain, dried over sodium sulfate, filtered, and then concentrated in vacuo. Flash chromatography (Merck Silica gel 60, 70-230 mesh, 60% ethyl acetate in hexane in 10 min, then 60%-100% ethyl acetate in hexane in 13 min) afforded (3-methanesulfonyl-4-phenyl-quinolin-6-yl)-methanol (70 mg, 79%). LC-MS m/e 314 (MH+).

i) Preparation of 3-methanesulfonyl-4-phenyl-quinoline-6-carbaldehyde

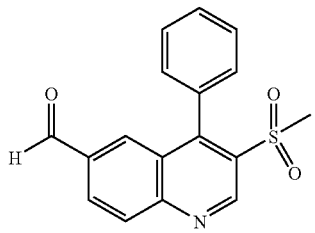

To the solution of (3-methanesulfonyl-4-phenyl-quinolin-6-yl)-methanol (example 61 h, 90 mg, 0.29 mmol) in methylene chloride (10 ml), activated manganese oxide (250 mg, 2.88 mmol) was added. The reaction mixture was heated at the refluxing temperature for 45 min. After cooling to the room temperature, the reaction mixture was filtered through a bed of celit with methylene chloride. The filtrate was collected and concentrated in vacuo to give 3-methanesulfonyl-4-phenyl-quinoline-6-carbaldehyde. LC-MS m/e 312 (MH+).

j) Preparation of 5-(3-methanesulfonyl-4-phenyl-quinolin-6-ylmethylene)-2-thioxo-thiazolidin-4-one

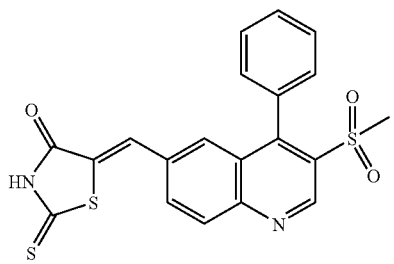

A mixture of 3-methanesulfonyl-4-phenyl-quinoline-6-carbaldehyde (example 61l,78 mg, 0.25 mmol), rhodanine (67 mg, 0.50 mmol), sodium acetate (82 mg, 1.0 mmol), and acetic acid (2.5 mL) was heated under the microwave irradiation at 160 degrees for 40 min. After cooling to about room temperature, the reaction mixture was filtered, and the solid was collected, washed with water, dried to give 5-(3-methanesulfonyl-4-phenyl-quinolin-6-ylmethylene)-2-thioxo-thiazolidin-4-one (82 mg, 76%) with a yellow color. LC-MS m/e 427 (MH+).

k) Preparation of 5-(3-methanesulfonyl-4-phenyl-quinolin-6-ylmethylene)-2-methylsulfanyl-thiazol-4-one

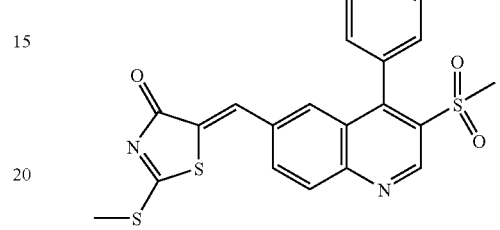

Similar procedure as described in example 41b was used, starting from 5-(3-methanesulfonyl-4-phenyl-quinolin-6-ylmethylene)-2-thioxo-thiazolidin-4-one (example 61j), iodomethane, and DIEA (diisopropylethylamine) in acetonitrile to give 5-(3-methanesulfonyl-4-phenyl-quinolin-6-ylmethylene)-2-methylsulfanyl-thiazol-4-one. LC-MS m/e 441 (MH+).

l) Preparation of 2-amino-5-[1-(3-methanesulfonyl-4-phenyl-quinolin-6-yl)-meth-(Z)-ylidene]-thiazol-4-one Similar procedure as described in example 41c was used, starting from 5-(3-methanesulfonyl-4-phenyl-quinolin-6-ylmethylene)-2-methylsulfanyl-thiazol-4-one (example 61k), and ammonia in methanol to give 2-amino-5-[1-(3-methanesulfonyl-4-phenyl-quinolin-6-yl)-meth-(Z)-ylidene]-thiazol-4-one. LC-MS m/e 410 (MH+).

Example 62

6-[2-Amino-4-oxo-4H-thiazol-(5Z)-ylidenemethyl]-4-phenyl-quinoline-3-carbonitrile

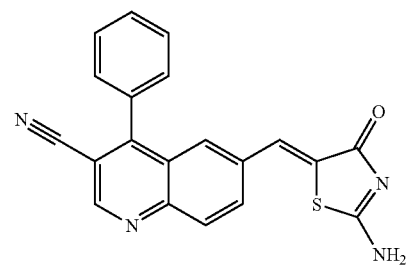

a) Preparation of 3-cyano-4-phenyl-quinoline-6-carboxylic acid ethyl ester

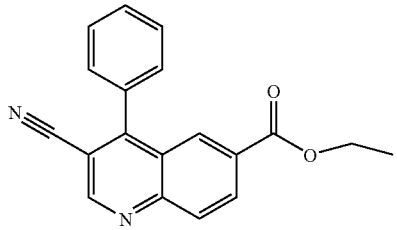

Similar procedure as described in example 61g was used, starting from 4-chloro-3-cyano-quinoline-6-carboxylic acid ethyl ester (example 46c), phenylboronic acid, tetrakis(triphenylphosphine)palladium(0), and sodium carbonate solution to give 3-cyano-4-phenyl-quinoline-6-carboxylic acid ethyl ester. LC-MS m/e 303 (MH$^+$).

b) Preparation of 6-hydroxymethyl-4-phenyl-quinoline-3-carbonitrile

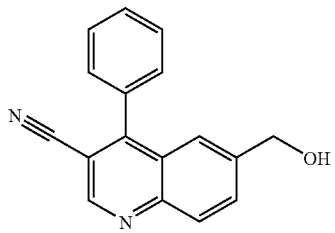

Similar procedure as described in example 61h was used, starting from 3-cyano-4-phenyl-quinoline-6-carboxylic acid ethyl ester (example 62a), and diisobutylaminum hydride to give 6-hydroxymethyl-4-phenyl-quinoline-3-carbonitrile. LC-MS m/e 261 (MH$^+$).

c) Preparation of 6-formyl-4-phenyl-quinoline-3-carbonitrile

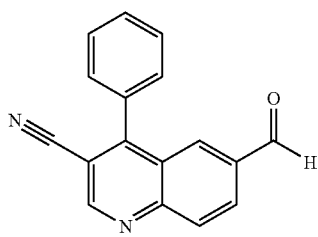

Similar procedure as described in example 61i was used, starting from 6-hydroxymethyl-4-phenyl-quinoline-3-carbonitrile (example 62b), and activated manganese oxide to give 6-formyl-4-phenyl-quinoline-3-carbonitrile. LC-MS m/e 259 (MH$^+$).

d) Preparation of 6-(2,4-dioxo-thiazolidin-5-ylidenemethyl)-4-phenyl-quinoline-3-carbonitrile

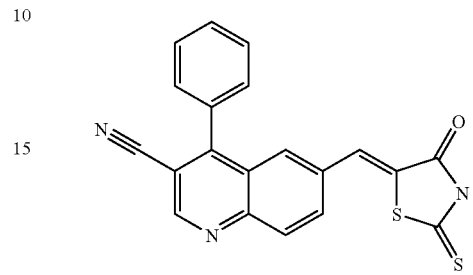

Similar procedure as described in example 61j was used, starting from 6-formyl-4-phenyl-quinoline-3-carbonitrile (example 62c), rhodanine, sodium acetate, and acetic acid to give 6-(2,4-dioxo-thiazolidin-5-ylidenemethyl)-4-phenyl-quinoline-3-carbonitrile. LC-MS m/e 374 (MH$^+$).

e) Preparation of 6-(2-methylsulfanyl-4-oxo-4H-thiazol-5-ylidenemethyl)-4-phenyl-quinoline-3-carbonitrile

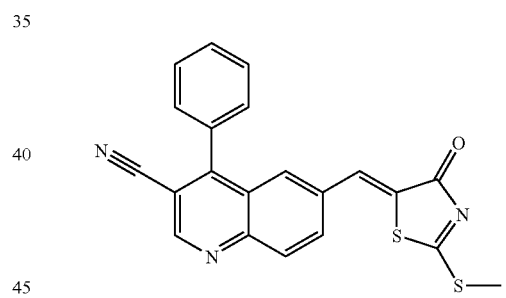

Similar procedure as described in example 41b was used, starting from 6-(2,4-dioxo-thiazolidin-5-ylidenemethyl)-4-phenyl-quinoline-3-carbonitrile (example 62d), iodomethane, and DIEA (diisopropylethylamine) in acetonitrile to give 6-(2-methylsulfanyl-4-oxo-4H-thiazol-5-ylidenemethyl)-4-phenyl-quinoline-3-carbonitrile. LC-MS m/e 388 (MH$^+$).

f) Preparation of 6-[2-amino-4-oxo-4H-thiazol-(5Z)-ylidenemethyl]-4-phenyl-quinoline-3-carbonitrile Similar procedure as described in example 41c was used, starting from 6-(2-methylsulfanyl-4-oxo-4H-thiazol-5-ylidenemethyl)-4-phenyl-quinoline-3-carbonitrile (example 62e), and ammonia in methanol to give 6-[2-amino-4-oxo-4H-thiazol-(5Z)-ylidenemethyl]-4-phenyl-quinoline-3-carbonitrile. LC-MS m/e 357 (MH$^+$).

Example 63

6-[2-Amino-4-oxo-4H-thiazol-(5Z)-ylidenemethyl]-4-pyridin-3-yl-quinoline-3-carbonitrile; compound with trifluoro-acetic acid

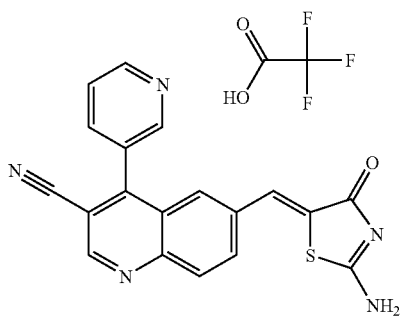

a) Preparation of 3-cyano-4-pyridin-3-yl-quinoline-6-carboxylic acid ethyl ester

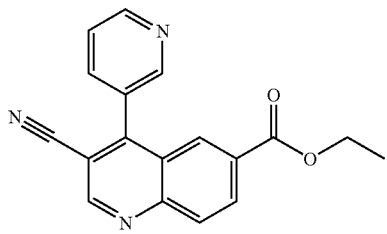

Similar procedure as described in example 61g was used, starting from 4-chloro-3-cyano-quinoline-6-carboxylic acid ethyl ester (example 46c), pyridine-3-boronic acid, tetrakis(triphenylphosphine)palladium(0), and sodium carbonate solution to give 3-cyano-4-pyridin-3-yl-quinoline-6-carboxylic acid ethyl ester. LC-MS m/e 304 (MH$^+$).

b) Preparation of 6-hydroxymethyl-4-pyridin-3-yl-quinoline-3-carbonitrile

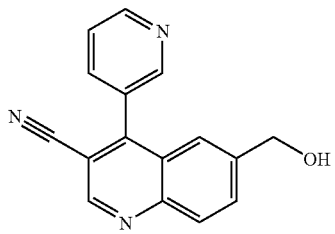

Similar procedure as described in example 61h was used, starting from 3-cyano-4-pyridin-3-yl-quinoline-6-carboxylic acid ethyl ester (example 63a), and diisobutylaluminum hydride to give 6-hydroxymethyl-4-pyridin-3-yl-quinoline-3-carbonitrile. LC-MS m/e 262 (MH$^+$).

c) Preparation of 6-formyl-4-pyridin-3-yl-quinoline-3-carbonitrile

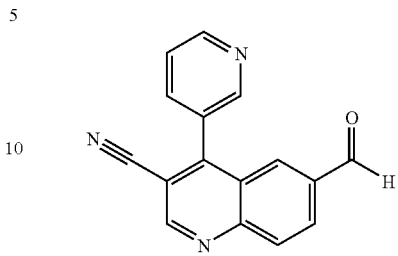

Similar procedure as described in example 61i was used, starting from 6-hydroxymethyl-4-pyridin-3-yl-quinoline-3-carbonitrile (example 63b), and activated manganese oxide to give 6-formyl-4-pyridin-3-yl-quinoline-3-carbonitrile. LC-MS m/e 260 (MH$^+$).

d) Preparation of 6-(4-oxo-2-thioxo-thiazolidin-5-ylidenemethyl)-4-pyridin-3-yl-quinoline-3-carbonitrile

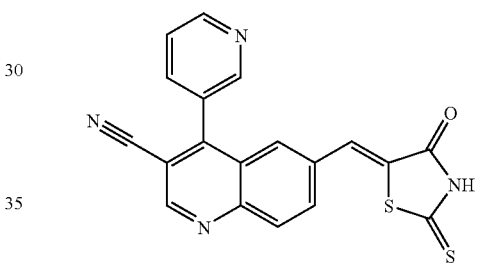

Similar procedure as described in example 61j was used, starting from 6-formyl-4-pyridin-3-yl-quinoline-3-carbonitrile (example 63c), rhodanine, sodium acetate, and acetic acid to give 6-(4-oxo-2-thioxo-thiazolidin-5-ylidenemethyl)-4-pyridin-3-yl-quinoline-3-carbonitrile. LC-MS m/e 375 (MH$^+$).

e) Preparation of 6-(2-methylsulfanyl-4-oxo-4H-thiazol-5-ylidenemethyl)-4-pyridin-3-yl-quinoline-3-carbonitrile

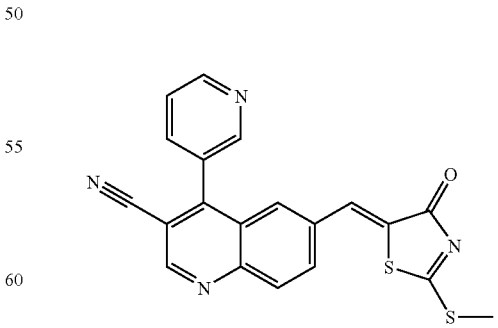

Similar procedure as described in example 41b was used, starting from 6-(4-oxo-2-thioxo-thiazolidin-5-ylidenemethyl)-4-pyridin-3-yl-quinoline-3-carbonitrile (example 63d), iodomethane, and DIEA (diisopropylethylamine) in acetonitrile to give 6-(2-methylsulfanyl-4-oxo-4H-thiazol-5-ylidenemethyl)-4-pyridin-3-yl-quinoline-3-carbonitrile. LC-MS m/e 389 (MH+).

f) Preparation of 6-[2-amino-4-oxo-4H-thiazol-(5Z)-ylidenemethyl]-4-pyridin-3-yl-quinoline-3-carbonitrile; compound with trifluoro-acetic acid Similar procedure as described in example 41c was used, starting from 6-(2-methylsulfanyl-4-oxo-4H-thiazol-5-ylidenemethyl)-4-pyridin-3-yl-quinoline-3-carbonitrile (example 63e), and ammonia in methanol to give 6-(2-amino-4-oxo-4H-thiazol-5-ylidenemethyl)-4-pyridin-3-yl-quinoline-3-carbonitrile. Flash chromatography using a small amount of trifluoroacetic acid as a cosolvent gave 6-[2-amino-4-oxo-4H-thiazol-(5Z)-ylidenemethyl]-4-pyridin-3-yl-quinoline-3-carbonitrile; compound with trifluoro-acetic acid. LC-MS m/e 358 (MH+).

Example 64

6-[2-Amino-4-oxo-4H-thiazol-(5Z)-ylidenemethyl]-4-(1-ethyl-propoxy)-quinoline-3-carbonitrile

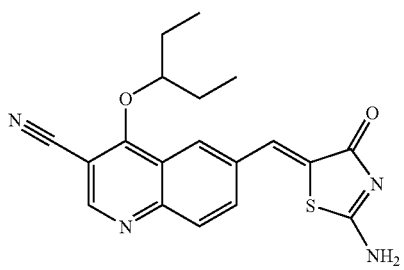

a) Preparation of 4-(1-ethyl-propoxy)-6-iodo-quinoline-3-carbonitrile

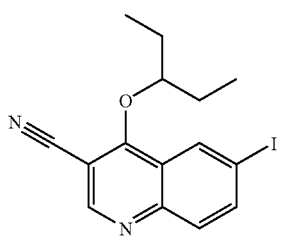

Similar procedure as described in example 28a was used, starting from 3-pentanol, 4-chloro-6-iodo-quinoline-3-carbonitrile (example 14c) and potassium hydride in a solvent system of THF to give 4-(1-ethyl-propoxy)-6-iodo-quinoline-3-carbonitrile. LC-MS m/e 367 (MH+).

b) Preparation of 4-(1-ethyl-propoxy)-6-formyl-quinoline-3-carbonitrile

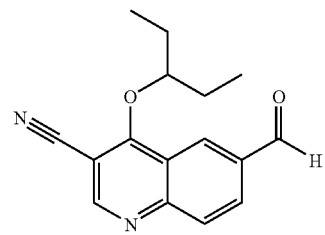

Similar procedure as described in example 28b was used, starting from 6-iodo-4-(2-methoxy-ethoxy)-quinoline-3-carbonitrile (example 64a), carbon monoxide, triethylamine, diphenylpropylphosphine, palladium(II) acetate and trihexylsilane to give 4-(1-ethyl-propoxy)-6-formyl-quinoline-3-carbonitrile. LC-MS m/e 269 (MH+).

c) Preparation of 6-[2-amino-4-oxo-4H-thiazol-(5Z)-ylidenemethyl]-4-(1-ethyl-propoxy)-quinoline-3-carbonitrile Similar procedure as described in example 28c was used, starting from 4-(1-ethyl-propoxy)-6-formyl-quinoline-3-carbonitrile (example 64b), pseudothiohydantoin, sodium acetate and acetic acid to give 6-[2-amino-4-oxo-4H-thiazol-(5Z)-ylidenemethyl]-4-(1-ethyl-propoxy)-quinoline-3-carbonitrile. LC-MS m/e 367 (MH+).

Example 65

6-[2-Amino-4-oxo-4H-thiazol-(5Z)-ylidenemethyl]-4-isobutylsulfanyl-quinoline-3-carbonitrile

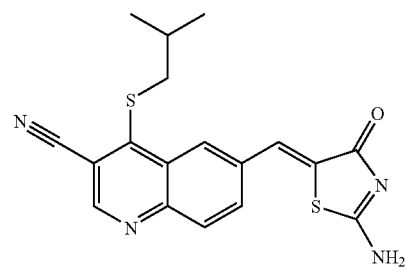

a) Preparation of 6-iodo-4-isobutylsulfanyl-quinoline-3-carbonitrile

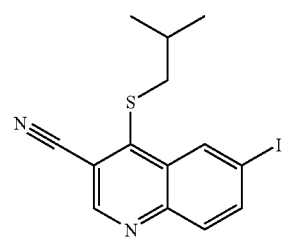

Similar procedure as described in example 28a was used, starting from 2-methyl-propane-1-thiol, 4-chloro-6-iodo-quinoline-3-carbonitrile (example 14c) and potassium hydride in a solvent system of tetrahydrofuran to give 6-iodo-4-isobutylsulfanyl-quinoline-3-carbonitrile. LC-MS m/e 369(MH⁺).

b) Preparation of 6-formyl-4-isobutylsulfanyl-quinoline-3-carbonitrile

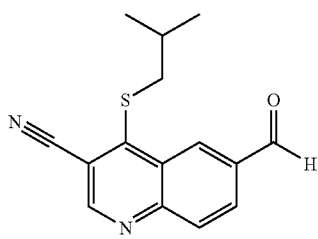

Similar procedure as described in example 28b was used, starting from 6-iodo-4-isobutylsulfanyl-quinoline-3-carbonitrile (example 65a), carbon monoxide, triethylamine, diphenylpropylphosphine, palladium (II) acetate and trihexylsilane to give 6-formyl-4-isobutylsulfanyl-quinoline-3-carbonitrile. LC-MS m/e 271 (MH⁺).

c) Preparation of 6-[2-amino-4-oxo-4H-thiazol-(5Z)-ylidenemethyl]-4-isobutylsulfanyl-quinoline-3-carbonitrile

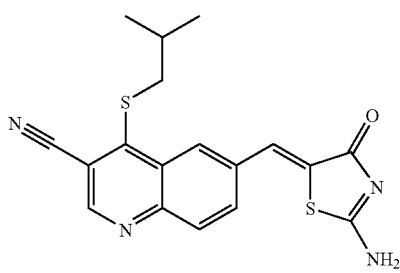

Similar procedure as described in example 28c was used, starting from 6-formyl-4-isobutylsulfanyl-quinoline-3-carbonitrile (example 65b), pseudothiohydantoin, sodium acetate and acetic acid to give 6-[2-amino-4-oxo-4H-thiazol-(5Z)-ylidenemethyl]-4-isobutylsulfanyl-quinoline-3-carbonitrile. LC-MS m/e 369 (MH⁺).

Example 66

6-[2-Amino-4-oxo-4H-thiazol-(5Z)-ylidenemethyl]-4-isobutoxy-quinoline-3-carbonitrile

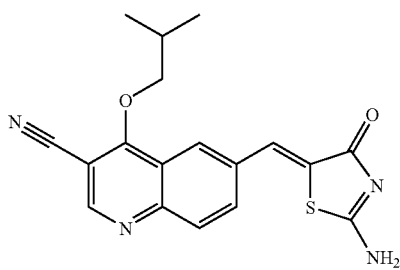

a) Preparation of 6-iodo-4-isobutoxy-quinoline-3-carbonitrile

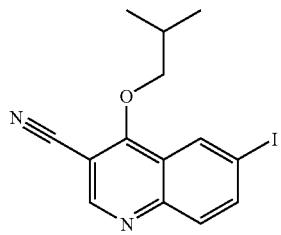

Similar procedure as described in example 28a was used, starting from 2-methyl-propan-1-ol, 4-chloro-6-iodo-quinoline-3-carbonitrile (example 14c) and potassium hydride in a solvent system of THF to give 6-iodo-4-isobutoxy-quinoline-3-carbonitrile. LC-MS m/e 353(MH⁺).

b) Preparation of 6-formyl-4-isobutoxy-quinoline-3-carbonitrile

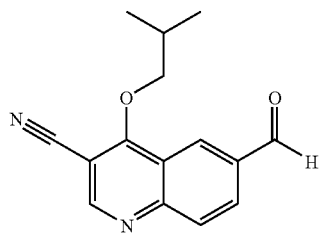

Similar procedure as described in example 28b was used, starting from 6-iodo-4-isobutoxy-quinoline-3-carbonitrile (example 66a), carbon monoxide, triethylamine, diphenylpropylphosphine, palladium (II) acetate and trihexylsilane to give 6-formyl-4-isobutoxy-quinoline-3-carbonitrile. LC-MS m/e 255 (MH⁺).

c) Preparation of 6-[2-amino-4-oxo-4H-thiazol-(5Z)-ylidenemethyl]-4-isobutoxy-quinoline-3-carbonitrile Similar procedure as described in example 28c was used, starting from 6-formyl-4-isobutoxy-quinoline-3-carbonitrile (example 66b), pseudothiohydantoin, sodium acetate and acetic acid to give 6-[2-amino-4-oxo-4H-thiazol-(5Z)-ylidenemethyl]-4-isobutoxy-quinoline-3-carbonitrile. LC-MS m/e 353 (MH⁺).

Example 67

6-[2-Amino-4-oxo-4H-thiazol-(5Z)-ylidenemethyl]-4-(2,2-dimethyl-propoxy)-quinoline-3-carbonitrile

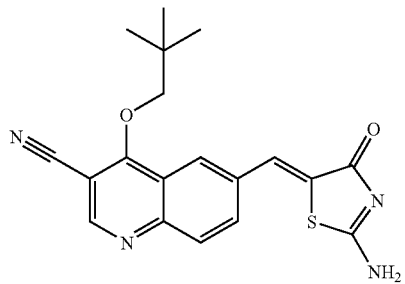

a) Preparation of 4-(2,2-dimethyl-propoxy)-6-iodo-quinoline-3-carbonitrile

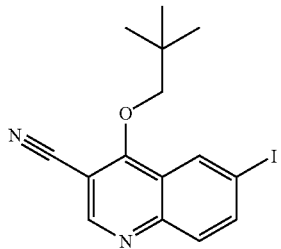

Similar procedure as described in example 28a was used, starting from 2,2-dimethyl-1-propanol, 4-chloro-6-iodo-quinoline-3-carbonitrile (example 14c) and potassium hydride in a solvent system of THF to give 4-(2,2-dimethyl-propoxy)-6-iodo-quinoline-3-carbonitrile. LC-MS m/e 367 (MH$^+$).

b) Preparation of 4-(2,2-dimethyl-propoxy)-6-formyl-quinoline-3-carbonitrile

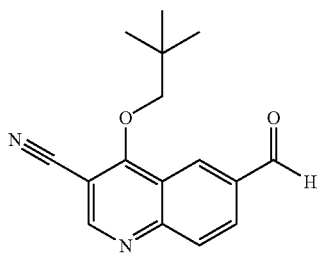

Similar procedure as described in example 28b was used, starting from 4-(2,2-dimethyl-propoxy)-6-iodo-quinoline-3-carbonitrile (example 67a), carbon monoxide, triethylamine, diphenylpropylphosphine, palladium(II) acetate and trihexylsilane to give 4-(2,2-dimethyl-propoxy)-6-formyl-quinoline-3-carbonitrile. LC-MS m/e 269 (MH$^+$).

c) Preparation of 6-[2-amino-4-oxo-4H-thiazol-(5Z)-ylidenemethyl]-4-(2,2-dimethyl-propoxy)-quinoline-3-carbonitrile Similar procedure as described in example 28c was used, starting from 4-(2,2-dimethyl-propoxy)-6-formyl-quinoline-3-carbonitrile (example 67b), pseudothiohydantoin, sodium acetate and acetic acid to give 6-[2-amino-4-oxo-4H-thiazol-(5Z)-ylidenemethyl]-4-(2,2-dimethyl-propoxy)-quinoline-3-carbonitrile. LC-MS m/e 367 (MH$^+$).

Example 67

6-[2-Cyclopropylamino-4-oxo-4H-thiazol-(5Z)-ylidenemethyl]-4-(1-ethyl-propoxy)-quinoline-3-carbonitrile

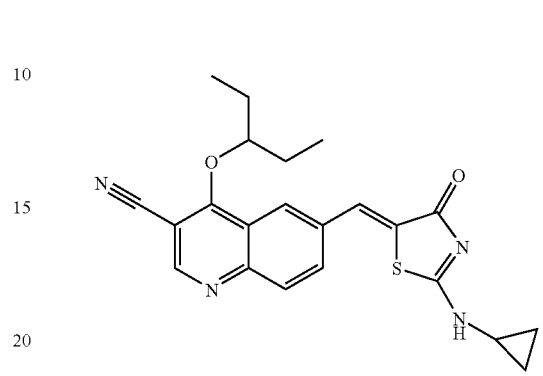

Similar procedure as described in example 28c was used, starting from 6-formyl-4-(tetrahydro-pyran-4-yloxy)-quinoline-3-carbonitrile (example 64b), 2-cyclopropylamino-thiazol-4-one (example 37c), sodium acetate and acetic acid to give 6-[2-cyclopropylamino-4-oxo-4H-thiazol-(5Z)-ylidenemethyl]-4-(1-ethyl-propoxy)-quinoline-3-carbonitrile. LC-MS m/e 407 (MH$^+$).

Example 69

6-[2-Cyclopropylamino-4-oxo-4H-thiazol-(5Z)-ylidenemethyl]-4-isobutoxy-quinoline-3-carbonitrile

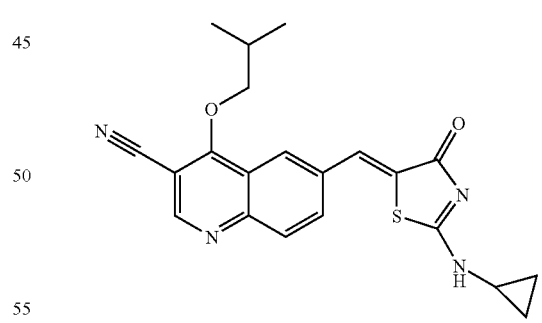

Similar procedure as described in example 28c was used, starting from 6-formyl-4-isobutoxy-quinoline-3-carbonitrile (example 66b), 2-cyclopropylamino-thiazol-4-one (example 37c), sodium acetate and acetic acid to give 6-[2-cyclopropylamino-4-oxo-4H-thiazol-(5Z)-ylidenemethyl]-4-isobutoxy-quinoline-3-carbonitrile. LC-MS m/e 393 (MH$^+$).

Example 70

6-[2-Cyclopropylamino-4-oxo-4H-thiazol-(5Z)-ylidenemethyl]-4-(2,2-dimethyl-propoxy)-quinoline-3-carbonitrile

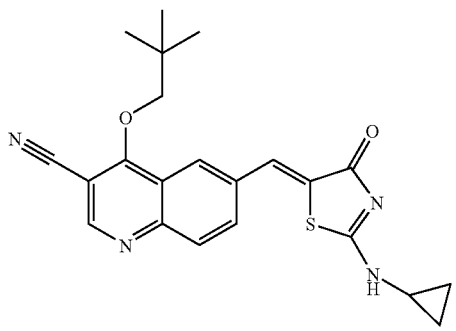

Similar procedure as described in example 28c was used, starting from 4-(2,2-dimethyl-propoxy)-6-formyl-quinoline-3-carbonitrile (example 67b), 2-cyclopropylamino-thiazol-4-one (example 37c), sodium acetate and acetic acid to give 6-[2-cyclopropylamino-4-oxo-4H-thiazol-(5Z)-ylidenemethyl]-4-(2,2-dimethyl-propoxy)-quinoline-3-carbonitrile. LC-MS m/e 407 (MH+).

Example 71

6-[2-Amino-4-oxo-4H-thiazol-(5Z)-ylidenemethyl]-4-propyl-quinoline-3-carbonitrile

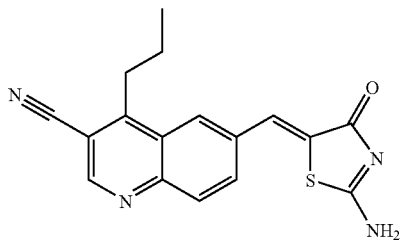

a) Preparation of 2-(3-cyano-6-iodo-quinolin-4-yl)-2-ethyl-malonic acid diethyl ester

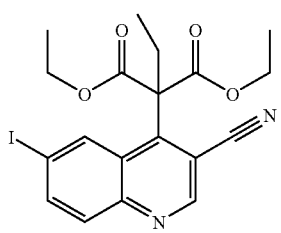

Potassium hydride (35% oil dispersion, 220 mg, 1.91 mmol) was washed with newly opened hexane for two times under Argon. Then anhydrous tetrahydrofuran (55 mL) was added, followed by addition of 2-ethyl-malonic acid diethyl ester (480 mg, 2.54 mmol). The reaction mixture was stirred at about room temperature for 10 min. Then 4-chloro-6-iodo-quinoline-3-carbonitrile (example 14c, 200 mg, 0.64 mmol) in anhydrous tetrahydrofuran (3 mL) was added to the above reaction mixture, and then reaction continued at room temperature for another 30 min. The reaction was quenched with ice water, and then extracted with ethyl acetate. The organic layers were collected, washed with brain, dried over sodium sulfate, filtered, and concentrated in vacuo. Flash chromatography (Merck Silica gel 60, 70-230 mesh, 20% ethyl acetate in hexane in 25 min) afforded 2-(3-cyano-6-iodo-quinolin-4-yl)-2-ethyl-malonic acid diethyl ester (250 mg, 85%) as colorless viscous oil. LC-MS m/e 467 (MH+).

b) Preparation of 6-iodo-4-propyl-quinoline-3-carbonitrile

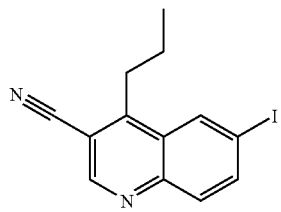

A mixture of 2-(3-cyano-6-iodo-quinolin-4-yl)-2-ethyl-malonic acid diethyl ester (example 71a, 250 mg, 0.54 mmol), lithium chloride (45 mg, 0.72 mmol), water (10 uL, 0.54 mmol), and dimethylsulfoxide (10 uL) was heated at 180 degrees for 1 hour. After cooling to the room temperature, the reaction was quenched with water, followed by addition of ethyl acetate. The insoluble material was removed by filtration through a plug of celit with ethyl acetate. The water layer was extracted with ethyl acetate two more times. The organic layers were combined, washed with brain, dried over sodium sulfate, filtered, and concentrated in vacuo to give the crude product as dark viscous oil. Flash chromatography (Merck Silica gel 60, 70-230 mesh, 10-20% ethyl acetate in hexane in 30 min) afforded 6-iodo-4-propyl-quinoline-3-carbonitrile (40 mg, 23%) as a solid. LC-MS m/e 323 (MH+).

c) Preparation of 6-formyl-4-propyl-quinoline-3-carbonitrile

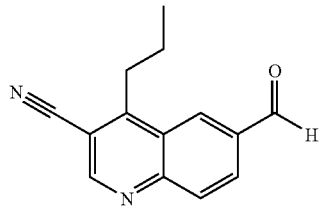

Similar procedure as described in example 28b was used, starting from 6-iodo-4-pentyl-quinoline-3-carbonitrile (example 71b), triethylamine, diphenylpropylphosphine, palladium(II) acetate and trihexylsilane to give 6-formyl-4-propyl-quinoline-3-carbonitrile. LC-MS m/e 225 (MH+).

d) Preparation of 6-[2-amino-4-oxo-4H-thiazol-(5Z)-ylidenemethyl]-4-propyl-quinoline-3-carbonitrile Similar procedure as described in example 28c was used, starting from 6-formyl-4-propyl-quinoline-3-carbonitrile (example 71c), pseudothiohydantoin, sodium acetate and acetic acid to give 6-[2-amino-4-oxo-4H-thiazol-(5Z)-ylidenemethyl]-4-propyl-quinoline-3-carbonitrile. LC-MS m/e 323 (MH+).

Example 72

6-[2-Amino-4-oxo-4H-thiazol-(5Z)-ylidenemethyl]-4-pentyl-quinoline-3-carbonitrile

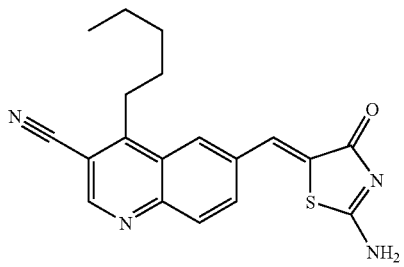

a) Preparation of 2-butyl-2-(3-cyano-6-iodo-quinolin-4-yl)-malonic acid diethyl ester

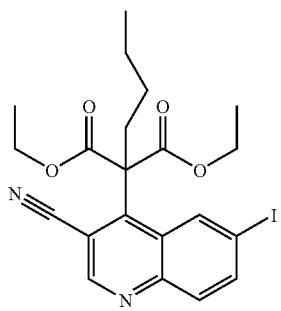

Similar procedure as described in example 71a was used, starting from 4-chloro-6-iodo-quinoline-3-carbonitrile (example 14c), diethyl n-butyl malonate, and potassium hydride to give 2-butyl-2-(3-cyano-6-iodo-quinolin-4-yl)-malonic acid diethyl ester. LC-MS m/e 495 (MH+).

b) Preparation of 6-iodo-4-pentyl-quinoline-3-carbonitrile

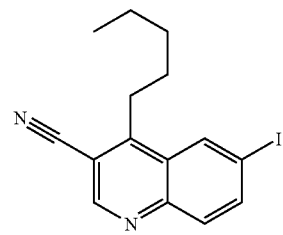

Similar procedure as described in example 71b was used, starting from 2-butyl-2-(3-cyano-6-iodo-quinolin-4-yl)-malonic acid diethyl ester (example 72a), lithium chloride, water, and dimethylsulfoxide to give 6-iodo-4-pentyl-quinoline-3-carbonitrile. LC-MS m/e 351 (MH+).

c) Preparation of 6-formyl-4-pentyl-quinoline-3-carbonitrile

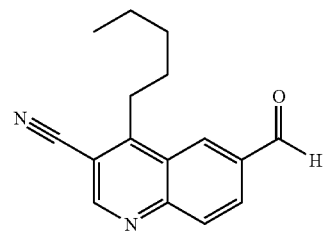

Similar procedure as described in example 28b was used, starting from 6-iodo-4-pentyl-quinoline-3-carbonitrile (example 72b), triethylamine, diphenylpropylphosphine, palladium(II) acetate and trihexylsilane to give 6-formyl-4-pentyl-quinoline-3-carbonitrile. LC-MS m/e 253 (MH+).

d) Preparation of 6-[2-amino-4-oxo-4H-thiazol-(5Z)-ylidenemethyl]-4-pentyl-quinoline-3-carbonitrile Similar procedure as described in example 28c was used, starting from 6-formyl-4-propyl-quinoline-3-carbonitrile (example 72c), pseudothiohydantoin, sodium acetate and acetic acid to give 6-[2-amino-4-oxo-4H-thiazol-(5Z)-ylidenemethyl]-4-pentyl-quinoline-3-carbonitrile. LC-MS m/e 351 (MH+).

Example 73

6-[2-Amino-4-oxo-4H-thiazol-(5Z)-ylidenemethyl]-4-methyl-quinoline-3-carbonitrile

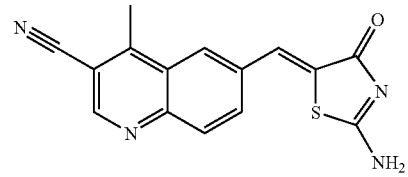

a) Preparation of 2-(3-cyano-6-iodo-quinolin-4-yl)-malonic acid diethyl ester

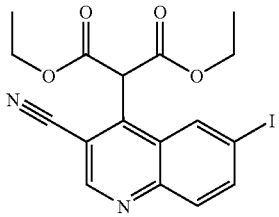

Similar procedure as described in example 71a was used, starting from 4-chloro-6-iodo-quinoline-3-carbonitrile (example 14c), malonate, and potassium hydride to give 2-(3-cyano-6-iodo-quinolin-4-yl)-malonic acid diethyl ester. LC-MS m/e 439 (MH⁺).

b) Preparation of 6-iodo-4-methyl-quinoline-3-carbonitrile

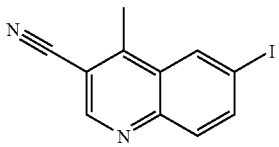

Similar procedure as described in example 71b was used, starting 2-(3-cyano-6-iodo-quinolin-4-yl)-malonic acid diethyl ester (example 73a), lithium chloride, water, and dimethylsulfoxide to give 6-iodo-4-methyl-quinoline-3-carbonitrile. LC-MS m/e 295 (MH⁺).

c) Preparation of 6-formyl-4-methyl-quinoline-3-carbonitrile

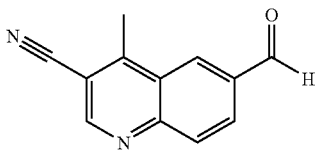

Similar procedure as described in example 28b was used, starting from 6-iodo-4-methyl-quinoline-3-carbonitrile (example 73b), triethylamine, diphenylpropylphosphine, palladium(II) acetate and trihexylsilane to give 6-formyl-4-methyl-quinoline-3-carbonitrile. LC-MS m/e 197 (MH⁺).

d) Preparation of 6-[2-amino-4-oxo-4H-thiazol-(5Z)-ylidenemethyl]-4-methyl-quinoline-3-carbonitrile Similar procedure as described in example 28c was used, starting from 6-formyl-4-methyl-quinoline-3-carbonitrile (example 73c), pseudothiohydantoin, sodium acetate and acetic acid to give 6-[2-amino-4-oxo-4H-thiazol-(5Z)-ylidenemethyl]-4-methyl-quinoline-3-carbonitrile. LC-MS m/e 295 (MH⁺).

Example 74

2-Cyclopropylamino-5-[1-(4-ethoxy-3-methanesulfonyl-quinolin-6-yl)-meth-(Z)-ylidene]-thiazol-4-one

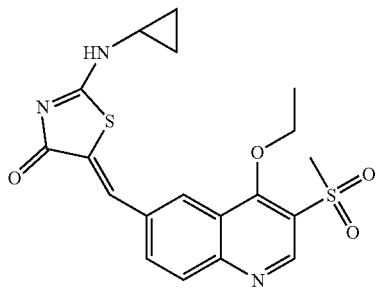

a) Preparation of 4-ethoxy-3-methanesulfonyl-quinoline-6-carboxylic acid ethyl ester

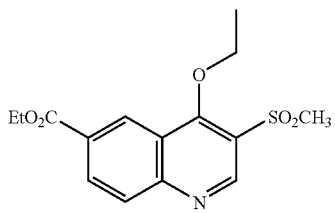

4-Chloro-3-methanesulfonyl-quinoline-6-carboxylic acid ethyl ester (example 61f, 7.96 g, 25.4 mmol) was dissolved in anhydrous alcohol (500 mL) which containing sodium ethoxide (3.45 g, 50.8 mmol). The mixture was heated at 60 degrees for 6 hours under stirring. After the reaction, the solvent was evaporated under reduced pressure, and then dichloromethane was added. After filtration, the filtrate was concentrated to give 4-ethoxy-3-methanesulfonyl-quinoline-6-carboxylic acid ethyl ester, which was used for next step without further purification. LC-MS m/e 324 (MH⁺).

b) Preparation of (4-ethoxy-3-methanesulfonyl-quinolin-6-yl)-methanol

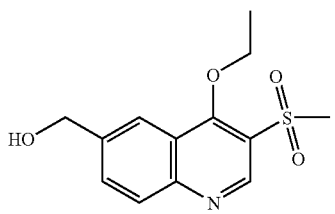

A solution of 4-ethoxy-3-methanesulfonyl-quinoline-6-carboxylic acid ethyl ester (example 74a) in anhydrous dichloromethane (500 mL) was cooled to −78 degrees by acetone and dry-ice bath. DIBAL-H in toluene (1M, 50.8 mL, 50.8 m mol) was added dropwise into the above solution. The solution was allowed to react at −78 degrees for 4 hours. Then methanol was added to the reaction mixture. The resulted reaction mixture was stirred at −78 degrees for another 30 min, and then warmed to room temperature slowly. After the reaction, the solvent was evaporated; dichloromethane was added to the residue. After filtering out the insoluble, filtrate was collected, and concentrated to give (4-ethoxy-3-methanesulfonyl-quinolin-6-yl)-methanol which was used in the next step reaction without further purification. LC-MS m/e 282 (MH+).

c) Preparation of 4-ethoxy-3-methanesulfonyl-quinoline-6-carbaldehyde

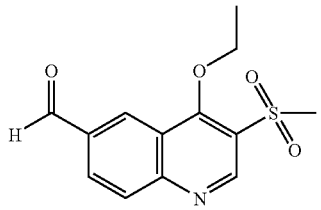

To a solution of (4-ethoxy-3-methanesulfonyl-quinolin-6-yl)-methanol (example 74b, 25.4 m mol) in anhydrous dichloromethane (500 mL), manganese oxide (13.3 g, 152.4 mmol) was added. The reaction mixture was stirred at 25 degrees for 6 hours. After the reaction, the solid was filtered out; the filtrate was concentrated in vacuo. Column chromatography gave 4-ethoxy-3-methanesulfonyl-quinoline-6-carbaldehyde (3.92 g, 55%). LC-MS m/e 280 (MH+).

d) Preparation of 5-(4-ethoxy-3-methanesulfonyl-quinolin-6-ylmethylene)-2-thioxo-thiazolidin-4-one

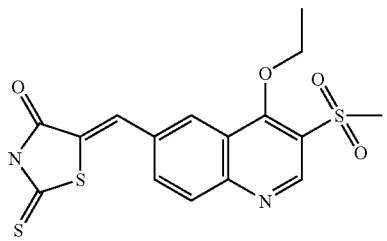

Similar procedure as described in example 61j was used, starting from 4-ethoxy-3-methanesulfonyl-quinoline-6-carbaldehyde (example 74c), sodium acetate, and acetic acid to give 5-(4-ethoxy-3-methanesulfonyl-quinolin-6-ylmethylene)-2-thioxo-thiazolidin-4-one. LC-MS m/e 395 (MH+).

e) Preparation of 5-(4-ethoxy-3-methanesulfonyl-quinolin-6-ylmethylene)-2-ethylsulfanyl-thiazol-4-one

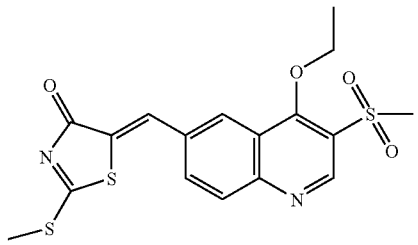

Similar procedure as described in example 41b was used, starting from 5-(4-ethoxy-3-methanesulfonyl-quinolin-6-ylmethylene)-2-thioxo-thiazolidin-4-one (example 74d), iodomethane, and DIEA (diisopropylethylamine) in acetonitrile to give 5-(4-ethoxy-3-methanesulfonyl-quinolin-6-ylmethylene)-2-ethylsulfanyl-thiazol-4-one. LC-MS m/e 409 (MH+).

f) Preparation of 2-cyclopropylamino-5-[1-(4-ethoxy-3-methanesulfonyl-quinolin-6-yl)-meth-(Z)-ylidene]-thiazol-4-one Similar procedure as described in example 41c was used, starting from 5-(4-ethoxy-3-methanesulfonyl-quinolin-6-ylmethylene)-2-ethylsulfanyl-thiazol-4-one (example 74e), cyclopropylamine, and DIEA (diisopropylethylamine) to give 2-cyclopropylamino-5-[1-(4-ethoxy-3-methanesulfonyl-quinolin-6-yl)-meth-(Z)-ylidene]-thiazol-4-one. LC-MS m/e 418 (MH+).

Example 75

2-Amino-5-[1-(4-ethoxy-3-methanesulfonyl-quinolin-6-yl)-meth-(Z)-ylidene]-thiazol-4-one

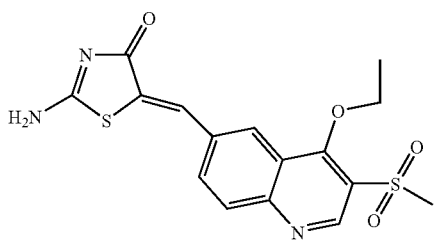

Similar procedure as described in example 41c was used, starting from 5-(4-ethoxy-3-methanesulfonyl-quinolin-6-ylmethylene)-2-ethylsulfanyl-thiazol-4-one (example 74e), ammonia in methanol, and DIEA (diisopropylethylamine) to give 2-amino-5-[1-(4-ethoxy-3-methanesulfonyl-quinolin-6-yl)-meth-(Z)-ylidene]-thiazol-4-one. LC-MS m/e 378 (MH+).

Example 76

6-[2-Amino-4-oxo-4H-thiazol-(5Z)-ylidenemethyl]-4-(tetrahydro-pyran-4-yloxy)-quinoline-3-carbonitrile

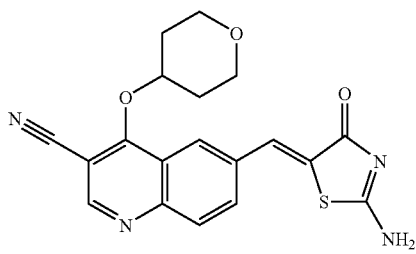

a) Preparation of 6-iodo-4-(tetrahydro-pyran-4-yloxy)-quinoline-3-carbonitrile

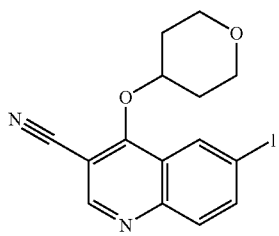

Similar procedure as described in example 28a was used, starting from 4-hydroxy tetrahydropyran, 4-chloro-6-iodo-quinoline-3-carbonitrile (example 14c) and potassium hydride in a solvent system of THF to give 6-iodo-4-(tetrahydro-pyran-4-yloxy)-quinoline-3-carbonitrile. LC-MS m/e 381 (MH$^+$).

b) Preparation of 6-formyl-4-(tetrahydro-pyran-4-yloxy)-quinoline-3-carbonitrile

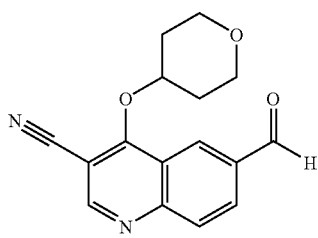

Similar procedure as described in example 28b was used, starting from 6-iodo-4-(tetrahydro-pyran-4-yloxy)-quinoline-3-carbonitrile (example 76a), carbon monoxide, triethylamine, diphenylpropylphosphine, palladium(II) acetate and trihexylsilane to give 6-formyl-4-(tetrahydro-pyran-4-yloxy)-quinoline-3-carbonitrile. LC-MS m/e 283 (MH$^+$).

c) Preparation of 6-[2-amino-4-oxo-4H-thiazol-(5Z)-ylidenemethyl]-4-(tetrahydro-pyran-4-yloxy)-quinoline-3-carbonitrile Similar procedure as described in example 28c was used, starting from 6-formyl-4-(tetrahydro-pyran-4-yloxy)-quinoline-3-carbonitrile (example 76b), pseudothiohydantoin, sodium acetate and acetic acid to give 6-[2-amino-4-oxo-4H-thiazol-(5Z)-ylidenemethyl]-4-(tetrahydro-pyran-4-yloxy)-quinoline-3-carbonitrile. LC-MS m/e 381 (MH$^+$).

Example 77

6-[2-Amino-4-oxo-4H-thiazol-(5Z)-ylidenemethyl]-4-(2-methoxy-ethoxy)-quinoline-3-carbonitrile

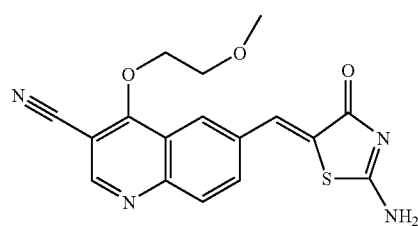

a) Preparation of 6-iodo-4-(2-methoxy-ethoxy)-quinoline-3-carbonitrile

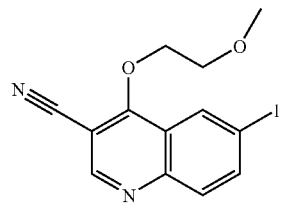

Similar procedure as described in example 28a was used, starting from 2-methoxy-ethanol, 4-chloro-6-iodo-quinoline-3-carbonitrile (example 14c) and potassium hydride in a solvent system of THF to give 6-iodo-4-(2-methoxy-ethoxy)-quinoline-3-carbonitrile. LC-MS m/e 355 (MH$^+$).

b) Preparation of 6-formyl-4-(2-methoxy-ethoxy)-quinoline-3-carbonitrile

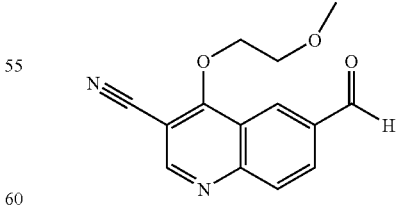

Similar procedure as described in example 28b was used, starting from 6-iodo-4-(2-methoxy-ethoxy)-quinoline-3-carbonitrile (example 77a), carbon monoxide, triethylamine, diphenylpropylphosphine, palladium(II) acetate and trihexylsilane to give 6-formyl-4-(2-methoxy-ethoxy)-quinoline-3-carbonitrile. LC-MS m/e 257 (MH$^+$).

c) Preparation of 6-[2-amino-4-oxo-4H-thiazol-(5Z)-ylidenemethyl]-4-(2-methoxy-ethoxy)-quinoline-3-carbonitrile Similar procedure as described in example 28c was used, starting from 6-formyl-4-(2-methoxy-ethoxy)-quinoline-3-carbonitrile (example 77b), pseudothiohydantoin, sodium acetate and acetic acid to give 6-[2-amino-4-oxo-4H-thiazol-(5Z)-ylidenemethyl]-4-(2-methoxy-ethoxy)-quinoline-3-carbonitrile. LC-MS m/e 355 (MH$^+$).

Example 78

6-[2-Cyclopropylamino-4-oxo-4H-thiazol-(5Z)-ylidenemethyl]-4-(tetrahydro-pyran-4-yloxy)-quinoline-3-carbonitrile

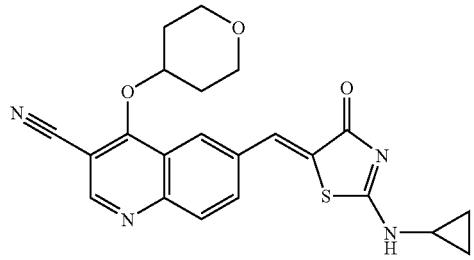

Similar procedure as described in example 28c was used, starting from 6-formyl-4-(tetrahydro-pyran-4-yloxy)-quinoline-3-carbonitrile (example 76b), 2-cyclopropylamino-thiazol-4-one (example 37c), sodium acetate and acetic acid to give 6-[2-cyclopropylamino-4-oxo-4H-thiazol-(5Z)-ylidenemethyl]-4-(tetrahydropyran-4-yloxy)quinoline-3-carbonitrile. LC-MS m/e 421 (MH$^+$).

Example 79

4-Butoxy-6-[2-cyclopropylamino-4-oxo-4H-thiazol-(5Z)-ylidenemethyl]-quinoline-3-carbonitrile

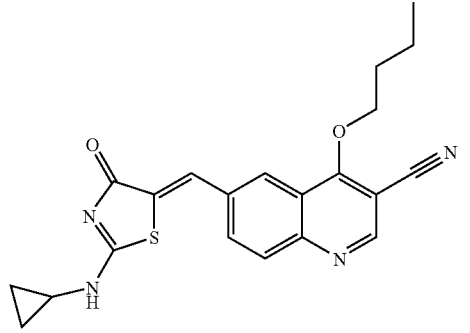

a) Preparation of 4-butoxy-6-iodo-quinoline-3-carbonitrile

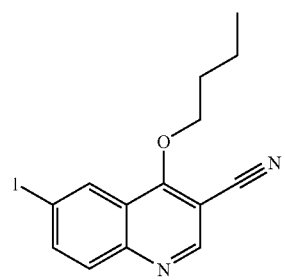

Similar procedure as described in example 28a was used, starting from butanol, 4-chloro-6-iodo-quinoline-3-carbonitrile (example 14c) and potassium hydride in a solvent system of THF to give 4-butoxy-6-iodo-quinoline-3-carbonitrile. LC-MS m/e 352 (MH$^+$).

b) Preparation of 4-butoxy-6-formyl-quinoline-3-carbonitrile

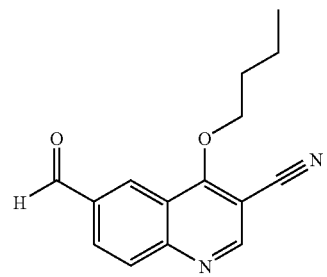

Similar procedure as described in example 28b was used, starting from 4-butoxy-6-iodo-quinoline-3-carbonitrile (example 79a), carbon monoxide, triethylamine, diphenylpropylphosphine, palladium(II) acetate and trihexylsilane to give 4-butoxy-6-formyl-quinoline-3-carbonitrile. LC-MS m/e 255 (MH$^+$).

c) Preparation of 4-butoxy-6-(4-oxo-2-thioxo-thiazolidin-5-ylidenemethyl)-quinoline-3-carbonitrile

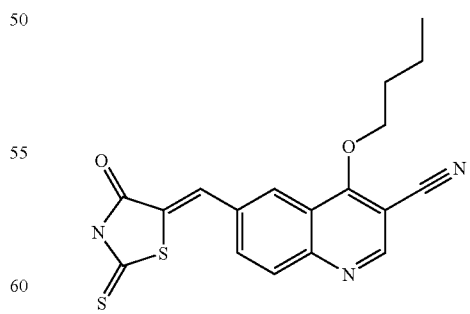

Similar procedure as described in example 41a was used, starting from 4-butoxy-6-formyl-quinoline-3-carbonitrile (example 79b), sodium acetate, and acetic acid to give 4-butoxy-6-(4-oxo-2-thioxo-thiazolidin-5-ylidenemethyl)-quinoline-3-carbonitrile. LC-MS m/e 370 (MH$^+$).

d) Preparation of 4-butoxy-6-(2-methylsulfanyl-4-oxo-4H-thiazol-5-ylidenemethyl)-quinoline-3-carbonitrile

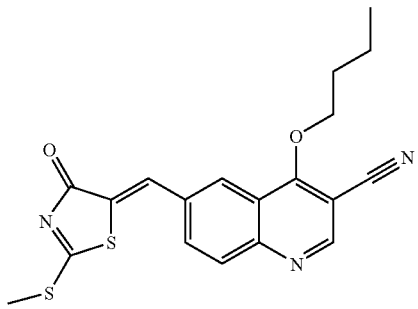

Similar procedure as described in example 41b was used, starting from 1-butoxy-7-(4-oxo-2-thioxo-thiazolidin-5-ylidenemethyl)-naphthalene-2-carbonitrile (example 79c), iodomethane, and DIEA (diisopropylethylamine) in acetonitrile to give 4-butoxy-6-(2-methylsulfanyl-4-oxo-4H-thiazol-5-ylidenemethyl)-quinoline-3-carbonitrile. LC-MS m/e 384 (MH+).

e) Preparation of 4-butoxy-6-[2-cyclopropylamino-4-oxo-4H-thiazol-(5Z)-ylidenemethyl]-quinoline-3-carbonitrile Similar procedure as described in example 41c was used, starting from 1-butoxy-7-(2-methylsulfanyl-4-oxo-4H-thiazol-5-ylidenemethyl)-naphthalene-2-carbonitrile (example 79d), cyclopropylamine, and DIEA (diisopropylethylamine) to give 4-butoxy-6-[2-cyclopropylamino-4-oxo-4H-thiazol-(5Z)-ylidenemethyl]-quinoline-3-carbonitrile. LC-MS m/e 393 (MH+).

Example 80

6-[2-Amino-4-oxo-4H-thiazol-(5Z)-ylidenemethyl]-4-butoxy-quinoline-3-carbonitrile

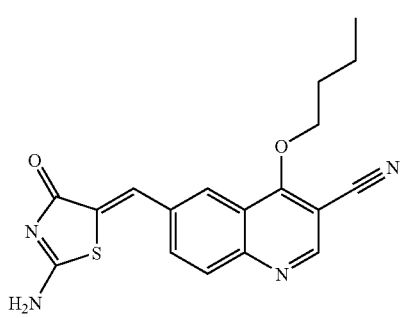

Similar procedure as described in example 28c was used, starting from 4-butoxy-6-formyl-quinoline-3-carbonitrile (example 79b), pseudothiohydantoin, sodium acetate and acetic acid to give 6-[2-amino-4-oxo-4H-thiazol-(5Z)-ylidenemethyl]-4-butoxy-quinoline-3-carbonitrile. LC-MS m/e 381 (MH+).

Example 81

6-[2-Cyclopropylamino-4-oxo-4H-thiazol-(5Z)-ylidenemethyl]-4-(2-methoxy-ethoxy)-quinoline-3-carbonitrile

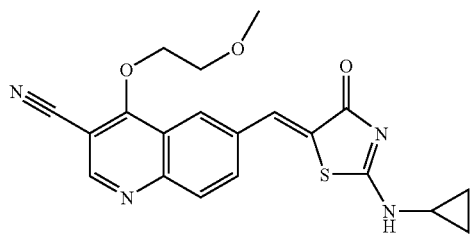

Similar procedure as described in example 28c was used, starting from 6-formyl-4-(2-methoxy-ethoxy)-quinoline-3-carbonitrile (example 77b), 2-cyclopropylamino-thiazol-4-one (example 37c), sodium acetate and acetic acid to give 6-[2-cyclopropylamino-4-oxo-4H-thiazol-(5Z)-ylidenemethyl]-4-(2-methoxy-ethoxy)-quinoline-3-carbonitrile. LC-MS m/e 395 (MH+).

Example 82

The pharmacological properties of the compounds of this invention may be confirmed by a number of pharmacological assays. The exemplified pharmacological assays which follow have been carried out with the compounds according to the invention and their salts. The compounds of the invention exhibited CDK1/Cyclin B activity with Ki values of less than 5.0 µM. This demonstrates that all of these compounds were active to inhibit CDK1/Cyclin B.

Kinase Assays

To determine inhibition of CDK1 activity, either Flash-Plate™ (NEN™-Life Science Products) assay or HTRF assay was performed. Both types of kinase assays were carried out using recombinant human CDK1/Cyclin B complex. GST-cyclinB (GST-cycB) and CDK1cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. Cell 1993, 75, 805-816). A 6×-Histidine tagged truncated form of retinoblastoma (Rb) protein (amino acid 386-928) was used as the substrate for the CDK1/Cyclin B assay (the expression plasmid was provided by Dr. Veronica Sullivan, Department of Molecular Virology, Roche Research Centre, Welwyn Garden City, United Kingdom). The Rb protein is a natural substrate for phosphorylation by CDK1 (see Herwig and Strauss Eur. J. Biochem. Vol. 246 (1997) pp. 581-601 and the references cited therein). The expression of the 62 Kd protein was under the control of an IPTG inducible promoter in an M15 E. coli strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialyzed against 20 mM HEPES pH 7.5, 30% glycerol, 200 mM NaCl, and 1 mM DTT. Purified Rb fusion protein stocks were quantitated for protein concentration, aliquoted, and stored at −70° C.

For the FlashPlate kinase assay, 96-well FlashPlates were coated with Rb protein at 10 μg/ml, using 100 μl per well. Plates were incubated at 4° C. overnight or at room temperature for 3 hours on a shaker. To control for nonspecific phosphorylation, one row of wells was coated with 100 μl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 μl reaction mix (25 mM HEPES, 20 mM MgCl$_2$, 0.002% Tween 20, 2 mM DTT, 1 μM ATP, 4 nM 33P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times 1 - \frac{\text{test compound} - \text{nonspecific}}{\text{total} - \text{nonspecific}}$$

where "test compound" refers to the average counts per minute of the test duplicates, "nonspecific" refers to the average counts per minute when no CDK1/Cyclin B, etc., was added, and "total" refers to the average counts per minute when no compound was added. The IC$_{50}$ value is the concentration of test compound that reduces by 50% the protein-kinase induced incorporation of the radiolabel under the test conditions described. The value of the inhibitor constant Ki is calculated by the following: Ki=IC50/(1+[S]/Km), where [S] is the ATP concentration and Km is Michaelis constant.

The Homofeneous Time Resolved Fluorescence (HTRF) kinase assay was carried out in 96-well polypropylene plates (BD Biosciences, Bedford, Mass.). Test compounds were first dissolved in DMSO, and then diluted in kinase assay buffer 1 (25 mM HEPES, pH7.0, 8 mM MgCl$_2$, 1.5 mM DTT, and 162 μM ATP) with DMSO concentration at 15%. The CDK1/Cyclin B enzyme was diluted in kinase assay buffer 2 (25 mM HEPES, pH 7.0, 8 mM MgCl$_2$, 0.003% Tween 20, 0.045% BSA, 1.5 mM DTT, and 0.675 μM Rb protein). To initiate the kinase reaction, 20 μL of compound solution was mixed with 40 μL of CDK1/Cyclin B solution in assay plates with final concentration of CDK1/Cyclin B and Rb at 0.1 μg/mL and 0.225 μM, respectively, and incubated at 37° C. for 30 min. 15 μL of anti-phospho-Rb (Ser 780) antibody (Cell Signaling Technology, Beverly, Mass.,) was added with a 1:7692 dilution of the antibody. Incubation was continued at 37° C. for 25 min, after which LANCE Eu-W1024 labeled anti-rabbit IgG (1 nM, PerkinElmer, Wellesley, Mass.) and anti-His antibody conjugated to SureLight-Allophucocyanin (20 nM, PerkinElmer, Wellesley, Mass.) were added to the wells. Incubation was continued at 37° C. for another 40 min. At the completion of the incubation, 35 μL of reaction mixture was transferred to fresh 384-well black polystyrene plates (Corning Incorporated, Corning, N.Y.) and read on a fluorescent plate reader at excitation wavelength of 340 nm and emission wavelength of 665/615 nm.

Ki values showing Cdk1/cyclin B activity that applied to compounds of the subject matter of this invention ranges from about 0.001 μM to about 5.000 μM. Specific data for some example are as follows:

| Example | Ki (μM) |
|---------|---------|
| 5  | 0.179 |
| 10 | 0.958 |
| 15 | 0.008 |
| 20 | 0.228 |
| 25 | 1.004 |
| 30 | 0.184 |
| 40 | 0.016 |
| 50 | 0.065 |
| 60 | 0.028 |
| 70 | 0.006 |
| 80 | 0.001 |

What is claimed:

1. A compound of the formula:

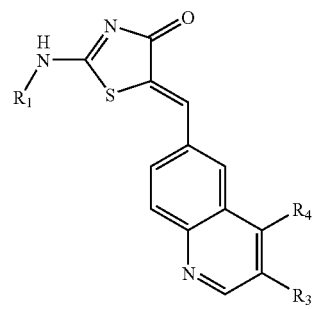

wherein

R$_1$ is hydrogen, lower alkyl, cyclo lower alkyl, aryloxy-lower alkyl, lower alkoxy, hydroxyl lower alkyl, —NH$_2$, —[CH$_2$CH$_2$O]$_x$R$_8$ or R$_2$—(X)$_n$—X is selected from lower alkylene, cyclo lower alkylene, aryl lower alkylene, carboxy lower alkylene, hydroxy lower alkylene, amido lower alkylene, mono- or di-halo lower alkylene, amino lower alkylene, mono- or di-lower alkyl amino lower alkylene and imido lower alkylene, R$_2$ is

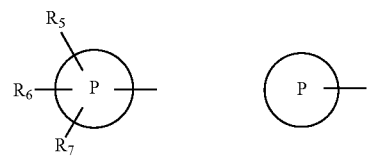

is selected from an aryl ring, cycloalkyl ring containing from 3 to 6 carbon atoms, a 4 to 6 membered heterocycloalkyl ring containing from 3 to 5 carbon atoms and from 1 to 2 hetero atoms selected from the group consisting of oxygen, nitrogen and sulfur, and a 5 or 6 membered heteroaromatic ring containing from 1 to 2 hetero atoms selected from the group consisting of oxygen, sulfur and nitrogen;

R$_5$, R$_6$ and R$_7$ are independently selected from the group consisting of hydroxy, lower alkyl sulfone, hydroxy-lower alkyl, hydrogen, lower alkyl, halogen, perfluro lower alkyl, lower alkoxy, amino, mono- or di-lower alkyl amino, or when two of the substituents $R_5$, $R_6$ and $R_7$ are substituted on adjacent carbon atoms on ring (P), these two substituents can be taken together with their adjacent, attached carbon atoms to form an aryl ring, a 3 to 6 membered cyclic lower alkyl ring, a 4 to 6 membered heterocycloalkyl ring or a 4 to 6 membered heteroaromatic ring, said heterocycloalkyl ring and said heteroaromatic ring containing from 1 to 2 hetero atoms selected from the group consisting of oxygen, nitrogen or sulfur;

(R)— is selected from an aryl ring, a cycloalkyl ring containing from 3 to 6 carbon atoms, a 4 to 6 membered heterocyclic alkyl ring containing from 1 to 2 hetero atoms selected from the group consisting of a oxygen, sulfur and nitrogen or a 5 to 6 numbered heteroaromatic right containing from 1 to 2 hetro atoms selected from the group consisting of oxygen, sulfur and nitrogen;

$R_3$ is cyano, $$\underset{O}{\overset{H}{\|}}{-}\!\!\!-\!\!\!N\!-\!\!\![\;]_x\!N\!\!\underset{R16}{\overset{R15}{<}},$$

$-(CH_2)_x-\underset{O}{\overset{\|}{C}}-OR_{11}$, (R with $R_{17}$, $R_{18}$) and $-\underset{O}{\overset{O}{\underset{\|}{\overset{\|}{S}}}}-R_{10}$;

$R_4$ is $-O(CH_2CH_2O)_y-R_{10}$, lower alkyl, (R with $R_{17}$, $R_{18}$)$-(R_{12})_k-$ and $-R_{12}-R_{14}$;

$R_8$, $R_{11}$, $R_{15}$, $R_{16}$, $R_{17}$, and $R_{18}$ are independently hydrogen or lower alkyl;
$R_{10}$ is lower alkyl;
$R_{12}$ is O or S;
$R_{14}$ is selected from hydroxyalkyl, lower alkyl, cycloalkyl, haloalkyl, perfluoroalkyl and protected hydroxyalkyl;
x, n and k are integers from 0 to 1;
z is an integer from 0 to 3;
y is an integer from 1 to 3; and
v is an integer from 1 to 6, or
pharmaceutically acceptable salts thereof.

2. The compound of claim 1 wherein said compound is:

I-A wherein $R_1'$ is hydrogen, lower alkyl, cyclo lower alkyl, lower alkoxy, aryloxy lower alkyl, $-NH_2$, hydroxy lower alkyl,
or $-[CH_2CH_2O]_v R_8$ and
$R_8$, v, $R_3$ and $R_4$ are as above.

3. The compound of claim 2 wherein $R_1'$ is lower alkoxy, aryloxy lower alkyl, $NH_2$ or hydroxyl lower alkyl.

4. The compound of claim 2 wherein $R_1'$ is $-[CH_2CH_2O]_v R_8$
and $R_8$ and v are as above.

5. The compound of claim 4 wherein $R_3$ is cyano and $R_4$ is $-O(CH_2CH_2O)_y-R_{10}$ and y and $R_{10}$ is as above.

6. The compound of claim 2 wherein $R_1'$ is hydrogen, cycloalkyl or lower alkyl.

7. The compound of claim 6 wherein $R_3$ is cyano.

8. The compound of claim 7 wherein $R_4$ is $-O(CH_2CH_2O)_y-R_{10}$, and y and $R_{10}$ are as above.

9. The compound of claim 7 where said $R_4$ is (R with $R_{17}$, $R_{18}$)$-(O)_k-$ with the ring $-$(R)

k = 1 and being a heterocycloalkyl ring.

10. The compound of claim 9 wherein the ring contains a nitrogen or oxygen atom as the only hetero atom.

11. The compound of claim 3 wherein $R_1'$ is lower alkyl.

12. The compound of claim 1 having the formula:

I-B wherein
$R_1''$ is $R_2'-(X)_n-$;

n, $R_3$ and $R_4$ are as above, and

X is selected from lower alkylene, cyclo lower alkylene, aryl lower alkylene, carboxy lower alkylene, hydroxy lower alkylene, amido lower alkylene, mono- or di-halo lower alkylene, amino lower alkylene, mono- or di-lower alkyl amino lower alkylene or imido lower alkylene;

$R_2'$ is

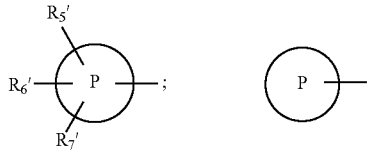

is selected from an aryl ring, cycloalkyl ring containing from 3 to 6 carbon atoms, a 4 to 6 membered heterocycloalkyl ring containing from 3 to 5 carbon atoms and from 1 to 2 hetero atoms selected from the group consisting of oxygen, nitrogen and sulfur, a 5 or 6 membered heteroaromatic ring containing from 1 to 2 hetero atoms selected from the group consisting of oxygen, sulfur and nitrogen;

$R_5'$, $R_6'$ and $R_7'$ are independently selected from the group consisting of hydroxy, lower alkyl sulfone, hydroxyl lower alkyl, hydrogen, lower alkyl, halogen, perfluro lower alkyl, lower alkoxy, amino, mono- or di-lower alkyl amino, or pharmaceutically acceptable salts thereof.

13. The compound of claim 12 wherein aryl is phenyl.

14. The compound of claim 13 wherein n is 0.

15. The compound of claim 14 wherein $R_2'$ is a cyclo lower alkyl ring.

16. The compound of claim 15 wherein said cycloalkyl ring is cyclopropyl.

17. The compound of claim 16 wherein $R_3$ is cyano and $R_4$ is —O(CH$_2$CH$_2$O)$_y$—R$_{10}$ or

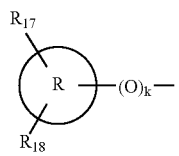

k = 1 or ——$R_{12}$–$R_{14}$ and $R_{10}$, $R_{12}$, $R_{14}$, $R_{17}$, $R_{18}$, y and k are as above.

18. The compound is claim 17 wherein $R_4$ is

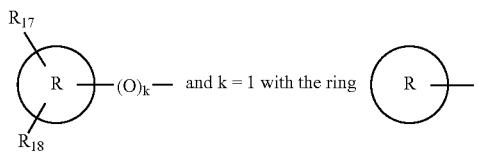

being a heterocycloalkyl ring containing a nitrogen or oxygen atom as the only hetero atom.

19. The compound of claim 13 wherein n is 1.

20. The compound of claim 19 wherein X is selected from lower alkylene, hydroxy lower alkylene, cyclolower alkylene, and mono- or di-halo lower alkylene.

21. The compound of claim 20 where X is cyclopropylene.

22. The compound of claim 21 wherein $R_2'$ is phenyl.

23. The compound of claim 22 wherein $R_3$ is cyano or

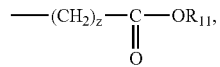

and z=0 and $R_{11}$ is as above.

24. The compound of claim 23 wherein $R_4$ is —O(CH$_2$CH$_2$O)$_y$—R$_{10}$, lower alkyl and cyclo lower alkyl or —$R_{12}$—$R_{14}$ and y, $R_{10}$, $R_{12}$ and $R_{14}$ are as above.

25. The compound of claim 1 wherein said compound is selected from the group consisting of 4-methoxy-6-[4-oxo-2-((1R,2S)-2-phenyl-cyclopropylamino)-4H-thiazol-(5Z)-ylidenemethyl]-quinoline-3-carboxylic acid methyl ester;

4-methoxy-6-[4-oxo-2-((1R,2S)-2-phenyl-cyclopropylamino)-4H-thiazol-(5Z)-ylidenemethyl]-quinoline-3-carboxylic acid;

4-ethoxy-6-[4-oxo-2-((1R,2S)-2-phenyl-cyclopropylamino)-4H-thiazol-(5Z)-ylidenemethyl]-quinoline-3-carboxylic acid ethyl ester;

4-methoxy-6-[4-oxo-2-((1R,2S)-2-phenyl-cyclopropylamino)-4H-thiazol-(5Z)-ylidenemethyl]-quinoline-3-carboxylic acid methyl ester and 4-ethoxy-6-[4-oxo-2-((1R,2S)-2-phenyl-cyclopropylamino)-4H-thiazol-(5Z)-ylidenemethyl]-quinoline-3-carbonitrile.

26. The compound of claim 22 wherein $R_4$ is —O(CH$_2$CH$_2$O)$_y$—R$_{10}$ or —$R_{12}$—$R_{14}$ and $R_3$ is

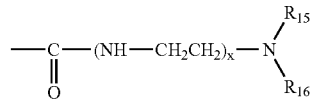

where x, y, $R_{10}$, $R_{12}$, $R_{14}$, $R_{15}$ and $R_{16}$ are as above.

27. The compound of claim 1 wherein said compound is 4-ethoxy-6-[2-[2-(2-methoxy-ethoxy)-ethylamino]-4-oxo-4H-thiazol-(5Z)-ylidenemethyl]-4-ethoxy-quinoline-3-carbonitrile;

6-[2-amino-4-oxo-4H-thiazol-(5Z)-ylidenemethyl]-4-[2-(2-methoxy-ethoxy)-ethoxy]-quinoline-3-carbonitrile;

4-ethoxy-6-[4-oxo-2-[(4-trifluoromethyl-pyridin-2-ylmethyl)-amino]-4H-thiazol-(5Z)-ylidenemethyl]-quinoline-3-carbonitrile;

4-{6-[2-amino-4-oxo-4H-thiazol-(5Z)-ylidenemethyl]-3-cyano-quinolin-4-yloxy}-piperidine-1-carboxylic acid tert-butyl ester;

6-[2-amino-4-oxo-4H-thiazol-(5Z)-ylidenemethyl]-4-(piperidin-4-yloxy)-quinoline-3-carbonitrile;

4-{3-cyano-6-[2-cyclopropylamino-4-oxo-4H-thiazol-(5Z)-ylidenemethyl]-quinolin-4-yloxy}-piperidine-1-carboxylic acid tert-butyl ester;

6-(2-cyclopropylamino-4-oxo-4H-thiazol-5-ylidenemethyl)-4-(piperidin-4-yloxy)-quinoline-3-carbonitrile;

4-methoxy-6-[4-oxo-2-((1R,2S)-2-phenyl-cyclopropylamino)-4H-thiazol-(5Z)-ylidenemethyl]-quinoline-3-carboxylic acid amide;

4-methoxy-6-[4-oxo-2-((1R,2S)-2-phenyl-cyclopropylamino)-4H-thiazol-(5Z)-ylidenemethyl]-quinoline-3-carboxylic acid dimethylamide and 4-methoxy-6-[4-oxo-2-((1R,2S)-2-phenyl-cyclopropylamino)-4H-thiazol-(5Z)-ylidenemethyl]-quinoline-3-carboxylic acid (2-dimethylamino-ethyl)-amide.

28. The compound of claim 20 wherein X is hydroxy lower alkylene.

29. The compound of claim 28 wherein $R_3$ is cyano, $$-(CH_2)_z-\underset{\underset{O}{\|}}{C}-OR_{11} \text{ or } -\underset{\underset{O}{\|}}{C}-(NH-CH_2CH_2)_x-N\overset{R_{15}}{\underset{R_{16}}{\diagdown}}$$

and $R_4$ is $-O(CH_2CH_2O)_y-R_{10}$ or $-R_{12}-R_{14}$ and where x, y, $R_{10}$, $R_{12}$, $R_{14}$, $R_{11}$, $R_{15}$ and $R_{16}$ are as above.

30. The compound of claim 29 wherein $R_2'$ is phenyl, perfluro lower alkyl substituted phenyl or halo substituted phenyl.

31. The compound of claim 1 wherein said compound is selected from the group consisting of
   6-[2-((R)-2-hydroxy-1-phenyl-ethylamino)-4-oxo-4H-thiazol-(5Z)-ylidenemethyl]-4-methoxy-quinoline-3-carboxylic acid methyl ester;
   6-[2-((R)-2-hydroxy-1-phenyl-ethylamino)-4-oxo-4H-thiazol-(5Z)-ylidenemethyl]-4-methoxy-quinoline-3-carboxylic acid;
   4-ethoxy-6-[2-((R)-2-hydroxy-1-phenyl-ethylamino)-4-oxo-4H-thiazol-(5Z)-ylidenemethyl]-quinoline-3-carbonitrile;
   4-ethoxy-6-[2-(2-hydroxy-2-phenyl-ethylamino)-4-oxo-4H-thiazol-(5Z)-ylidenemethyl]-quinoline-3-carbonitrile;
   6-[2-((R)-1-hydroxymethyl-2-phenyl-ethylamino)-4-oxo-4H-thiazol-(5Z)-ylidenemethyl]-4-methoxy-quinoline-3-carboxylic acid amide;
   6-[2-cyclopropylamino-4-oxo-4H-thiazol-(5Z)-ylidenemethyl]-4-[2-(2-methoxy-ethoxy)-ethoxy]-quinoline-3-carbonitrile;
   6-[2-tert-butylamino-4-oxo-4H-thiazol-(5Z)-ylidenemethyl]-4-ethoxy-quinoline-3-carbonitrile and
   6-[2-((R)-2-hydroxy-1-phenyl-ethylamino)-4-oxo-4H-thiazol-(5Z)-ylidenemethyl]-4-methoxy-quinoline-3-carboxylic acid amide.

32. The compound of claim 20 wherein X is lower alkylene.

33. The compound of claim 32 wherein $R_2'$ is phenyl, halophenyl, perfluro lower alkyl phenyl.

34. The compound of claim 33 wherein $R_3$ is cyano, $$-(CH_2)_z-\underset{\underset{O}{\|}}{C}-OR_{11} \text{ or } -\underset{\underset{O}{\|}}{C}-(NH-CH_2CH_2)_x-N\overset{R_{15}}{\underset{R_{16}}{\diagdown}}$$

and $R_4$ is $-O(CH_2CH_2O)_y-R_{10}$ or $-R_{12}-R_{14}$
   wherein x, y, z $R_{10}$, $R_{11}$, $R_{12}$, $R_{14}$, $R_{15}$ and $R_{16}$ are as above.

35. The compound of claim 33 where $R_3$ is

[structure with $R_{18}$, R, $R_{17}$ on a ring]

wherein $R_{17}$, $R_{18}$ and k as above,
   and 4 is $-O(CH_2CH_2O)_y-R_{10}$ or $-R_{12}-R_{14}$
   wherein y, $R_{10}R_{12}$ and $R_{14}$ are as above.

36. The compound of claim 35 wherein

[ring with R]

is heteroamatic ring containing nitrogen and oxygen as the heteroatoms.

37. The compound of claim 32 where $R_2'$ is

[ring with $R_5'$, $R_6'$, P, $R_7'$]

and the Ⓟ is a heteroaromatic ring containing one or two nitrogen atoms as the only hetero atom and $R_5'$, $R_6'$ and $R_7'$ are as above.

38. The compound of claim 37 wherein $R_3$ is cyano, $$-(CH_2)_z-\underset{\underset{O}{\|}}{C}-OR_{11} \text{ or } -\underset{\underset{O}{\|}}{C}-(NH-CH_2CH_2)_x-N\overset{R_{15}}{\underset{R_{16}}{\diagdown}}$$

and $R_4$ is $-O(CH_2CH_2O)_y-R_{10}$, lower alkyl and cyclo lower alkyl or $-R_{12}-R_{14}$
   wherein x, y, z, $R_{10}$, $R_{12}$, $R_{14}$, $R_{15}$ and $R_{16}$ are as above.

39. The compound of claim 38 wherein said heteroaromatic ring contains one or two nitrogen atoms as the only heteroatoms.

40. The compound of claim 38 wherein said heteroaromatic ring contains a sulfur and nitrogen atom as the heteroatoms.

41. The compound of claim 32 where $R_2'$ is

[ring with $R_5$, $R_6$, P, $R_7$]

and the ring Ⓟ is a heterocycloalkyl ring.

42. The compound of claim 41 wherein $R_3$ is cyano,

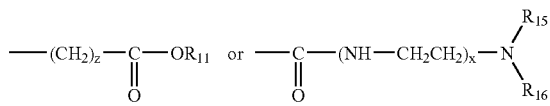

and $R_4$ is $—O(CH_2CH_2O)_y—R_{10}$, lower alkyl and cyclo lower alkyl or $—R_{12}—R_{14}$
wherein x, y, z, $R_{10}$, $R_{11}$, $R_{12}$, $R_{14}$, $R_{15}$ and $R_{16}$ are as above.

43. The compound of claim 20 where X is mono or dihalolower alkylene.

44. The compound of claim 43 wherein the ring ⓟ which constitutes $R_2'$ is a heteroaromatic ring containing one or two nitrogen atoms as the only hetero atom.

45. The compound of claim 44 wherein $R_3$ is cyano,

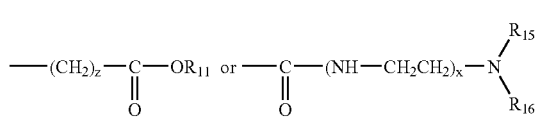

and $R_4$ is $—O(CH_2CH_2O)_y—R_{10}$, lower alkyl and cyclo lower alkyl or $—R_{12}—R_{14}$
wherein x, y, z, $R_{10}$, $R_{11}$, $R_{12}$, $R_{14}$, $R_{15}$ and $R_{16}$ are as above.

46. The compound of claim 7 wherein $R_4$ is $—R_{12}-R_{14}$, $R_{12}$ is O and $R_{14}$ are as above.

47. The compound of claim 46 wherein $R_{14}$ is alkyl.

48. The compound of claim 47 wherein said compound is
6-[2-amino-4-oxo-4H-thiazol-(5Z)-ylidenemethyl]-4-ethoxy]-quinoline-3-carbonitrile;
6-[2-amino-4-oxo-4H-thiazol-(5Z)-ylidenemethyl]-4-isopropoxy-quinoline-3-carbonitrile;
6-[2-amino-4-oxo-4H-thiazol-(5Z)-ylidenemethyl]-4-(1-ethyl-propoxy)-quinoline-3-carbonitrile;
6-[2-amino-4-oxo-4H-thiazol-(5Z)-ylidenemethyl]-4-isobutoxy-quinoline-3-carbonitrile;
6-[2-amino-4-oxo-4H-thiazol-(5Z)-ylidenemethyl]-4-(2,2-dimethyl-propoxy)-quinoline-3-carbonitrile;
6-[2-amino-4-oxo-4H-thiazol-(5Z)-ylidenemethyl]-4-butoxy-quinoline-3-carbonitrile;
6-[2-cyclopropylamino-4-oxo-4H-thiazol-(5Z)-ylidenemethyl]-4-ethoxy-quinoline-3-carbonitrile;
6-[2-cyclopropylamino-4-oxo-4H-thiazol-(5Z)-ylidenemethyl]-4-isopropoxy-quinoline-3-carbonitrile;
6-[2-cyclopropylamino-4-oxo-4H-thiazol-(5Z)-ylidenemethyl]-4-(1-ethyl-propoxy)-quinoline-3-carbonitrile;
6-[2-cyclopropylamino-4-oxo-4H-thiazol-(5Z)-ylidenemethyl]-4-isobutoxy-quinoline-3-carbonitrile;
6-[2-cyclopropylamino-4-oxo-4H-thiazol-(5Z)-ylidenemethyl]-4-(2,2-dimethyl-propoxy)-quinoline-3-carbonitrile, and
6-[2-cyclopropylamino-4-oxo-4H-thiazol-(5Z)-ylidenemethyl]-4-(tetrahydro-pyran-4-yloxy)-quinoline-3-carbonitrile.

49. The compound of claim 7 wherein $R_4$ is $—R_{12}—R_{14}$, $R_{12}$ is S and $R_{14}$ are as above.

50. The compound of claim 49 wherein $R_{14}$ is alkyl.

51. The compound of claim 50 wherein said compound is
6-[2-amino-4-oxo-4H-thiazol-(5Z)-ylidenemethyl]-4-tert-butylsulfanyl-quinoline-3-carbonitrile;
6-[2-amino-4-oxo-4H-thiazol-(5Z)-ylidenemethyl]-4-isopropylsulfanyl-quinoline-3-carbonitrile;
6-[2-amino-4-oxo-4H-thiazol-(5Z)-ylidenemethyl]-4-isopropylsulfanyl-quinoline-3-carbonitrile; compound with methanesulfonic acid;
6-[2-amino-4-oxo-4H-thiazol-(5Z)-ylidenemethyl]-4-butylsulfanyl-quinoline-3-carbonitrile;
6-[2-amino-4-oxo-4H-thiazol-(5Z)-ylidenemethyl]-4-ethylsulfanyl-quinoline-3-carbonitrile;
6-[2-amino-4-oxo-4H-thiazol-(5Z)-ylidenemethyl]-4-methylsulfanyl-quinoline-3-carbonitrile and
6-[2-amino-4-oxo-4H-thiazol-(5Z)-ylidenemethyl]-4-isobutylsulfanyl-quinoline-3-carbonitrile.

52. The compound of claim 7 wherein $R_4$ is alkyl.

53. The compound of claim 52 wherein said compound is
6-[2-amino-4-oxo-4H-thiazol-(5Z)-ylidenemethyl]-4-isobutyl-quinoline-3-carbonitrile;
6-[2-amino-4-oxo-4H-thiazol-(5Z)-ylidenemethyl]-4-butyl-quinoline-3-carbonitrile;
6-[2-amino-4-oxo-4H-thiazol-(5Z)-ylidenemethyl]-4-hexyl-quinoline-3-carbonitrile;
6-[2-amino-4-oxo-4H-thiazol-(5Z)-ylidenemethyl]-4-propyl-quinoline-3-carbonitrile;
6-[2-amino-4-oxo-4H-thiazol-(5Z)-ylidenemethyl]-4-pentyl-quinoline-3-carbonitrile and
6-[2-amino-4-oxo-4H-thiazol-(5Z)-ylidenemethyl]-4-methyl-quinoline-3-carbonitrile.

54. The compound of claim 7 wherein $R_4$ is

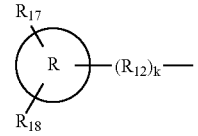

R, $R_{12}$, $R_{17}$, $R_{18}$ and k are as above.

55. The compound of claim 54 wherein k=0.

56. The compound of claim 55 wherein R is cyclopropyl.

57. The compound of claim 56 wherein said compound is
6-[2-amino-4-oxo-4H-thiazol-(5Z)-ylidenemethyl]-4-cyclopropyl-quinoline-3-carbonitrile.

58. The compound of claim 1 wherein said compound is
6-[2-(2,2-difluoro-2-pyridin-2-yl-ethylamino)-4-oxo-4H-thiazol-(5Z)-ylidenemethyl]-4-ethoxy-quinoline-3-carbonitrile;
4-ethoxy-6-[4-oxo-2-[(tetrahydro-pyran-4-ylmethyl)-amino]-4H-thiazol-(5Z)-ylidenemethyl]-quinoline-3-carbonitrile;
4-ethoxy-6-[2-(2-imidazol-1-yl-ethylamino)-4-oxo-4H-thiazol-(5Z)-ylidenemethyl]-quinoline-3-carbonitrile;
4-ethoxy-6-[4-oxo-2-[(pyridin-2-ylmethyl)-amino]-4H-thiazol-(5Z)-ylidenemethyl]-quinoline-3-carbonitrile;
4-ethoxy-6-[4-oxo-2-[(pyrimidin-2-ylmethyl)-amino]-4H-thiazol-(5Z)-ylidenemethyl]-quinoline-3-carbonitrile;
4-ethoxy-6-[4-oxo-2-[(pyrazin-2-ylmethyl)-amino]-4H-thiazol-(5Z)-ylidenemethyl]-quinoline-3-carbonitrile;
2-[2-(3-fluoro-phenyl)-ethylamino]-5-[1-[4-methoxy-3-(5-methyl-oxazol-2-yl)-quinolin-6-yl]-meth-(Z)-ylidene]-thiazol-4-one;
4-ethoxy-6-[2-[2-(3-fluoro-phenyl)-ethylamino]-4-oxo-4H-thiazol-(5Z)-ylidenemethyl]-quinoline-3-carbonitrile and
4-ethoxy-6-[4-oxo-2-[(thiazol-2-ylmethyl)-amino]-4H-thiazol-(5Z)-ylidenemethyl]-quinoline-3-carbonitrile.

59. The compound of claim 1 selected from the group consisting of

- 4-ethoxy-6-[2-((S)-2-hydroxy-2-phenyl-ethylamino)-4-oxo-4H-thiazol-(5Z)-ylidenemethyl]-quinoline-3-carbonitrile;
- 4-ethoxy-6-[2-(R)-2-hydroxy-2-phenyl-ethylamino)-4-oxo-4H-thiazol-(5Z)-ylidenemethyl]-quinoline-3-carbonitrile;
- 6-[2-(R)-1-hydroxymethyl-2-methyl-propylamino)-4-oxo-4H-thiazol-(5Z)-ylidenemethyl]-4-isopropoxy-quinoline-3-carbonitrile;
- 6-[2-(R)-2-hydroxy-1-phenyl-ethylamino)-4-oxo-4H-thiazol-(5Z)-ylidenemethyl]-4-isopropoxy-quinoline-3-carbonitrile;
- 6-[2-amino-4-oxo-4H-thiazol-(5Z)-ylidenemethyl]-4-(2,2,2-trifluoro-ethoxy)-quinoline-3-carbonitrile;
- 6-[2-(2,3-dihydroxy-propylamino)-4-oxo-4H-thiazol-(5Z)-ylidenemethyl]-4-isopropylsulfanyl-quinoline-3-carbonitrile.
- 6-[2-amino-4-oxo-4H-thiazol-(5Z)-ylidenemethyl]-4-(2,2,2-trifluoro-1-trifluoromethyl-ethoxy)-quinoline-3-carbonitrile;
- 6-[2-amino-4-oxo-4H-thiazol-(5Z)-ylidenemethyl]-4-(3-hydroxy-propylsulfanyl)-quinoline-3-carbonitrile and
- 6-[2-amino-4-oxo-4H-thiazol-(5Z)-ylidenemethyl]-4-[3-(tert-butyl-dimethyl-silanyloxy)-propylsulfanyl]-quinoline-3-carbonitrile.

60. The compound of claim 1 selected from the group consisting of

- 4-isopropoxy-6-[4-oxo-2-[(thiophen-2-ylmethyl)-amino]-4H-thiazol-(5Z)-ylidenemethyl]-quinoline-3-carbonitrile;
- 6-[2-(2-hydroxy-1-hydroxymethyl-ethylamino)-4-oxo-4H-thiazol-(5Z)-ylidenemethyl]-4-isopropoxy-quinoline-3-carbonitrile;
- 6-[2-hydrazino-4-oxo-4H-thiazol-(5Z)-ylidenemethyl]-4-isopropoxy-quinoline-3-carbonitrile;
- 2-amino-5-[1-(3-methanesulfonyl-4-phenyl-quinolin-6-yl)-meth-(Z)-ylidene]-thiazol-4-one;
- 6-[2-amino-4-oxo-4H-thiazol-(5Z)-ylidenemethyl]-4-phenyl-quinoline-3-carbonitrile;
- 6-[2-amino-4-oxo-4H-thiazol-(5Z)-ylidenemethyl]-4-pyridin-3-yl-quinoline-3-carbonitrile; compound with trifluoro-acetic acid;
- 2-ayclopropylamino-5-[1-(4-ethoxy-3-methanesulfonyl-quinolin-6-yl)-meth-(Z)-ylidene]-thiazol-4-one;
- 2-amino-5-[1-(4-ethoxy-3-methanesulfonyl-quinolin-6-yl)-meth-(Z)-ylidene]-thiazol-4-one;
- 6-[2-amino-4-oxo-4H-thiazol-(5Z)-ylidenemethyl]-4-(tetrahydro-pyran-4-yloxy)-quinoline-3-carbonitrile;
- 6-[2-amino-4-oxo-4H-thiazol-(5Z)-ylidenemethyl]-4-(2-methoxy-ethoxy)-quinoline-3-carbonitrile;
- 4-butoxy-6-[-cyclopropylamino-4-oxo-4H-thiazol-(5Z)-ylidenemethyl]-quinoline-3-carbonitrile; and
- 6-[$_2$-cyclopropylamino-4-oxo-4H-thiazol-(5Z)-ylidenemethyl]-4-(2-methoxy-ethoxy)-quinoline-3-carbonitrile.

* * * * *